(12) United States Patent
Kadoma et al.

(10) Patent No.: US 8,993,125 B2
(45) Date of Patent: Mar. 31, 2015

(54) TRIAZOLE DERIVATIVE, AND LIGHT-EMITTING ELEMENT, LIGHT-EMITTING DEVICE, ELECTRONIC DEVICE AND LIGHTING DEVICE USING THE TRIAZOLE DERIVATIVE

(75) Inventors: Hiroshi Kadoma, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 177 days.

(21) Appl. No.: 13/110,364

(22) Filed: May 18, 2011

(65) Prior Publication Data

US 2011/0285276 A1    Nov. 24, 2011

(30) Foreign Application Priority Data

May 21, 2010  (JP) .................................. 2010-116997

(51) Int. Cl.
*H01J 1/63* (2006.01)
*C07D 249/08* (2006.01)
(Continued)

(52) U.S. Cl.
CPC .............. *C09K 11/06* (2013.01); *C07D 403/10* (2013.01);
(Continued)

(58) Field of Classification Search
None
See application file for complete search history.

(56) References Cited

U.S. PATENT DOCUMENTS 5,834,130 A    11/1998  Kido
(Continued)

FOREIGN PATENT DOCUMENTS

CN    101203968 A    6/2008
(Continued)

OTHER PUBLICATIONS

Ozasa, S. et al, "Syntheses and Physical Properties of Several Octiphenyls Containing Mixed Linkages," Chemical and Pharmaceutical Bulletin, vol. 29, No. 2, 1981, pp. 344-355.
(Continued)

*Primary Examiner* — J. L. Yang
(74) *Attorney, Agent, or Firm* — Husch Blackwell LLP

(57) ABSTRACT

Objects are to provide the following: a substance that facilitates hole injection and has high triplet excitation energy; a light-emitting element having high emission efficiency using the substance that facilitates hole injection and has high triplet excitation energy; a light-emitting element having low driving voltage; and a light-emitting device, an electronic device, and a lighting device having low power consumption. Provided is a triazole derivative in which a dibenzothiophen-4-yl or dibenzofuran-4-yl group represented by General Formula (G2) is bonded to any one of $Ar^1$ to $Ar^3$ of a triazole derivative represented by General Formula (G1). In the formulae formulas, A represents oxygen or sulfur, $Ar^1$ to $Ar^3$ separately represent a substituted or unsubstituted aryl group having 6 to 13 carbon atoms, and $R^1$ to $R^7$ separately represent hydrogen, an alkyl group having 1 to 4 carbon atoms, or a substituted or unsubstituted aryl group having 6 to 13 carbon atoms.

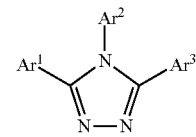

(G1)

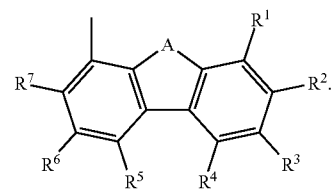

(G2)

16 Claims, 17 Drawing Sheets

(51) Int. Cl.
*C09K 11/06* (2006.01)
*C07D 403/10* (2006.01)
*C07D 409/10* (2006.01)
*H05B 33/14* (2006.01)

(52) U.S. Cl.
CPC ............. *C07D 409/10* (2013.01); *H05B 33/14* (2013.01); *C09K 2211/1029* (2013.01); *C09K 2211/1059* (2013.01); *C09K 2211/1092* (2013.01); *Y10S 428/917* (2013.01)
USPC ............................ 428/690; 549/456; 428/917

(56) References Cited

U.S. PATENT DOCUMENTS

| | | | |
|---|---|---|---|
| 5,869,199 | A | 2/1999 | Kido |
| 5,869,929 | A | 2/1999 | Eida et al. |
| 6,344,283 | B1 | 2/2002 | Inoue et al. |
| 6,623,872 | B2 | 9/2003 | Inoue et al. |
| 6,723,445 | B2 | 4/2004 | Li et al. |
| 6,905,788 | B2 | 6/2005 | Tyan et al. |
| 7,097,918 | B2 | 8/2006 | Inoue et al. |
| 7,355,340 | B2 | 4/2008 | Shitagaki et al. |
| 7,601,435 | B2 | 10/2009 | Shitagaki et al. |
| 7,700,201 | B2 | 4/2010 | Seo et al. |
| 7,723,722 | B2 | 5/2010 | Kawakami et al. |
| 7,796,240 | B2 | 9/2010 | Nomura et al. |
| 7,838,128 | B2 | 11/2010 | Kawakami et al. |
| 7,875,879 | B2 | 1/2011 | Suzuki et al. |
| 7,901,792 | B2 | 3/2011 | Egawa et al. |
| 7,911,135 | B2 | 3/2011 | Sakata et al. |
| 7,927,720 | B2 | 4/2011 | Nomura et al. |
| 7,931,974 | B2 | 4/2011 | Egawa et al. |
| 8,007,927 | B2 | 8/2011 | Lin et al. |
| 8,084,146 | B2 | 12/2011 | Murase et al. |
| 8,101,771 | B2 | 1/2012 | Nomura et al. |
| 8,119,259 | B2 | 2/2012 | Kadoma et al. |
| 8,129,038 | B2 | 3/2012 | Yabunouchi et al. |
| 8,138,303 | B2 | 3/2012 | Chebotareva et al. |
| 8,178,216 | B2 | 5/2012 | Nomura et al. |
| 8,178,217 | B2 | 5/2012 | Nomura et al. |
| 8,221,905 | B2 | 7/2012 | Lin et al. |
| 8,231,984 | B2 | 7/2012 | Shitagaki et al. |
| 8,252,433 | B2 | 8/2012 | Egawa et al. |
| 8,314,101 | B2 | 11/2012 | Kadoma et al. |
| 8,367,850 | B2 | 2/2013 | Ma et al. |
| 8,389,735 | B2 | 3/2013 | Murata et al. |
| 8,563,145 | B2 | 10/2013 | Iwakuma et al. |
| 8,580,402 | B2 | 11/2013 | Lin et al. |
| 8,586,204 | B2 | 11/2013 | Xia et al. |
| 8,623,522 | B2 | 1/2014 | Yabunouchi et al. |
| 8,652,652 | B2 | 2/2014 | Brooks et al. |
| 8,822,708 | B2 | 9/2014 | Ma et al. |
| 8,866,377 | B2 | 10/2014 | Adamovich et al. |
| 2002/0102434 | A1 | 8/2002 | Inoue et al. |
| 2002/0182441 | A1 | 12/2002 | Lamansky et al. |
| 2004/0110030 | A1 | 6/2004 | Inoue et al. |
| 2004/0110958 | A1 | 6/2004 | Nishiyama et al. |
| 2004/0115476 | A1 | 6/2004 | Oshiyama et al. |
| 2005/0031899 | A1 | 2/2005 | Nomura et al. |
| 2005/0048310 | A1 | 3/2005 | Cocchi et al. |
| 2005/0064237 | A1 | 3/2005 | Kato et al. |
| 2005/0221124 | A1 | 10/2005 | Hwang et al. |
| 2006/0180812 | A1 | 8/2006 | Sakata et al. |
| 2006/0263636 | A1 | 11/2006 | Ohsawa et al. |
| 2007/0009758 | A1 | 1/2007 | Funahashi |
| 2007/0149784 | A1 | 6/2007 | Murata et al. |
| 2007/0196692 | A1 | 8/2007 | Ise et al. |
| 2007/0215867 | A1 | 9/2007 | Kawakami et al. |
| 2007/0215889 | A1 | 9/2007 | Kawakami et al. |
| 2007/0216292 | A1 | 9/2007 | Seo et al. |
| 2007/0222376 | A1 | 9/2007 | Ohsawa et al. |
| 2007/0252511 | A1 | 11/2007 | Funahashi |
| 2007/0262693 | A1 | 11/2007 | Seo et al. |
| 2008/0015399 | A1 | 1/2008 | Funahashi |
| 2008/0122345 | A1 | 5/2008 | Sakata et al. |
| 2008/0124572 | A1 | 5/2008 | Mizuki et al. |
| 2008/0135835 | A1 | 6/2008 | Seo et al. |
| 2008/0206598 | A1 | 8/2008 | Ohsawa et al. |
| 2008/0286607 | A1 | 11/2008 | Nomura et al. |
| 2008/0296561 | A1 | 12/2008 | Nomura et al. |
| 2008/0314965 | A1 | 12/2008 | Roberts et al. |
| 2009/0026922 | A1 | 1/2009 | Iwaki et al. |
| 2009/0072718 | A1 | 3/2009 | Nomura et al. |
| 2009/0102361 | A1 | 4/2009 | Miki et al. |
| 2009/0140641 | A1 | 6/2009 | Nomura et al. |
| 2009/0140642 | A1 | 6/2009 | Kadoma et al. |
| 2009/0153034 | A1 | 6/2009 | Lin et al. |
| 2009/0153041 | A1 | 6/2009 | Kawakami et al. |
| 2009/0159877 | A1 | 6/2009 | Meng |
| 2009/0160324 | A1* | 6/2009 | Nomura et al. ............... 313/504 |
| 2009/0184633 | A1 | 7/2009 | Kadoma et al. |
| 2009/0203704 | A1 | 8/2009 | Kadoma et al. |
| 2009/0284138 | A1* | 11/2009 | Yasukawa et al. ............ 313/504 |
| 2009/0295278 | A1 | 12/2009 | Lee et al. |
| 2010/0039024 | A1 | 2/2010 | Wendeborn et al. |
| 2010/0060155 | A1 | 3/2010 | Seo et al. |
| 2010/0090588 | A1 | 4/2010 | Yokoyama et al. |
| 2010/0155714 | A1 | 6/2010 | Seo et al. |
| 2010/0244672 | A1 | 9/2010 | Nomura et al. |
| 2010/0244674 | A1 | 9/2010 | Nomura et al. |
| 2010/0249349 | A1 | 9/2010 | Chebotareva et al. |
| 2010/0314615 | A1 | 12/2010 | Mizuki et al. |
| 2011/0089407 | A1 | 4/2011 | Schmidhalter et al. |
| 2011/0095270 | A1 | 4/2011 | Meng |
| 2011/0095678 | A1 | 4/2011 | Ogita et al. |
| 2011/0156016 | A1 | 6/2011 | Kawamura et al. |
| 2011/0210316 | A1 | 9/2011 | Kadoma et al. |
| 2011/0248246 | A1 | 10/2011 | Ogita et al. |
| 2012/0112169 | A1 | 5/2012 | Mizuki et al. |
| 2012/0138907 | A1 | 6/2012 | Murase et al. |
| 2012/0193613 | A1 | 8/2012 | Kadoma et al. |
| 2012/0197020 | A1 | 8/2012 | Osaka et al. |
| 2012/0199818 | A1 | 8/2012 | Nomura et al. |
| 2012/0286257 | A1 | 11/2012 | Shitagaki et al. |
| 2012/0313506 | A1 | 12/2012 | Egawa et al. |
| 2013/0048971 | A1 | 2/2013 | Kitano et al. |
| 2013/0060033 | A1 | 3/2013 | Seo et al. |
| 2013/0075704 | A1 | 3/2013 | Takasu et al. |
| 2013/0082591 | A1 | 4/2013 | Seo et al. |
| 2013/0112954 | A1 | 5/2013 | Osaka et al. |
| 2014/0008643 | A1 | 1/2014 | Lin et at |
| 2014/0021461 | A1 | 1/2014 | Iwakuma et at |
| 2014/0042413 | A1 | 2/2014 | Xia et al. |
| 2014/0103327 | A1 | 4/2014 | Brooks et at |
| 2014/0159006 | A1 | 6/2014 | Yabunouchi et al. |
| 2014/0326977 | A1 | 11/2014 | Ma et al. |
| 2015/0001524 | A1 | 1/2015 | Brooks et at |

FOREIGN PATENT DOCUMENTS

| | | |
|---|---|---|
| CN | 101379110 A | 3/2009 |
| CN | 101516856 A | 8/2009 |
| CN | 101853923 A | 10/2010 |
| CN | 101867019 A | 10/2010 |
| CN | 101970448 A | 2/2011 |
| CN | 102190653 A | 9/2011 |
| EP | 0 891 121 A1 | 1/1999 |
| EP | 1 616 864 A1 | 1/2006 |
| EP | 1 748 045 A1 | 1/2007 |
| EP | 1 905 768 A1 | 4/2008 |
| EP | 1 962 354 A1 | 8/2008 |
| EP | 2 011 790 A1 | 1/2009 |
| EP | 2 034 538 A1 | 3/2009 |
| EP | 2 055 704 A1 | 5/2009 |
| EP | 2 065 378 A1 | 6/2009 |
| EP | 2 236 506 A1 | 10/2010 |
| EP | 2 363 398 A1 | 9/2011 |
| EP | 2 450 356 A1 | 5/2012 |
| EP | 2 639 231 A1 | 9/2013 |
| JP | 2000-68059 | 3/2000 |
| JP | 2002-352957 | 12/2002 |
| JP | 2003-7467 | 1/2003 |
| JP | 2004-14440 | 1/2004 |

(56) References Cited

FOREIGN PATENT DOCUMENTS

| | | |
|---|---|---|
| JP | 2004-71380 | 3/2004 |
| JP | 2004-152527 | 5/2004 |
| JP | 2004-204238 | 7/2004 |
| JP | 2004-214050 | 7/2004 |
| JP | 2004-220931 | 8/2004 |
| JP | 2004-253298 | 9/2004 |
| JP | 2005-166680 | 6/2005 |
| JP | 2005-320277 | 11/2005 |
| JP | 2006-324650 A | 11/2006 |
| JP | 2007-077094 A | 3/2007 |
| JP | 2007-126403 A | 5/2007 |
| JP | 3926791 B2 | 6/2007 |
| JP | 2007-189001 | 7/2007 |
| JP | 2007-197429 | 8/2007 |
| JP | 2007-227658 | 9/2007 |
| JP | 2008-106051 A | 5/2008 |
| JP | 2008-239613 | 10/2008 |
| JP | 4188401 B2 | 11/2008 |
| JP | 2008-308490 | 12/2008 |
| JP | 2009-149629 A | 7/2009 |
| JP | 2009-149631 A | 7/2009 |
| JP | 2009-149632 A | 7/2009 |
| JP | 2009-167173 | 7/2009 |
| JP | 2009-526111 | 7/2009 |
| JP | 2009-267255 A | 11/2009 |
| JP | 2010-056190 A | 3/2010 |
| JP | 2011-511821 | 4/2011 |
| KR | 2008-0005441 A | 1/2008 |
| KR | 2010-0123716 A | 11/2010 |
| KR | 2011-0042004 A | 4/2011 |
| TW | 200940554 A | 10/2009 |
| WO | WO 98/30071 A1 | 7/1998 |
| WO | WO 03/007394 A2 | 1/2003 |
| WO | WO 03/058667 A1 | 7/2003 |
| WO | WO 2004/043937 A1 | 5/2004 |
| WO | WO 2004/094389 A1 | 11/2004 |
| WO | WO 2005/108348 A1 | 11/2005 |
| WO | WO 2005/113531 A1 | 12/2005 |
| WO | WO 2006/115232 A1 | 11/2006 |
| WO | WO 2007/020881 A1 | 2/2007 |
| WO | WO-2007/026847 | 3/2007 |
| WO | WO 2007/069569 A1 | 6/2007 |
| WO | WO 2007/074893 A1 | 7/2007 |
| WO | WO 2007/090773 A1 | 8/2007 |
| WO | WO 2007/125714 A1 | 11/2007 |
| WO | WO 2007/142083 A1 | 12/2007 |
| WO | WO 2008/023628 A1 | 2/2008 |
| WO | WO 2008/031743 A1 | 3/2008 |
| WO | WO 2009/021126 A2 | 2/2009 |
| WO | WO 2009/084512 A1 | 7/2009 |
| WO | WO 2009/100991 A1 | 8/2009 |
| WO | WO 2010/013675 A1 | 2/2010 |
| WO | WO 2010/013676 A1 | 2/2010 |
| WO | WO 2010/027004 A1 | 3/2010 |
| WO | WO 2010/122810 A1 | 10/2010 |

OTHER PUBLICATIONS

Goldsmith, C.R. et al., "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.
Onishi.T et al, "A Method of Measuring an Energy Level," *High Molecular EL Materials Development of Light-Emitting High Molecular Compounds*, Kyoritsu Shuppan, Dec. 25, 2004, p. 64-67 (with English translation, pp. 1-3).
Hughes, G. et al, "Electron-Transporting Materials for Organic Electroluminescent and Electrophosphorescent Devices," Journal of Materials Chemistry, The Royal Society of Chemistry, vol. 15, 2005, pp. 94-107.
Agata, Y. et al, "Syntheses and Properties of Novel Quarterphenylene-Based Materials for Blue Organic Light-Emitting Devices," Chemistry Letters, The Chemical Society of Japan, vol. 36, No. 2, Feb. 1, 2007, pp. 316-317.
Kim, J.H. et al, "New Host Materials with High Triplet Energy Level for Blue-Emitting Electrophosphorescent Device," Synthetic Metals, vol. 157, No. 18-20, 2007, pp. 743-750.
International Search Report re application No. PCT/JP2008/058584, dated Jun. 10, 2008.
WrittenOpinion re application No. PCT/JP2008/058584, dated Jun. 10, 2008.
International Search Report re application No. PCT/JP2008/072226, dated Jan. 6, 2009.
Written Opinion re application No. PCT/JP2008/072226, dated Jan. 6, 2009.
International Search Report re application No. PCT/JP2009/065373, dated Oct. 6, 2009.
Written Opinion re application No. PCT/JP2009/065373, dated Oct. 6, 2009.
European Search Report re application No. EP 10158693.1, dated Aug. 13, 2010.
European Search Report re application No. EP 08864807.6, dated Apr. 4, 2011.
Azole, http://en.wikipedia.org/wiki/Azole, pp. 1-3 pages, Wikipedia Foundation.
Office Action U.S. Appl. No. 12/748,902: Dated Mar. 29, 2012.
Remmers.M et al., "The Optical, Electronic, and Electroluminescent Properties of Novel Poly(p-phenylene)-Related Polymers", Macromolecules, 1996, vol. 29, pp. 7432-7445.
European Search Report re Application No. EP11155124.8, dated Jun. 24, 2011.
Zhang, M. et al., "Highly-Efficient Solution-Processed OLEDs Based on New Bipolar Emitters," Chemical Communications, 2010, vol. 46, pp. 3923-3925.
Chinese Office Action re Application No. CN 201210579702.0, dated Dec. 26, 2013.
Wermuth, C.G. "Molecular Variations Based on Isosteric Replacements," *The Practice of Medicinal Chemistry*, Academic Press Ltd., 1996, pp. 204-237.

\* cited by examiner

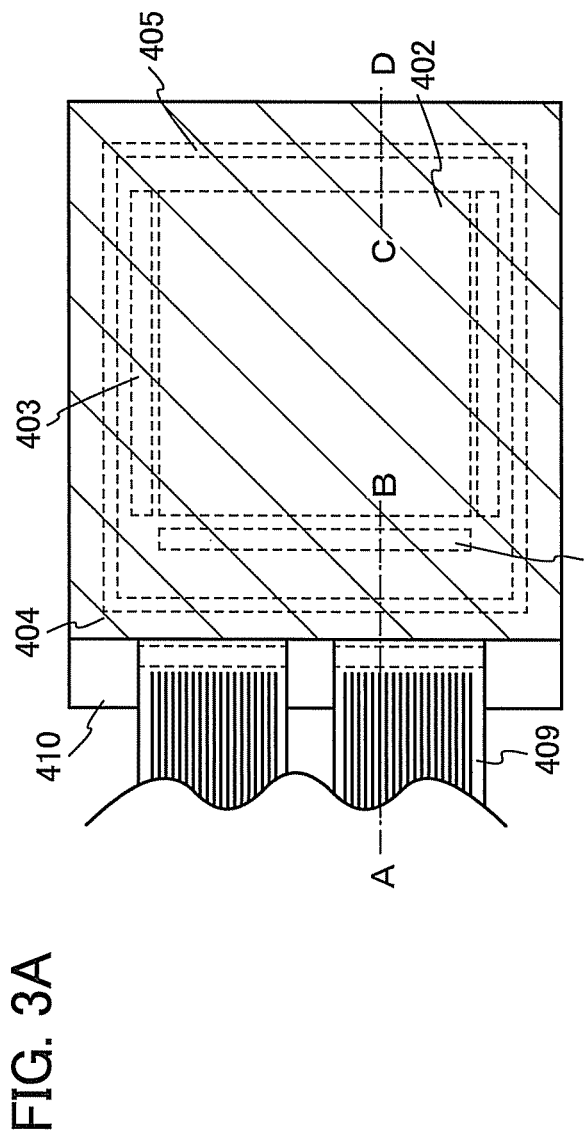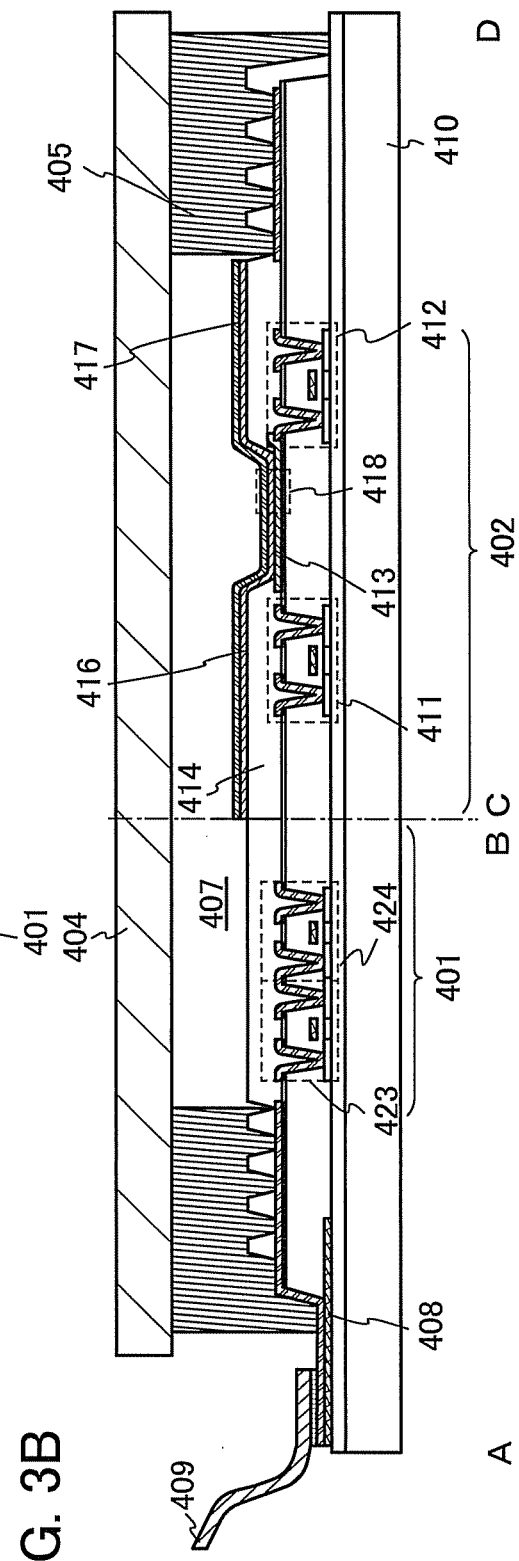

TRIAZOLE DERIVATIVE, AND LIGHT-EMITTING ELEMENT, LIGHT-EMITTING DEVICE, ELECTRONIC DEVICE AND LIGHTING DEVICE USING THE TRIAZOLE DERIVATIVE

BACKGROUND OF THE INVENTION

1. Field of the Invention

The present invention relates to a triazole derivative. Further, the present invention relates to a current-excitation light-emitting element including the triazole derivative, and a light-emitting device, an electronic device and a lighting device each including the light-emitting element.

2. Description of the Related Art

In recent years, research and development have been extensively conducted on light-emitting elements utilizing electroluminescence (EL). In the basic structure of such a light-emitting element, a layer containing a light-emitting substance is interposed between a pair of electrodes. By voltage application to this element, light emission from the light-emitting substance can be obtained.

Such light-emitting elements are self-luminous elements and hence have advantages over liquid crystal displays in having high pixel visibility and eliminating the need for backlights, for example; thus, light-emitting elements are suitable for flat panel display elements. Light-emitting elements are also highly advantageous in that they can be thin and lightweight. Furthermore, very high speed response to an inputted signal is one of the features of such elements.

Furthermore, since such light-emitting elements can be formed in a film form, they make it possible to provide planar light emission. This is a difficult feature to obtain with point light sources typified by incandescent lamps and LEDs or linear light sources typified by fluorescent lamps. Thus, light-emitting elements also have great potential as planar light sources applicable to lighting devices and the like.

Such light-emitting elements utilizing EL can be broadly classified according to whether a light-emitting substance is an organic compound or an inorganic compound. In the case of an organic EL element in which a layer containing an organic compound used as a light-emitting substance is provided between a pair of electrodes, application of a voltage to the light-emitting element causes injection of electrons from a cathode and holes from an anode into the layer containing the organic compound having a light-emitting property and thus a current flows. The injected electrons and holes then lead the organic compound having a light-emitting property to its excited state, whereby light emission is obtained from the excited organic compound having a light-emitting property.

An excited state formed by an organic compound can be a singlet excited state or a triplet excited state. Luminescence from a singlet excited state (S*) is called fluorescence, and luminescence from a triplet excited state (T*) is called phosphorescence. In addition, the ratio of S* to T* formed in the light-emitting element is statistically considered to be 1:3.

At room temperature, observations of a compound that can convert energy of a singlet excited state into luminescence (hereinafter, referred to as a fluorescent compound) usually show only luminescence from the singlet excited state (fluorescence) without luminescence from the triplet excited state (phosphorescence). Thus, the internal quantum efficiency (the ratio of generated photons to injected carriers) of a light-emitting element using a fluorescent compound is assumed to have a theoretical limit of 25% based on a S*-to-T* ratio of 1:3.

In contrast, with a compound that can convert energy of a triplet excited state into luminescence (hereinafter, called a phosphorescent compound), luminescence from the triplet excited state (phosphorescence) is observed. Further, with a phosphorescent compound, since intersystem crossing (i.e., transition from a singlet excited state to a triplet excited state) easily occurs, the internal quantum efficiency can be increased to 75% to 100% in theory. In other words, an element using a phosphorescent compound can have three to four times as high emission efficiency as that of an element using a fluorescent compound. For these reasons, a light-emitting element using a phosphorescent compound has been actively developed in recent years in order to achieve a highly-efficient light-emitting element.

When a light-emitting layer of a light-emitting element is formed using a phosphorescent compound described above, in order to suppress concentration quenching or quenching due to triplet-triplet annihilation in the phosphorescent compound, the light-emitting layer is often formed such that the phosphorescent compound is dispersed in a matrix of another compound. Here, the compound serving as the matrix is called a host material, and the compound dispersed in the matrix, such as a phosphorescent compound, is called a guest material.

In the case where a phosphorescent compound is a guest material, a host material needs to have higher triplet excitation energy (an energy difference between a ground state and a triplet excited state) than the phosphorescent compound Furthermore, since singlet excitation energy (an energy difference between a ground state and a singlet excited state) is higher than triplet excitation energy, a substance that has high triplet excitation energy also has high singlet excitation energy. Therefore the above substance that has high triplet excitation energy is also effective in a light-emitting element using a fluorescent compound as a light-emitting substance.

In Patent Document 1, 3-(4-biphenylyl)-5-(4-tert-butylphenyl)-4-phenyl-1,2,4-triazole (abbreviation: TAZ) is used as a host material for a phosphorescent compound that emits green light.

REFERENCE

Patent Document

Patent Document 1: Japanese Published Patent Application No. 2002-352957

SUMMARY OF THE INVENTION

A compound having high triplet excitation energy like TAZ is useful as a host material for a phosphorescent compound. However, TAZ has high singlet excitation energy and it is also used as a hole-blocking material; that is, a feature of TAZ is that it has great difficulty with hole injection. Thus, when TAZ is used as a host material of a light-emitting layer, holes are difficult to inject into the light-emitting layer, and accordingly a light-emitting region has a strong tendency to be concentrated in and around an interface between the light-emitting layer and a hole-transport layer. If the light-emitting region is concentrated in the interface, there occurs concentration quenching of a light-emitting substance in an excited state or quenching due to triplet-triplet annihilation, which could result in a decrease of emission efficiency.

Therefore, an object of one embodiment of the present invention is to provide a substance that facilitates hole injection and has high triplet excitation energy.

Another object of one embodiment of the present invention is to provide a light-emitting element having high emission efficiency and low driving voltage, which uses the substance that facilitates hole injection and has high triplet excitation energy. Still another object is to provide a light-emitting device, an electronic device, and a lighting device each having low power consumption.

The present inventors have placed their focus on a triazole derivative which includes, in the same molecule, a triazole skeleton having an electron-transport property and high triplet excitation energy and a dibenzothiophene skeleton (or a dibenzofuran skeleton) having a hole-transport property. Then, the inventors have found that the triazole derivative, in which a triazole skeleton and a dibenzothiophene skeleton (or a dibenzofuran skeleton) are bonded through an arylene group, can be easily synthesized and has high triplet excitation energy and an electron- and hole-transport properties. More specifically, the inventors have found that the triazole derivative is a 1,2,4-triazole derivative, in which an aryl group is bonded to each of the 3-, 4-, and 5-positions and a dibenzothiophen-4-yl group or a dibenzofuran-4-yl group is bonded to any one of the aryl groups, and the triazole derivative has high triplet excitation energy and an electron- and hole-transport properties.

One embodiment of the present invention is a triazole derivative in which a dibenzothiophen-4-yl group or a dibenzofuran-4-yl group represented by General Formula (G2) is bonded to any one of Ar$^1$ to Ar$^3$ of a triazole derivative represented by General Formula (G1).

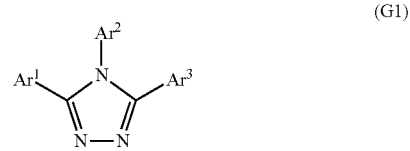

(G1)

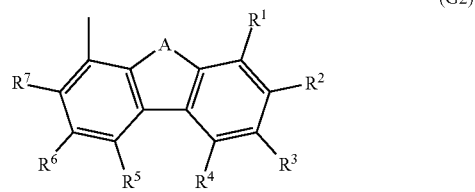

(G2)

In General Formulae (G1) and (G2), A represents oxygen or sulfur, Ar$^1$ to Ar$^3$ separately represent a substituted or unsubstituted aryl group having 6 to 13 carbon atoms, and R$^1$ to R$^7$ separately represent hydrogen, an alkyl group having 1 to 4 carbon atoms, or a substituted or unsubstituted aryl group having 6 to 13 carbon atoms.

One embodiment of the present invention is a triazole derivative represented by General Formula (G3).

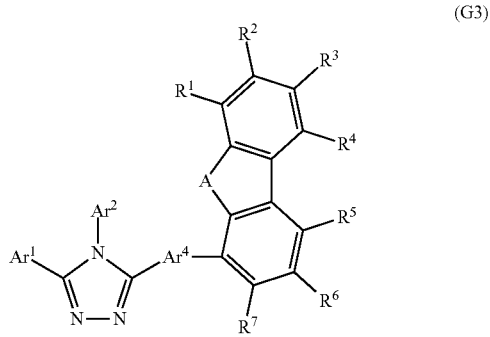

(G3)

In General Formula (G3), A represents oxygen or sulfur, Ar$^1$ and Ar$^2$ separately represent a substituted or unsubstituted aryl group having 6 to 13 carbon atoms, Ar$^4$ represents a substituted or unsubstituted arylene group having 6 to 13 carbon atoms, and R$^1$ to R$^7$ separately represent hydrogen, an alkyl group having 1 to 4 carbon atoms, or a substituted or unsubstituted aryl group having 6 to 13 carbon atoms.

One embodiment of the present invention is a triazole derivative represented by General Formula (G4).

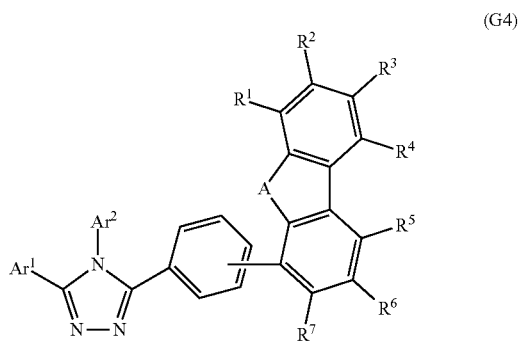

(G4)

In General Formula (G4), A represents oxygen or sulfur, Ar$^1$ and Ar$^2$ separately represent a substituted or unsubstituted aryl group having 6 to 13 carbon atoms, and R$^1$ to R$^7$ separately represent hydrogen, an alkyl group having 1 to 4 carbon atoms, or a substituted or unsubstituted aryl group having 6 to 13 carbon atoms.

One embodiment of the present invention is a triazole derivative represented by General Formula (G5).

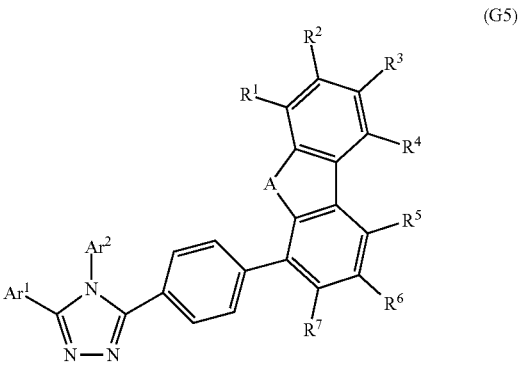

(G5)

In General Formula (G5), A represents oxygen or sulfur, Ar$^1$ and Ar$^2$ separately represent a substituted or unsubstituted aryl group having 6 to 13 carbon atoms, and R$^1$ to R$^7$ separately represent hydrogen, an alkyl group having 1 to 4 carbon atoms, or a substituted or unsubstituted aryl group having 6 to 13 carbon atoms.

In any of the above triazole derivatives, Ar$^1$ and Ar$^2$ are each preferably a phenyl group for easier synthesis.

Another embodiment of the present invention is a light-emitting element using any of the above-described triazole derivatives, and specifically, a light-emitting element including any of the above-described triazole derivatives between a pair of electrodes.

Still another embodiment of the present invention is a light-emitting element which includes a light-emitting layer between a pair of electrodes, in which the light-emitting layer has any of the above triazole derivatives.

Since the above triazole derivatives have high triplet excitation energy, a more advantageous effect can be obtained when the light-emitting layer includes any of the above triazole derivatives and a substance that emits phosphorescence. By using any of the above triazole derivatives, highly efficient light emission can be obtained even with a substance that emits phosphorescence, especially a substance that emits short-wavelength light having an emission peak greater than or equal to 400 nm and less than or equal to 500 mm.

The light-emitting device of one embodiment of the present invention includes a light-emitting element having any of the above triazole derivatives and a control circuit which controls light emission of the light-emitting element. The light-emitting device in this specification refers to an image display device and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

The scope of the invention encompasses an electronic device using a light-emitting element of one embodiment of the invention for a display portion. Thus, an electronic device according to one embodiment of the invention includes a display portion, in which the display portion includes any of the above triazole derivatives and a control circuit which controls light emission of the light-emitting element.

One embodiment of the present invention can provide a substance that facilitates hole injection and has high triplet excitation energy.

By using a triazole derivative of one embodiment of the present invention, a light-emitting element having high emission efficiency can be provided. Further, a light-emitting element having low driving voltage can be provided. Furthermore, a light-emitting device, an electronic device, and a lighting device each having low power consumption can be provided.

BRIEF DESCRIPTION OF THE DRAWINGS

FIGS. 3A and 3B illustrate a light-emitting device according to one embodiment of the present invention.

DETAILED DESCRIPTION OF THE INVENTION

Figure 1A:
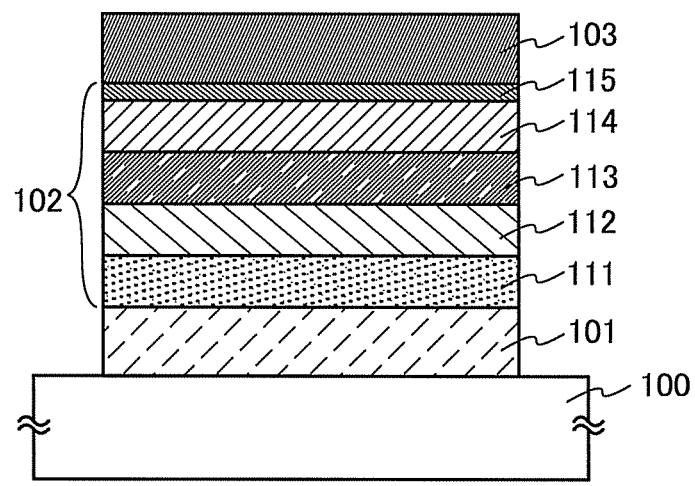
FIGS. 1A and 1B each illustrate a light-emitting element of an embodiment of the present invention.

Embodiments of the present invention will now be described with reference to the accompanying drawings. Note that the invention is not limited to the description given below, and it will be easily understood by those skilled in the art that various changes and modifications can be made without departing from the spirit and scope of the invention. Therefore, the invention should not be construed as being limited to the description in the following embodiments.

Embodiment 1

In Embodiment 1, a triazole derivative of one embodiment of the present invention will be described.

A triazole derivative of one embodiment of the present invention includes, in the same molecule, a triazole skeleton having an electron-transport property and high triplet excitation energy and a dibenzothiophene skeleton (or a dibenzofuran skeleton) having a hole-transport property. Specifically, the triazole derivative is a 1,2,4-triazole derivative in which an aryl group is bonded to each of the 3-, 4-, and 5-positions and a dibenzothiophen-4-yl group or a dibenzofuran-4-yl group is bonded to any one of the aryl groups.

One embodiment of the present invention is a triazole derivative in which a dibenzothiophen-4-yl group or a dibenzofuran-4-yl group represented by General Formula (G2) is bonded to any one of $Ar^1$ to $Ar^3$ of a triazole derivative represented by General Formula (G1).

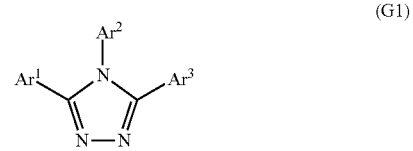

(G1)

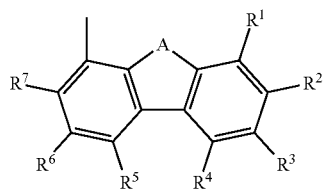
(G2)

In General Formulae (G1) and (G2), A represents oxygen or sulfur, $Ar^1$ to $Ar^3$ separately represent a substituted or unsubstituted aryl group having 6 to 13 carbon atoms, and $R^1$ to $R^7$ separately represent hydrogen, an alkyl group having 1 to 4 carbon atoms, or a substituted or unsubstituted aryl group having 6 to 13 carbon atoms.

An example of the above triazole derivative is a triazole derivative represented by General Formula (G3).

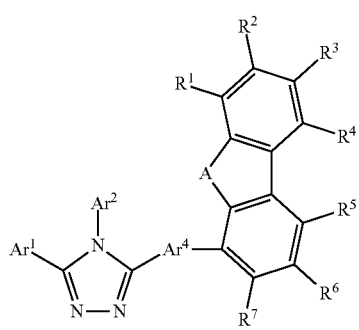
(G3)

In General Formula (G3), A represents oxygen or sulfur, $Ar^1$ and $Ar^2$ separately represent a substituted or unsubstituted aryl group having 6 to 13 carbon atoms, $Ar^4$ represents a substituted or unsubstituted arylene group having 6 to 13 carbon atoms, and $R^1$ to $R^7$ separately represent hydrogen, an alkyl group having 1 to 4 carbon atoms, or a substituted or unsubstituted aryl group having 6 to 13 carbon atoms.

As a triazole derivative of one embodiment of the present invention, a triazole derivative represented by General Formula (G4) is preferred for easier synthesis, and a triazole derivative represented by General Formula (G5) is more preferred for easier synthesis due to its reduced steric hindrance.

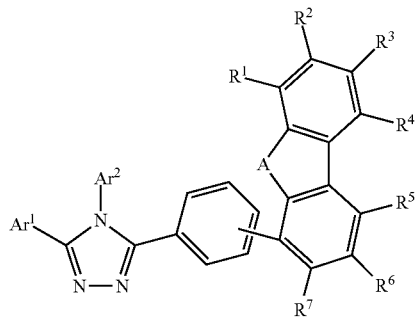
(G4)

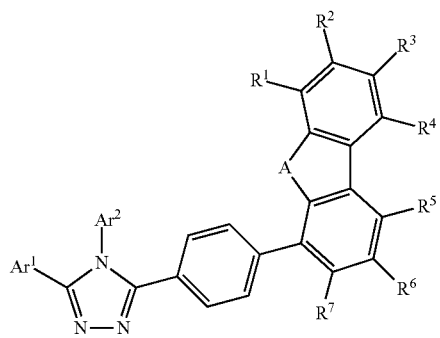
(G5)

In General Formulae (G4) and (G5), A represents oxygen or sulfur, $Ar^1$ and $Ar^2$ separately represent a substituted or unsubstituted aryl group having 6 to 13 carbon atoms, and $R^1$ to $R^7$ separately represent hydrogen, an alkyl group having 1 to 4 carbon atoms, or a substituted or unsubstituted aryl group having 6 to 13 carbon atoms.

Examples of the specific structures of $Ar^1$ to $Ar^3$ in a triazole derivative of one embodiment of the present invention include substituents represented by Structural Formulae (1-1) to (1-14).

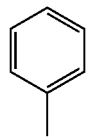
(1-1)

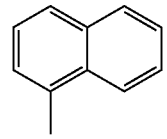
(1-2)

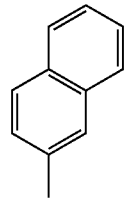
(1-3)

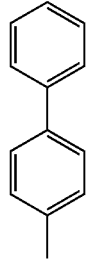
(1-4)

(1-5) 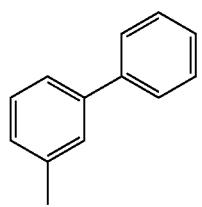
(1-6) 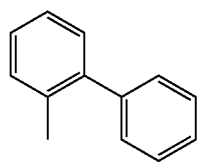
(1-7) 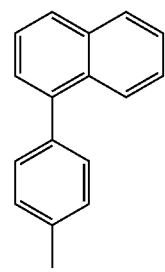
(1-8) 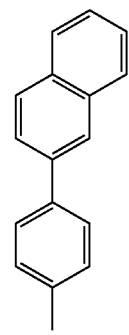
(1-9) 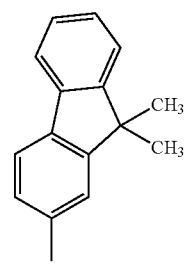
(1-10) 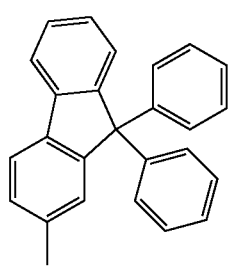
(1-11) 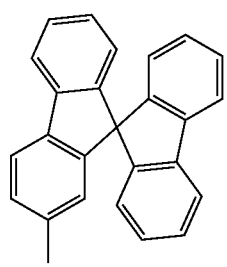
(1-12) 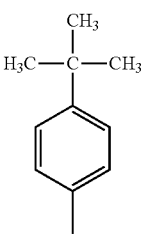
(1-13)
(1-14)
Examples of the specific structures of $Ar^4$ in a triazole derivative of one embodiment of the present invention include substituents represented by Structural Formulae (2-1) to (2-15).
(2-1) 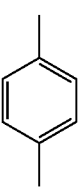
(2-2) 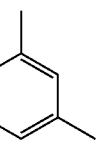
(2-3) 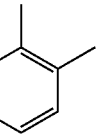

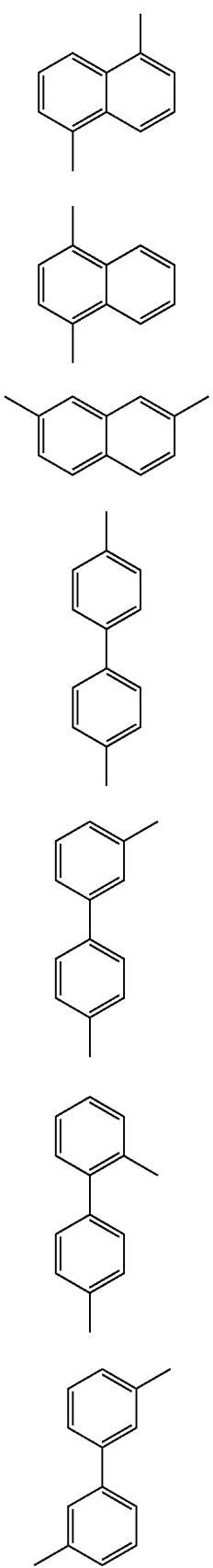
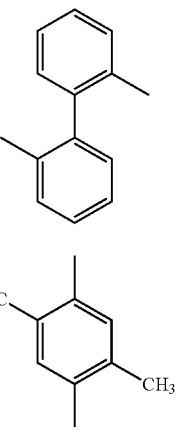
Examples of the specific structures of $R^1$ to $R^7$ in a triazole derivative of one embodiment of the present invention include substituents represented by Structural Formulae (3-1) to (3-23):

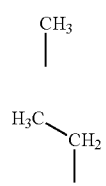 (3-2)
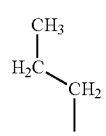 (3-3)
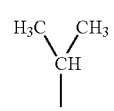 (3-4)
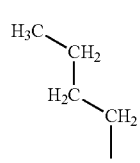 (3-5)
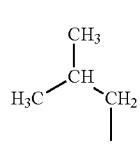 (3-6)
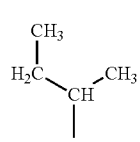 (3-7)
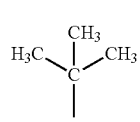 (3-8)
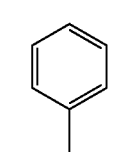 (3-9)
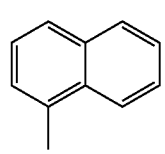 (3-10)
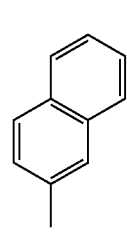 (3-11)
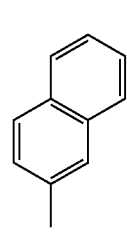 (3-12)
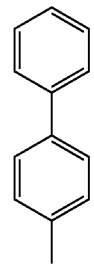 (3-13)
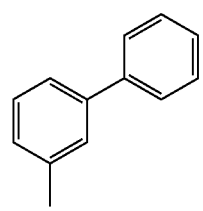 (3-14)
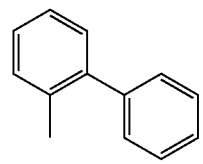 (3-15)
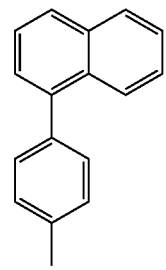 (3-16)
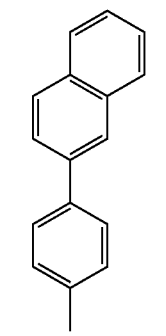 (3-17)
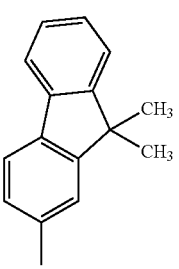 (3-18)

(3-19)

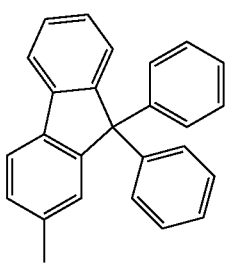

(3-20)

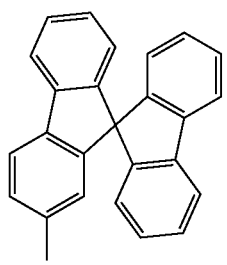

(3-21)

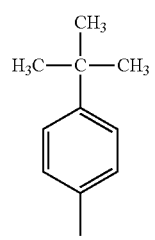

(3-22)

(3-23)

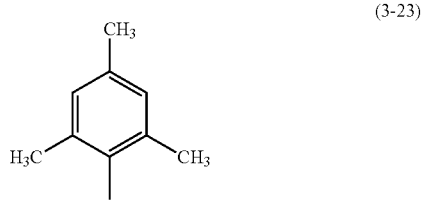

In a triazole derivative of one embodiment of the present invention, $Ar^1$ and $Ar^2$ are each preferably a phenyl group for easier synthesis. Furthermore, $Ar^1$ and $Ar^2$ are each preferably a phenyl group also in order to obtain high triplet excitation energy.

Specific examples of a triazole derivative of one embodiment of the present invention include, but are not limited to, triazole derivatives represented by Structural Formulae (100) to (167) and (200) to (267).

(100)

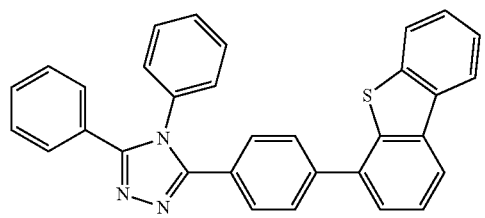

(101)

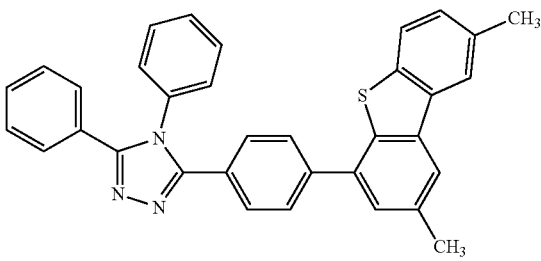

(102)

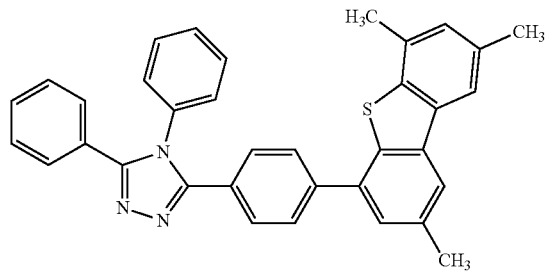

(103)

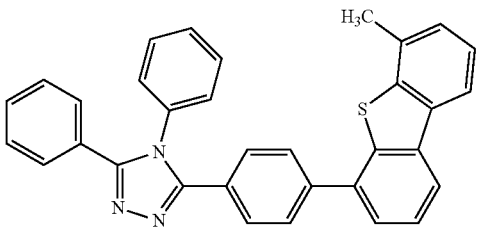

-continued
(104)
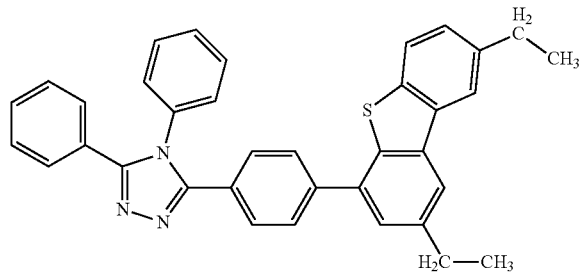
(105)
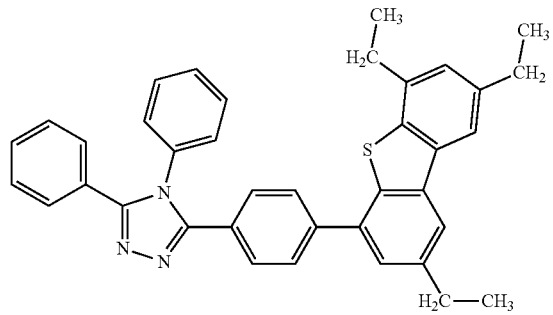
(106)
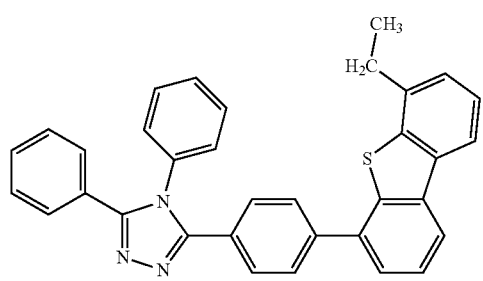
(107)
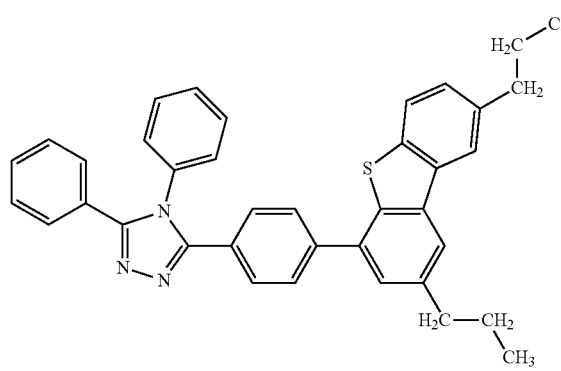
(108)
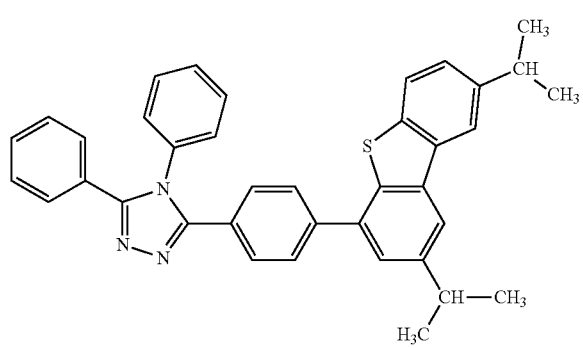
(109)
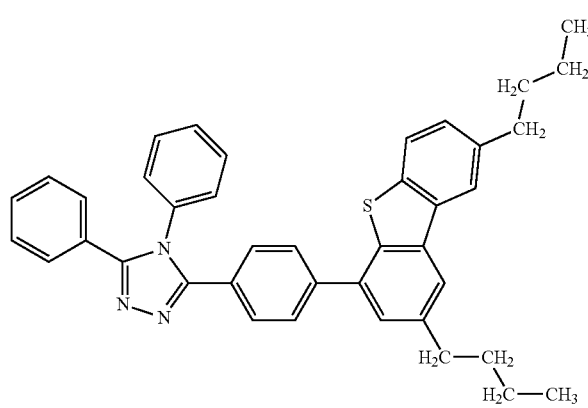
(110)
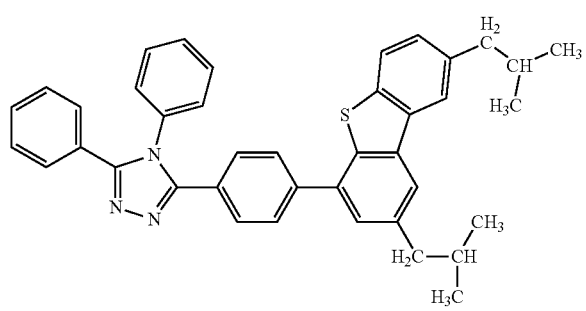
(111)
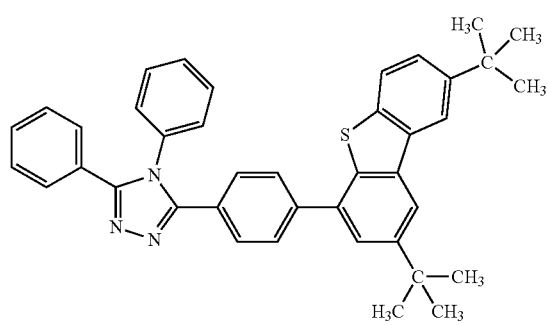

-continued
(112)
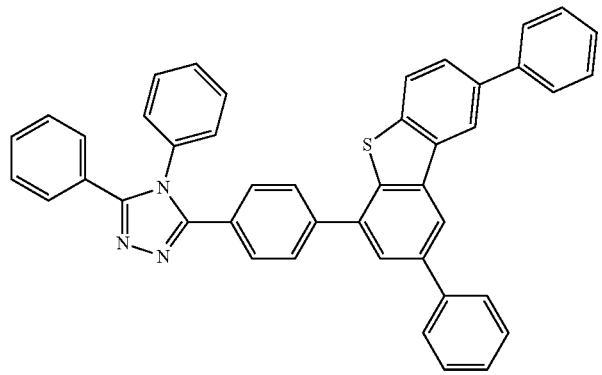
(113)
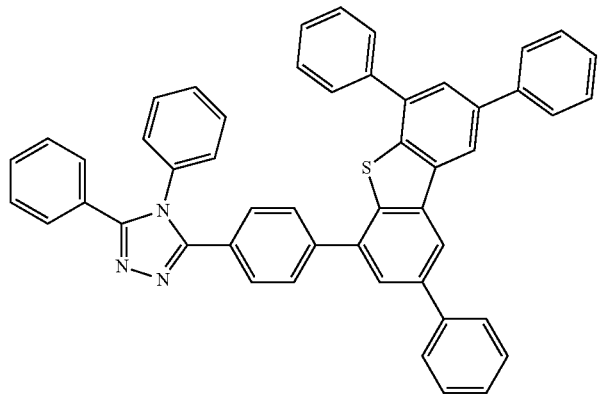
(114)
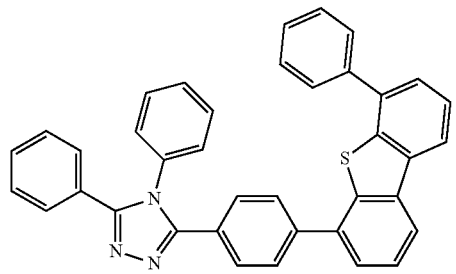
(115)
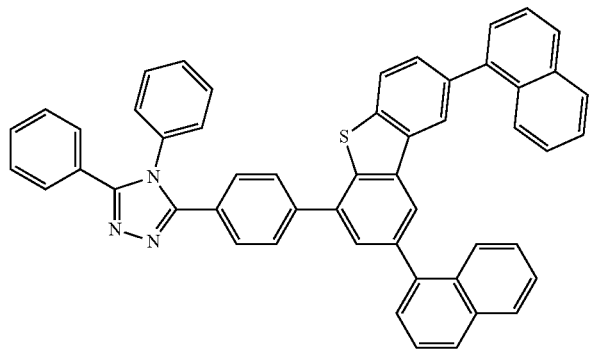
(116)
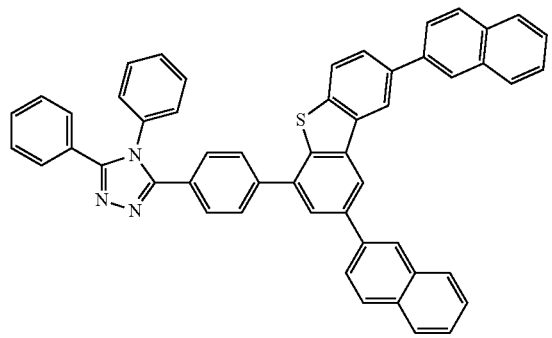
(117)
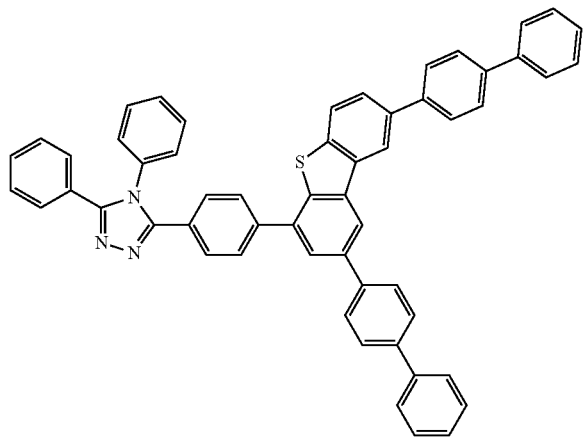
(118)
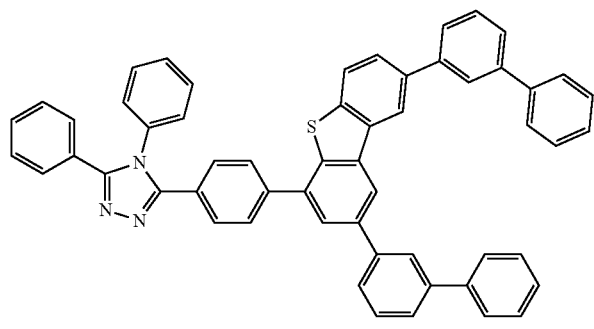
(119)
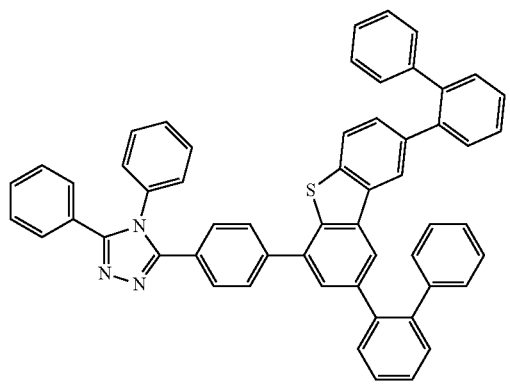

-continued
(120)
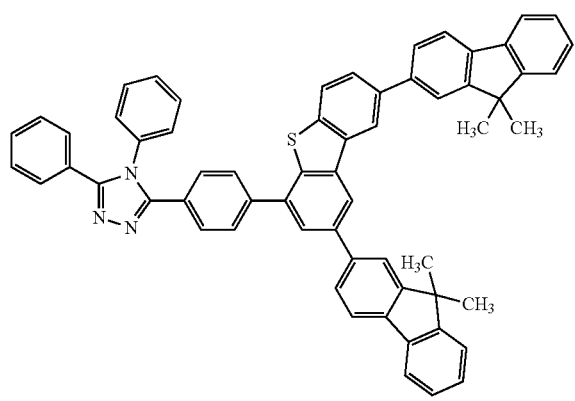
(121)
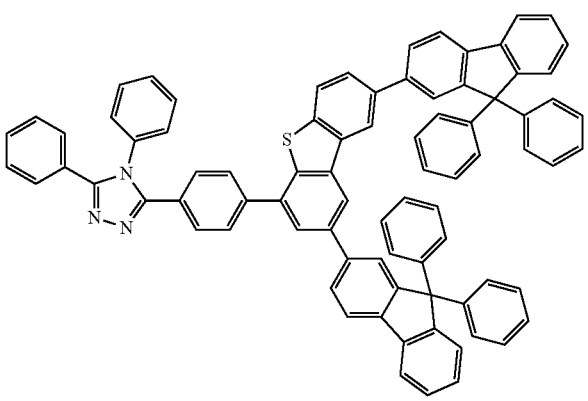
(122)
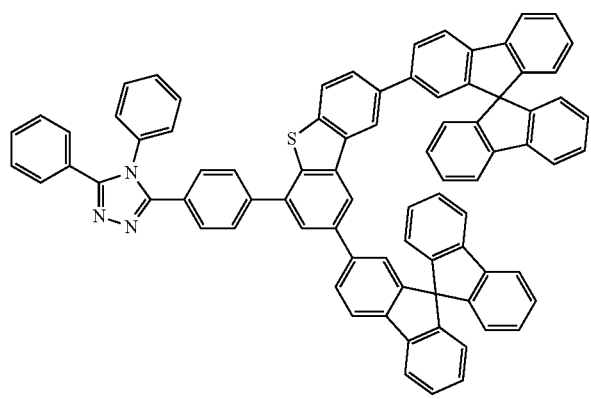
(123)
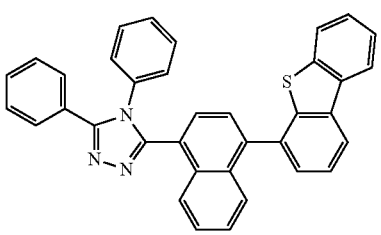
(124)
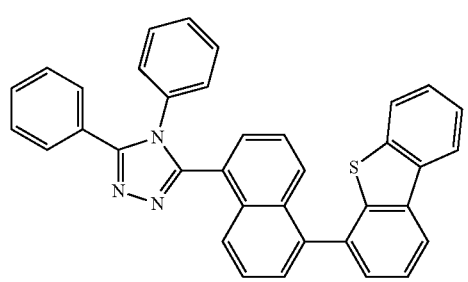
(125)
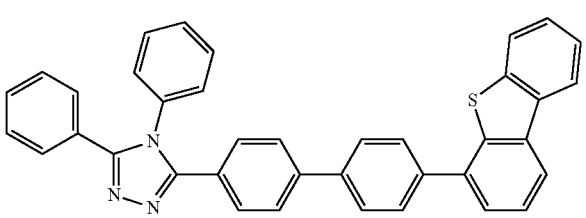
(126)
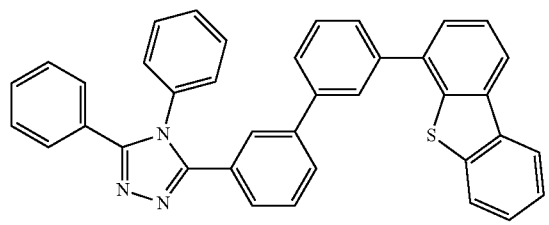
(127)
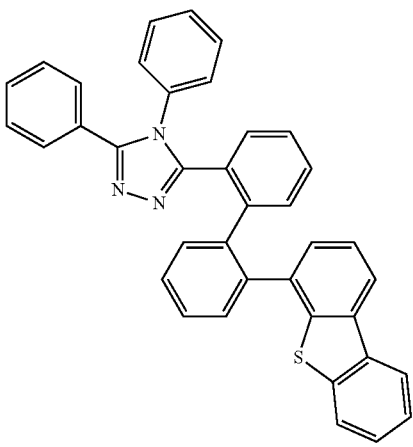

-continued
(128)
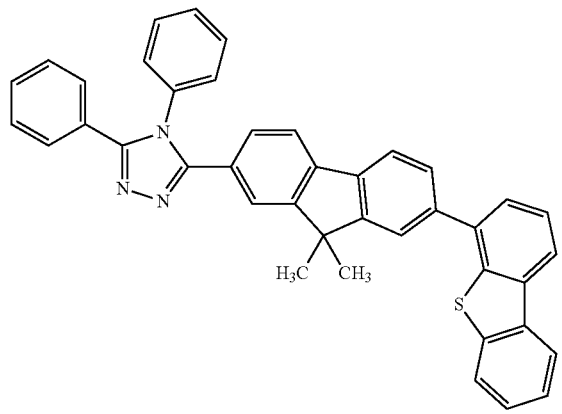
(129)
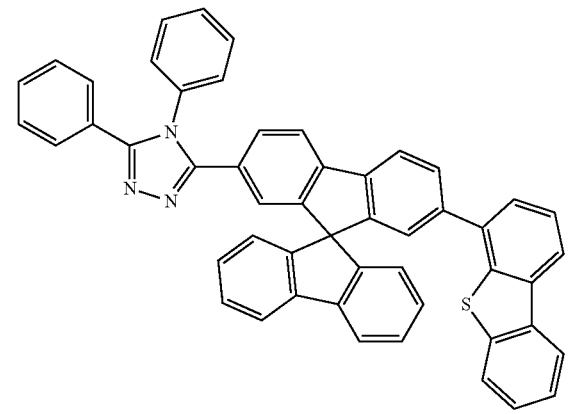
(130)
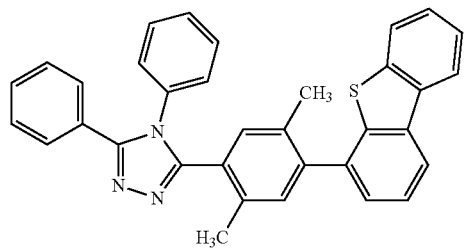
(131)
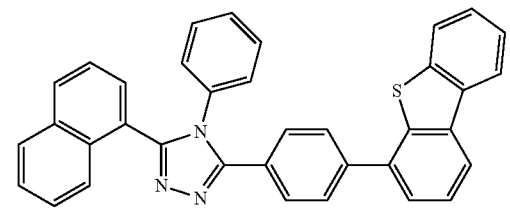
(132)
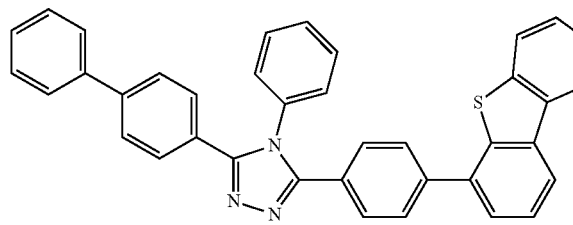
(133)
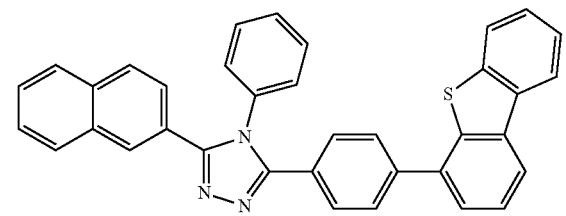
(134)
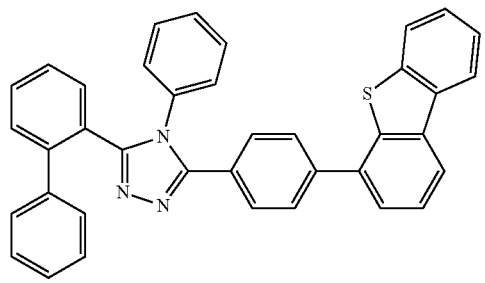
(135)
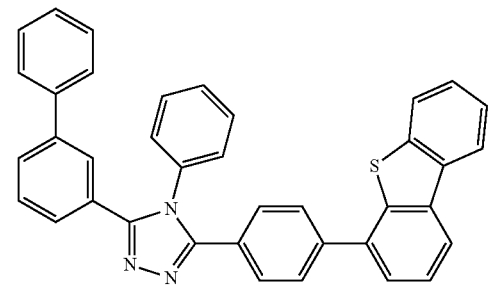
(136)
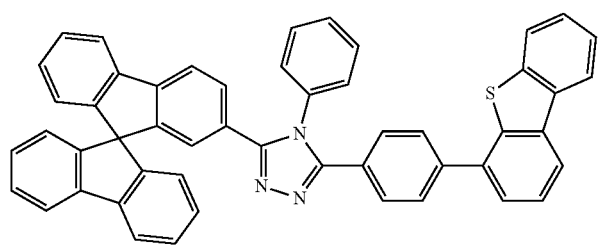
(137)
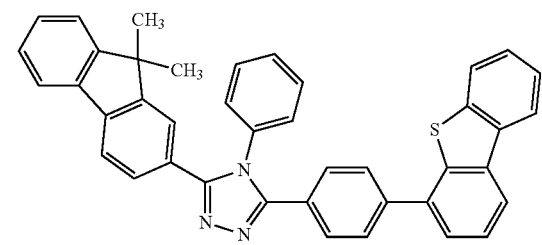

-continued
(138)
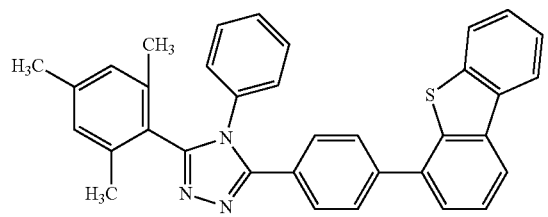
(139)
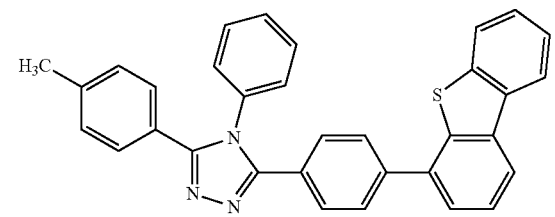
(140)
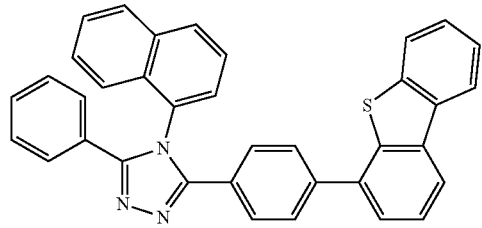
(141)
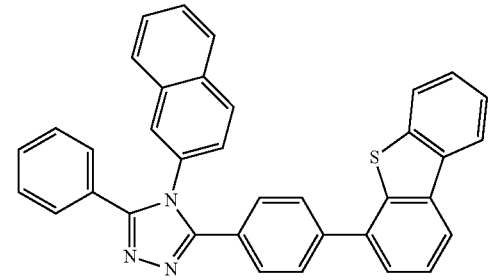
(142)
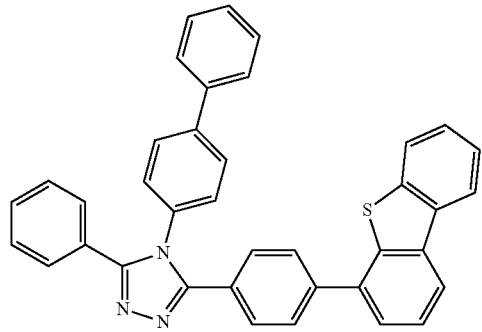
(143)
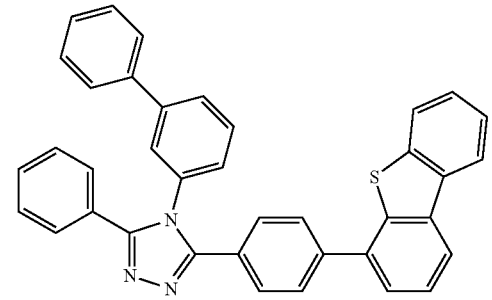
(144)
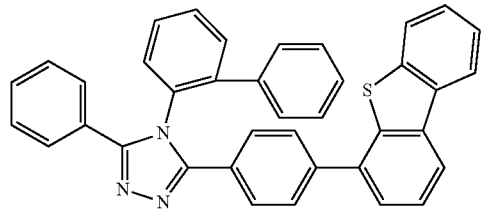
(145)
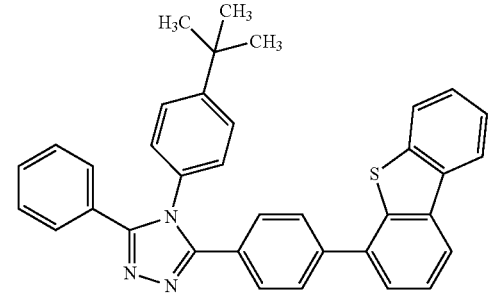
(146)
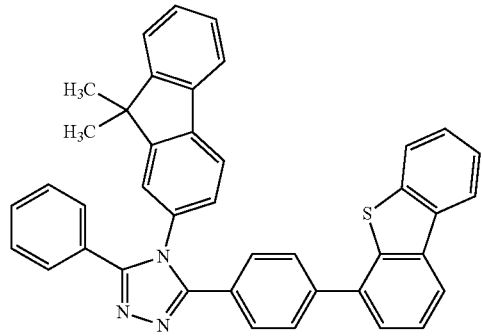
(147)
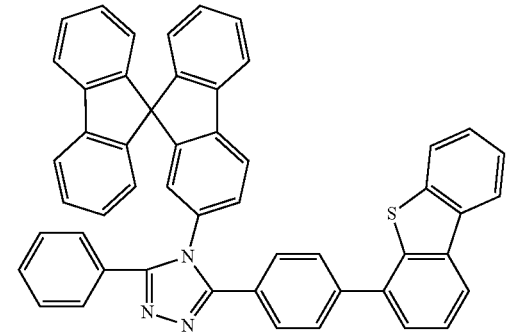

-continued
(148) 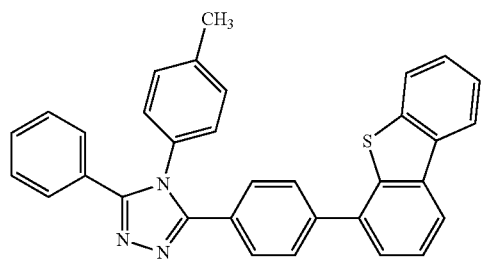
(149) 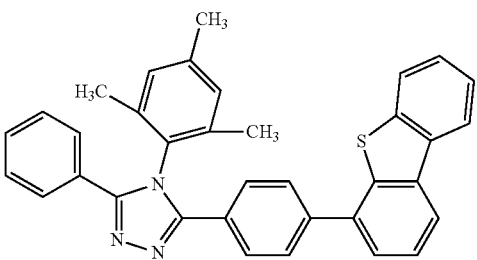
(150) 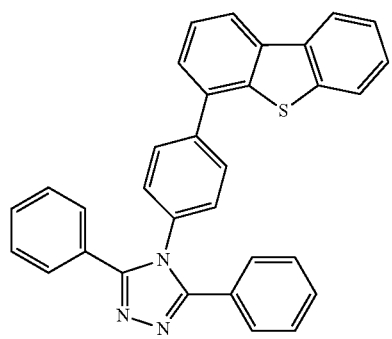
(151) 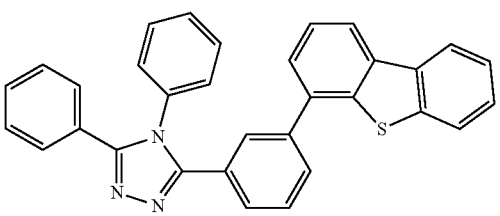
(152) 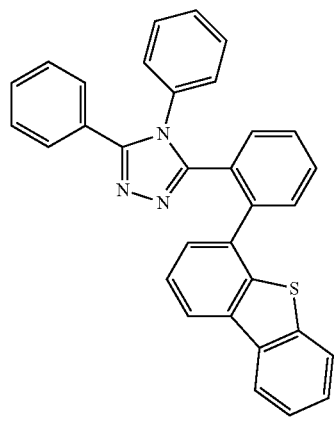
(153) 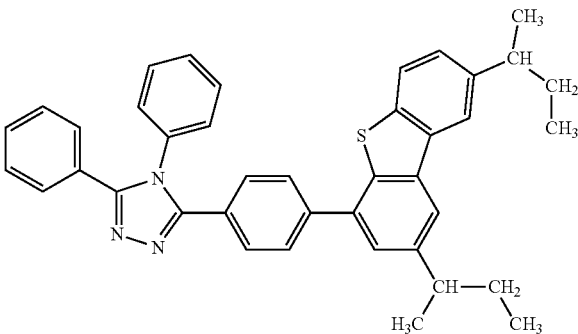
(154) 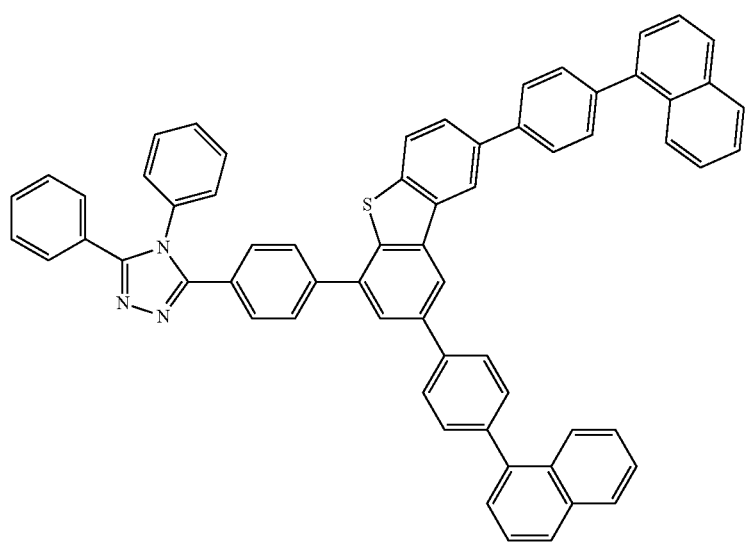

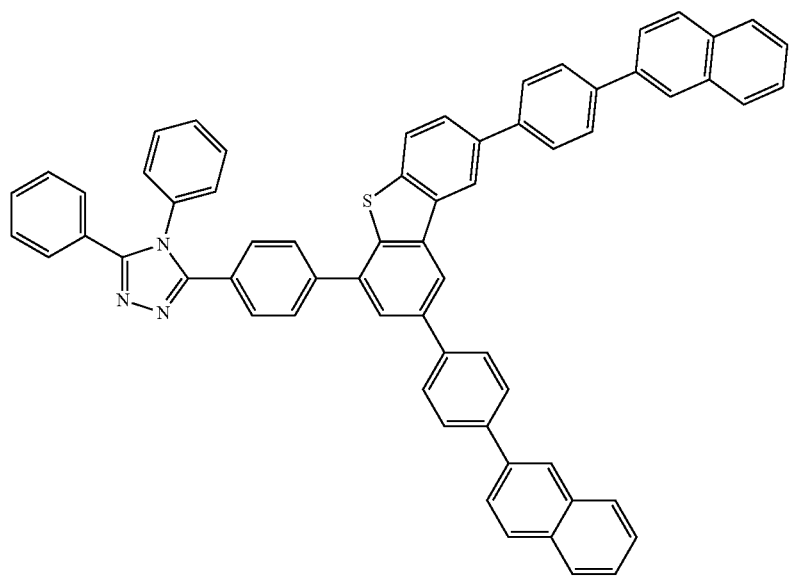
(155)
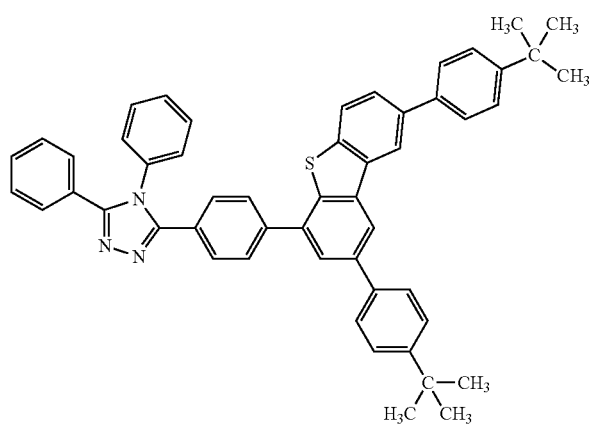
(156)
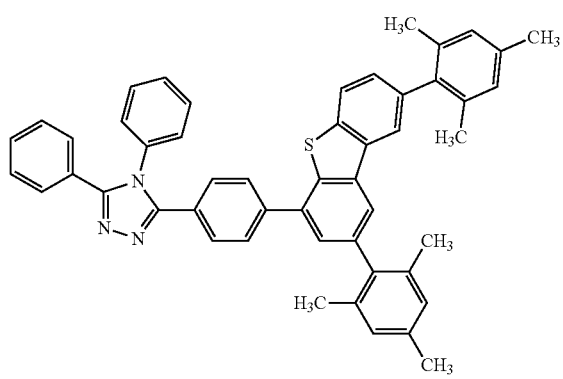
(157)
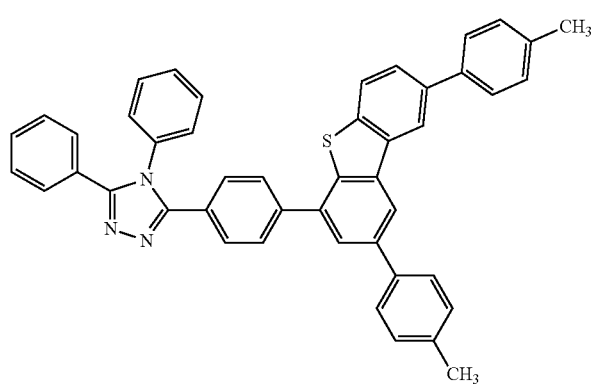
(158)
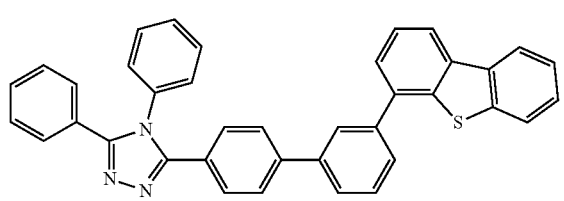
(159)

-continued
(160)
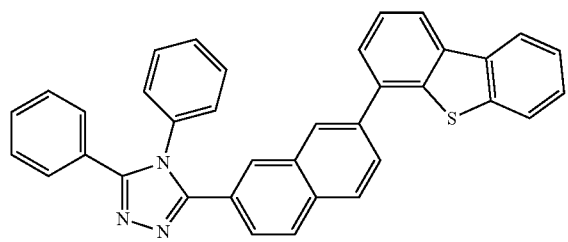
(161)
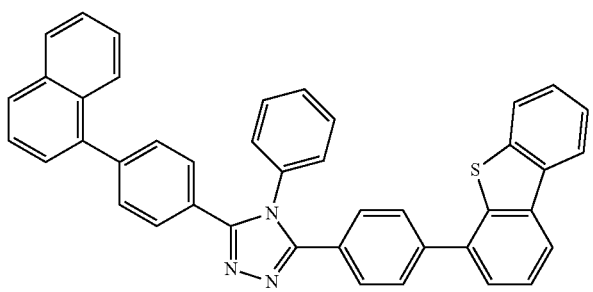
(162)
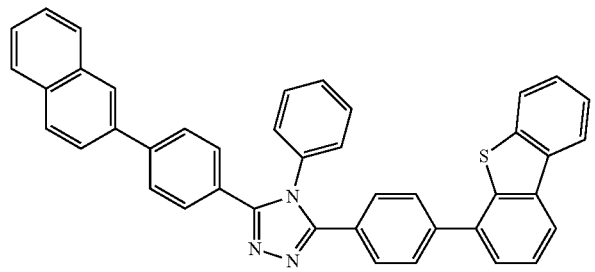
(163)
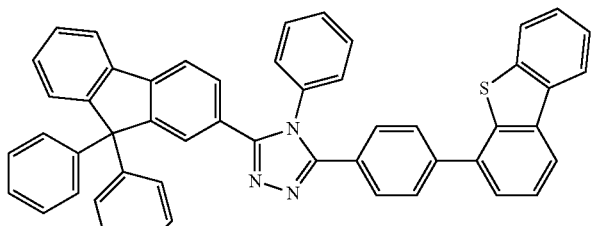
(164)
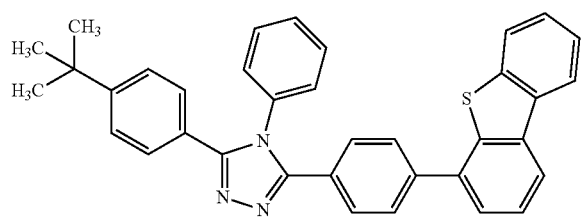
(165)
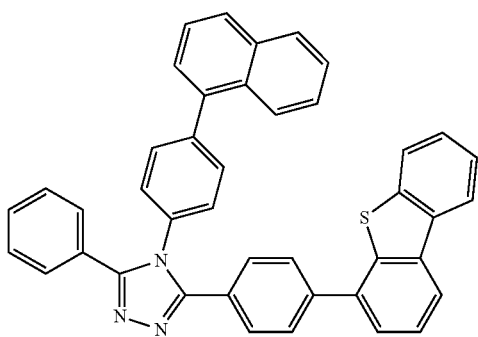
(166)
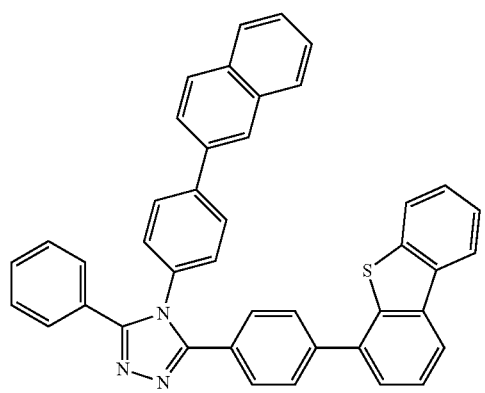
(167)
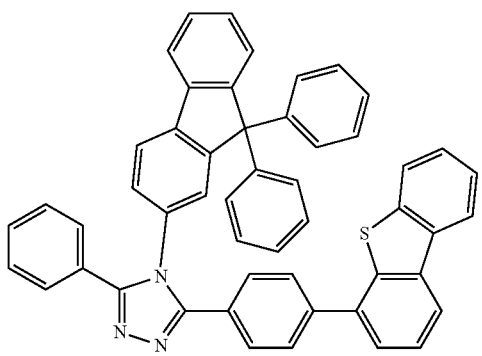
(200)
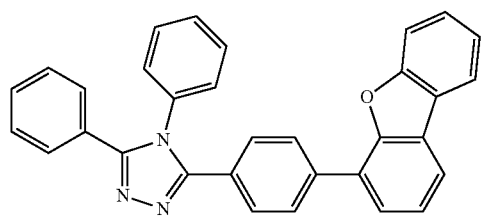
(201)
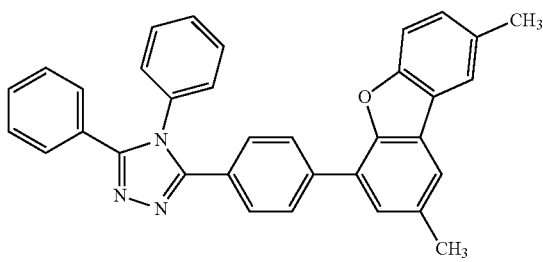

-continued
(202)
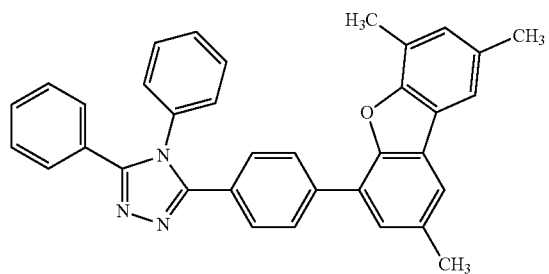
(203)
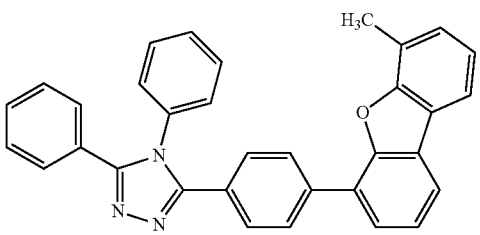
(204)
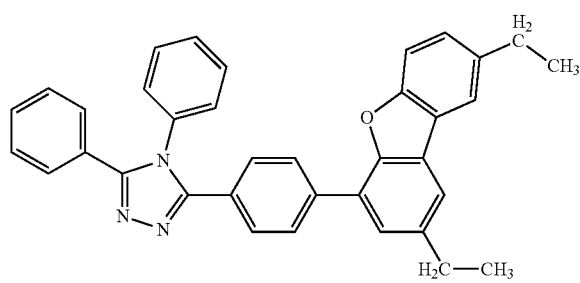
(205)
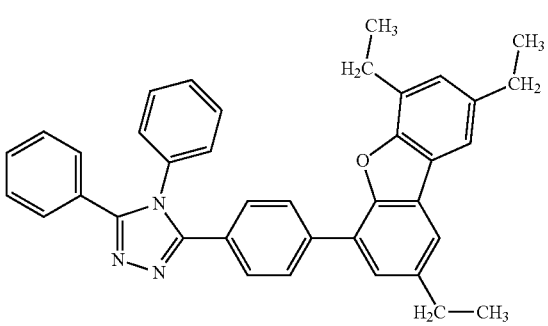
(206)
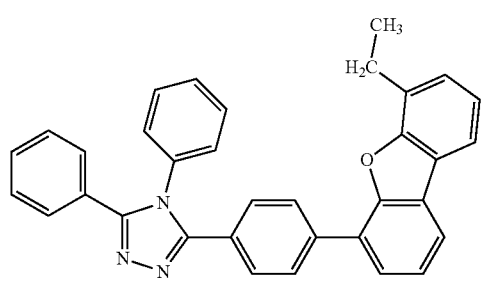
(207)
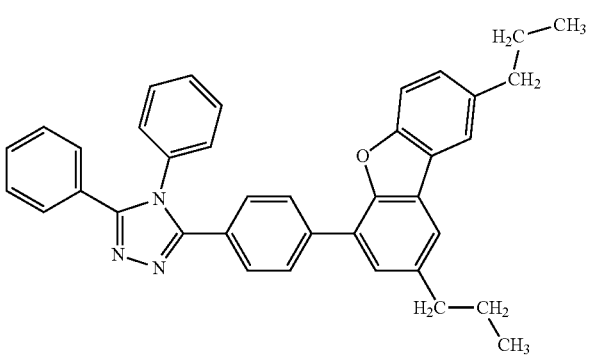
(208)
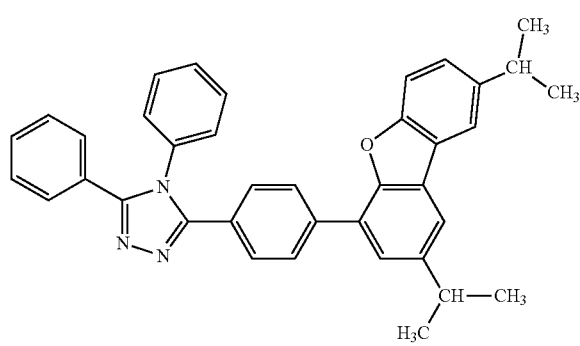
(209)
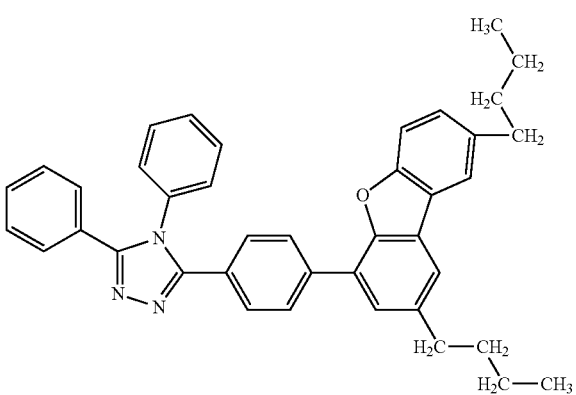

-continued
(210)
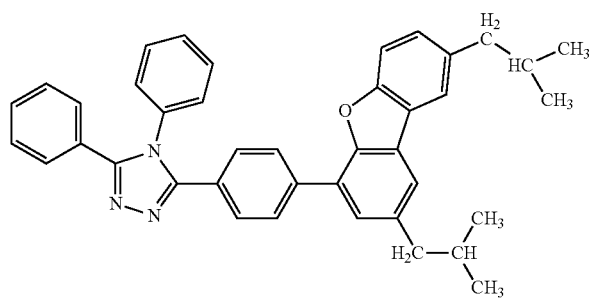
(211)
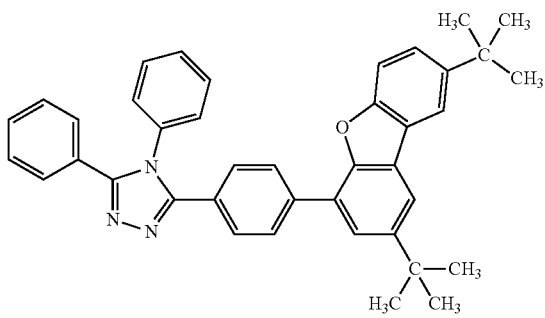
(212)
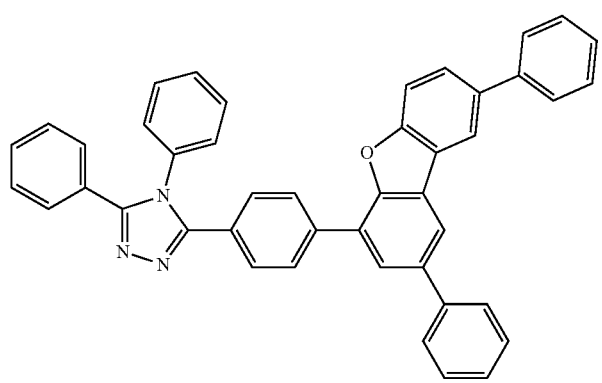
(213)
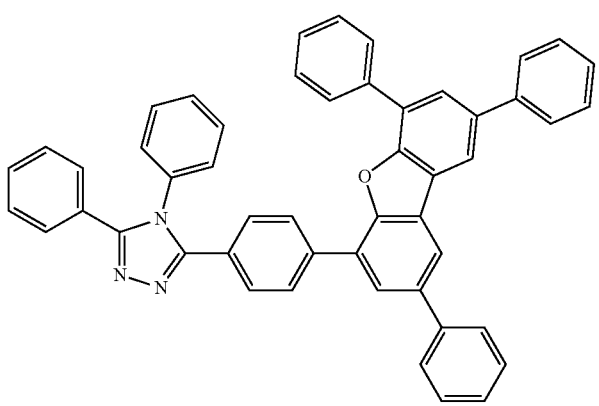
(214)
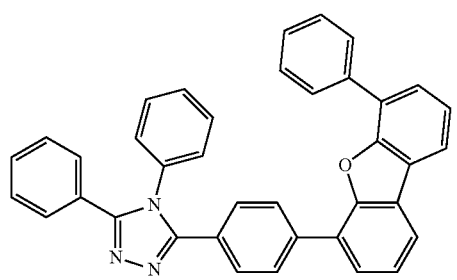
(215)
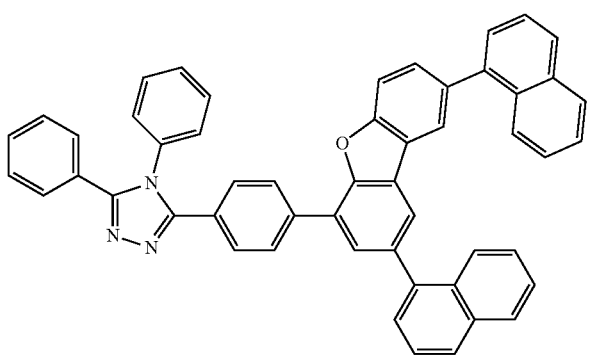
(216)
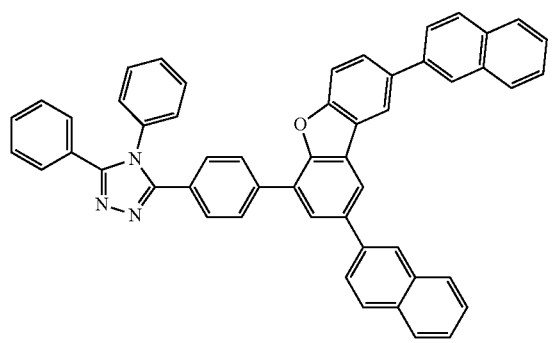
(217)
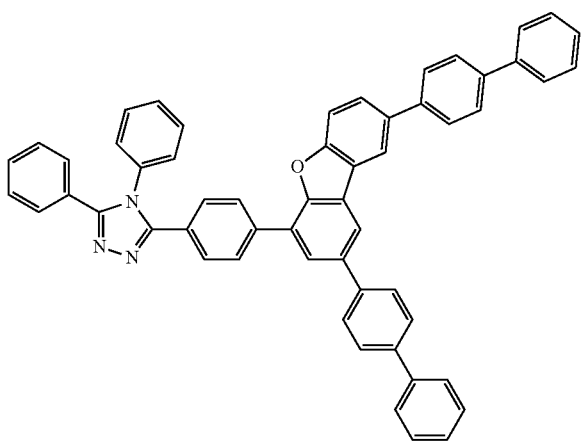

-continued
(218)
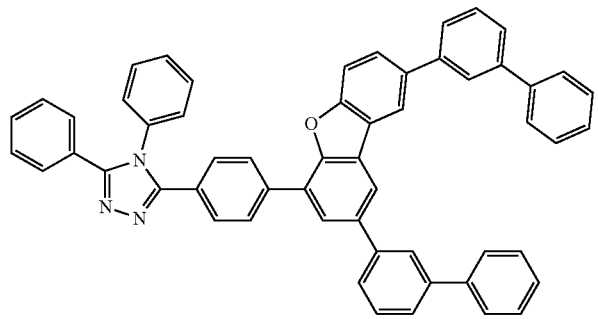
(219)
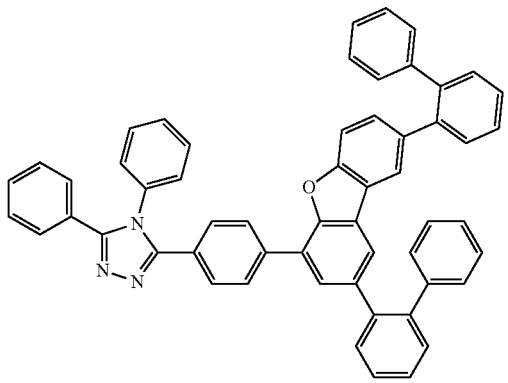
(220)
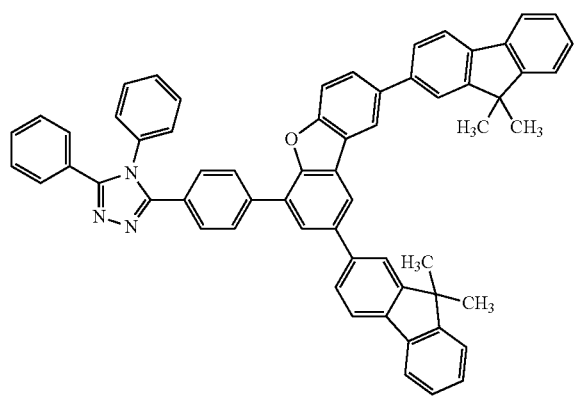
(221)
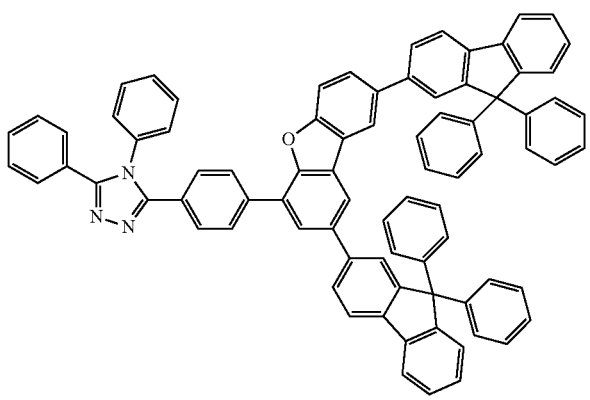
(222)
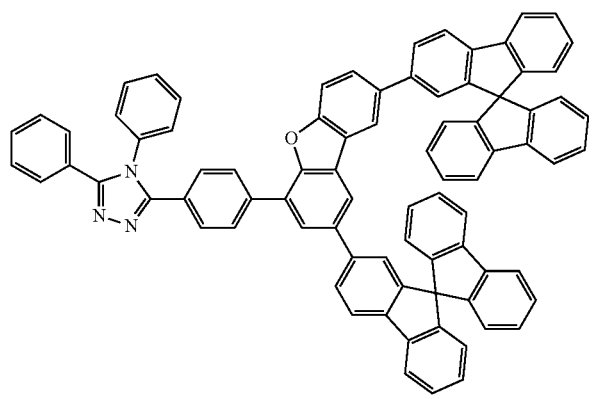
(223)
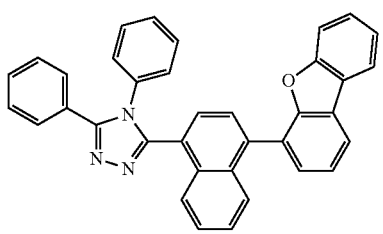
(224)
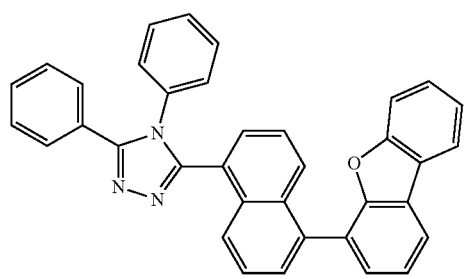
(225)
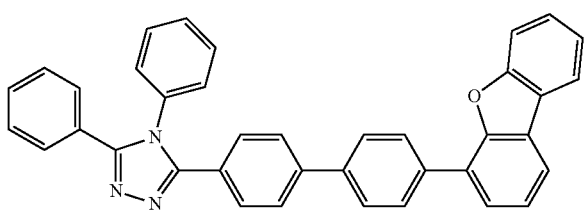

-continued
(226)
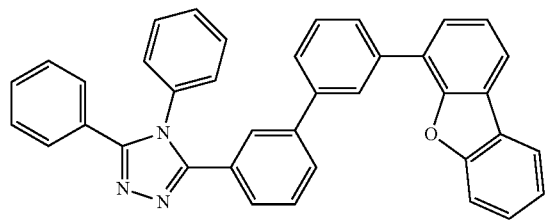
(227)
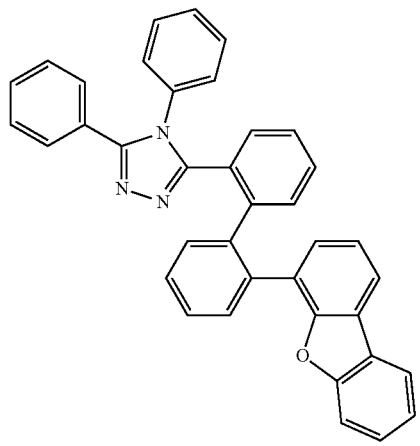
(228)
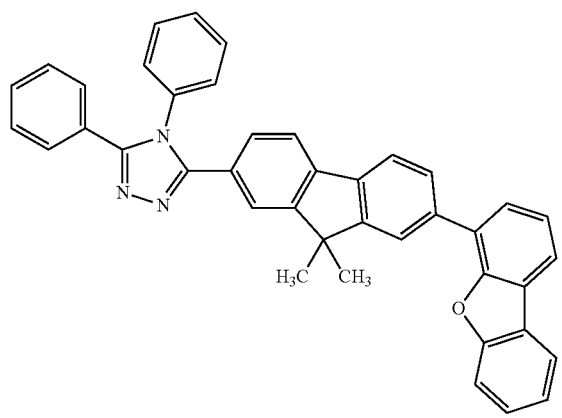
(229)
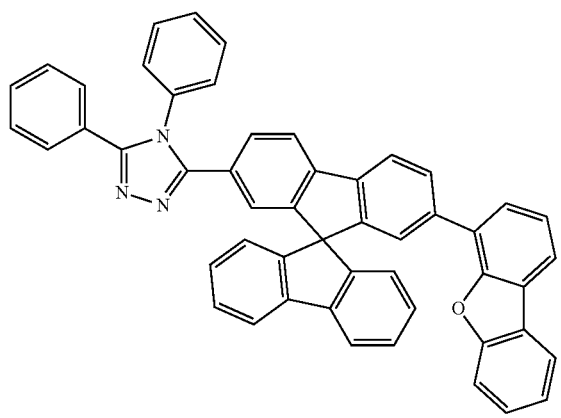
(230)
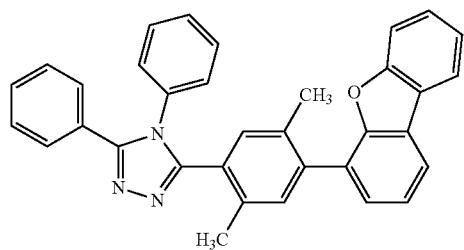
(231)
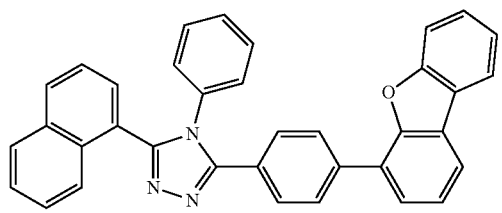
(232)
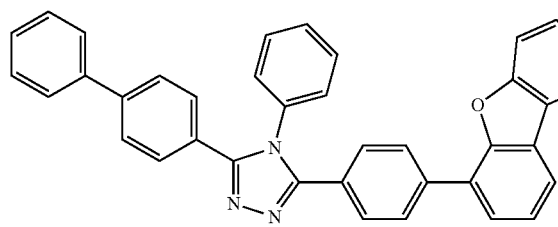
(233)
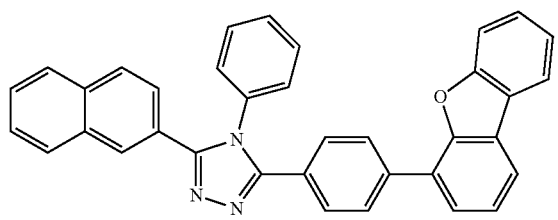

-continued
(234)
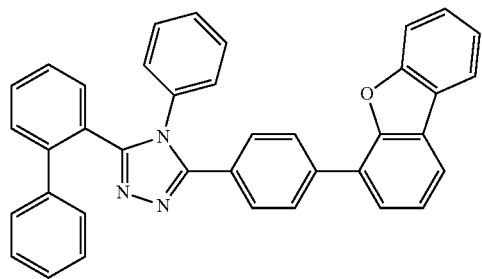
(235)
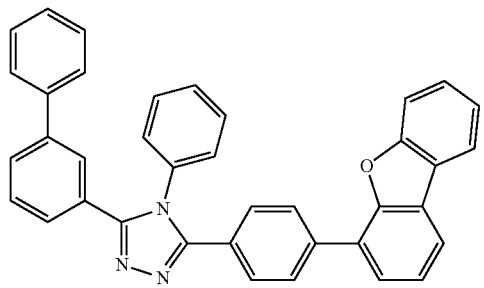
(236)
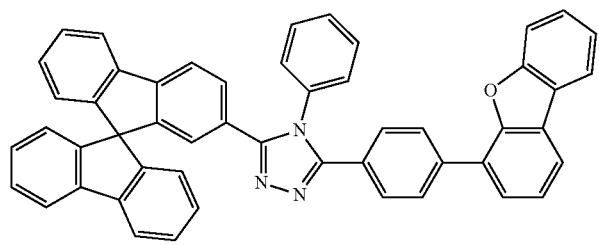
(237)
(238)
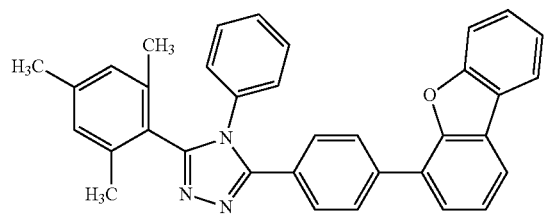
(239)
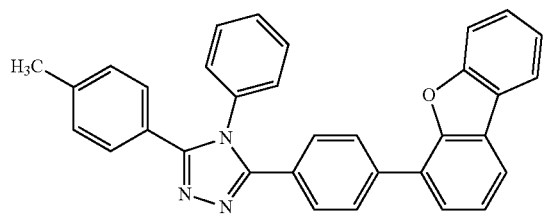
(240)
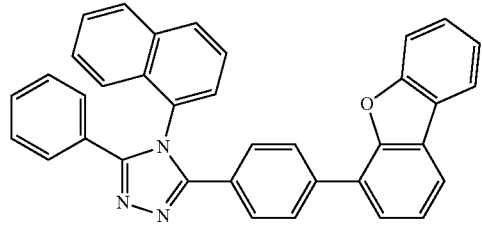
(241)
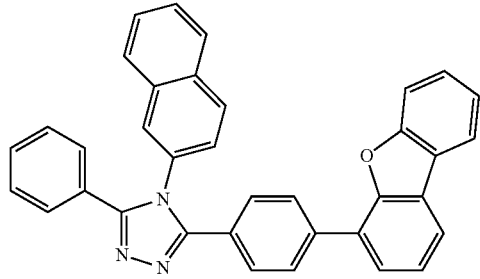
(242)
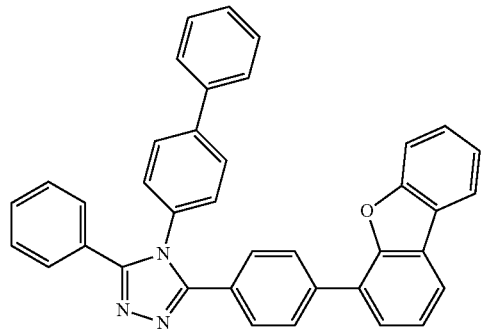
(243)
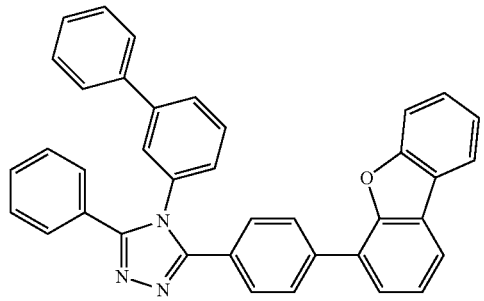

-continued
(244) 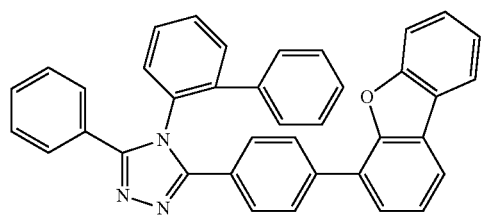
(245) 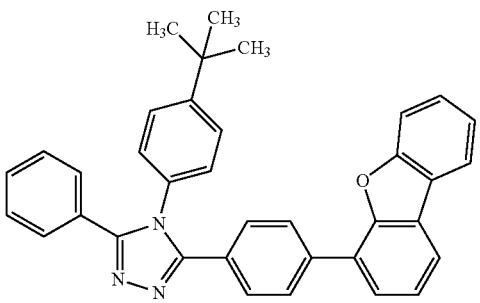
(246) 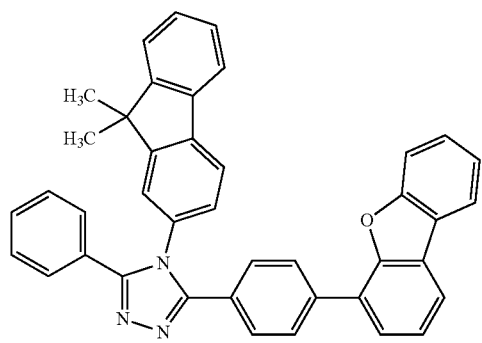
(247) 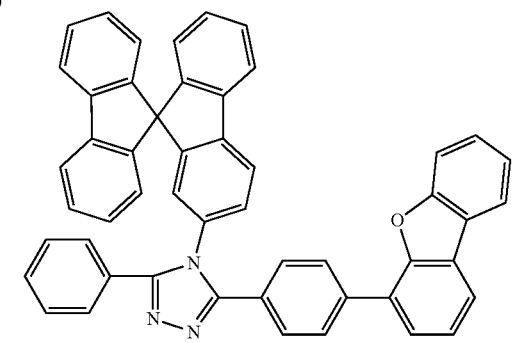
(248) 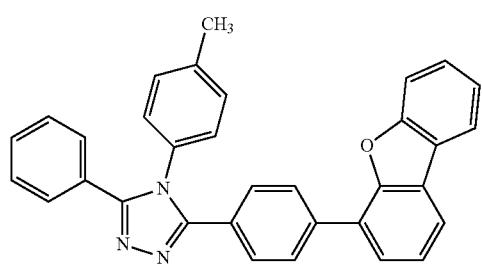
(249) 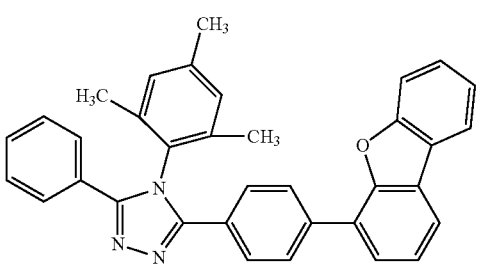
(250) 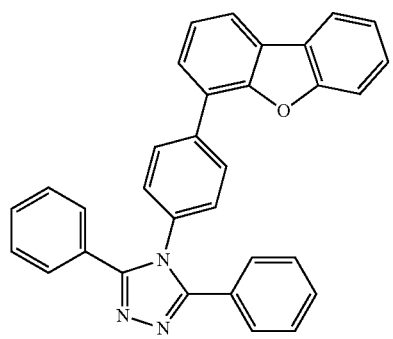
(251) 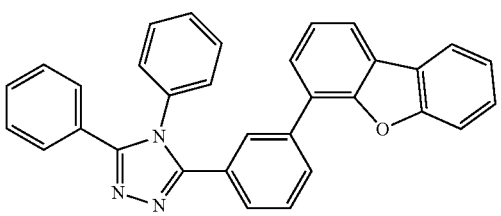

-continued
(252)
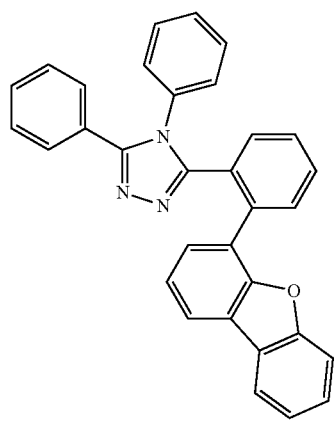
(253)
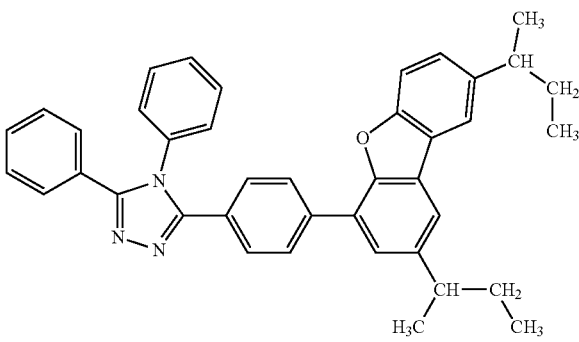
(254)
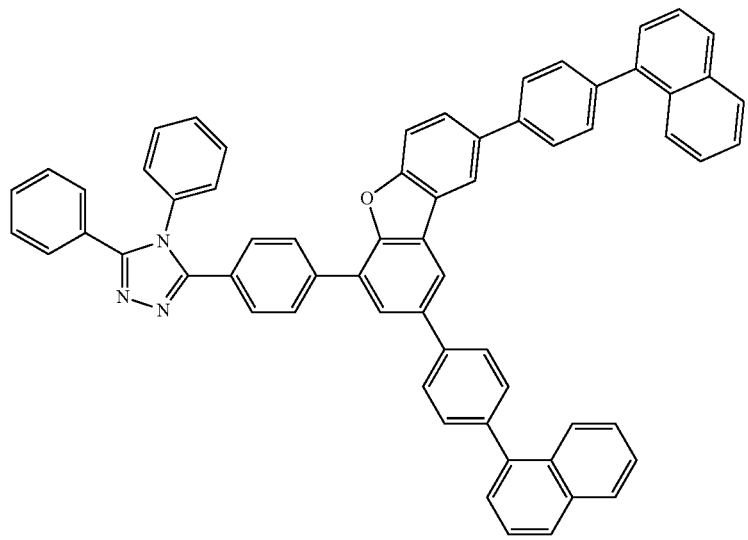
(255)
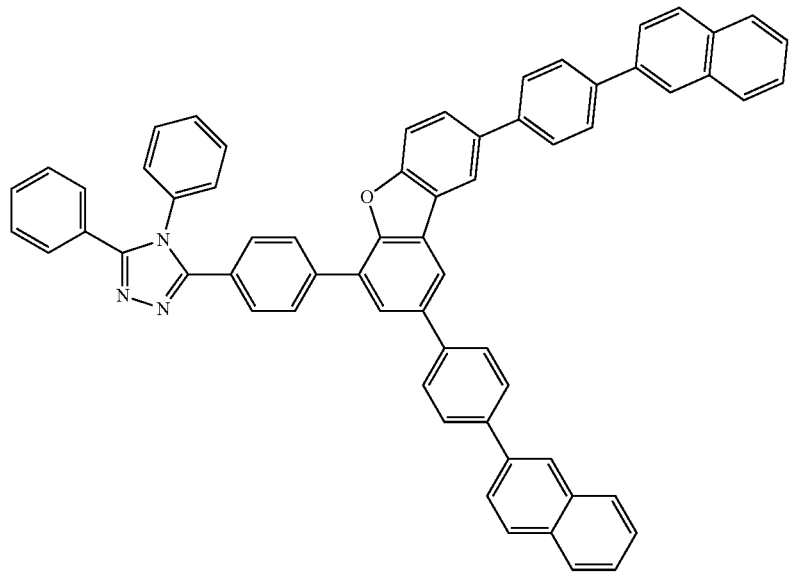

-continued
(256)
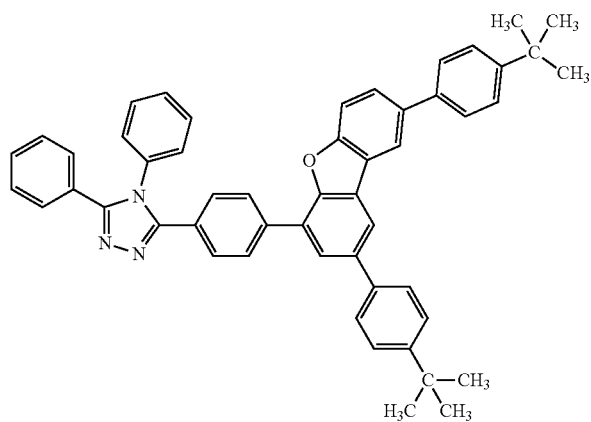
(257)
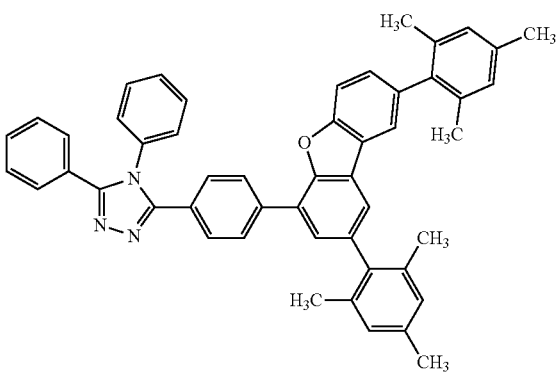
(258)
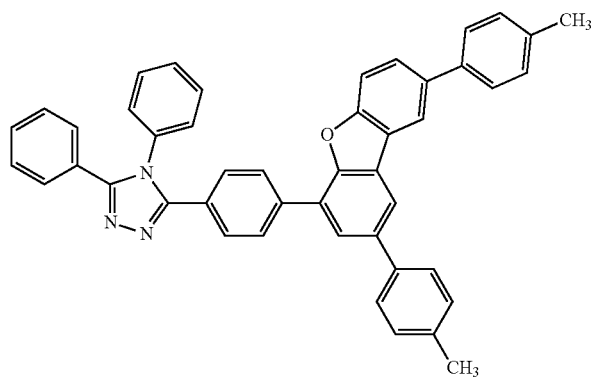
(259)
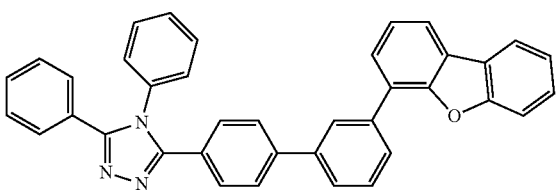
(260)
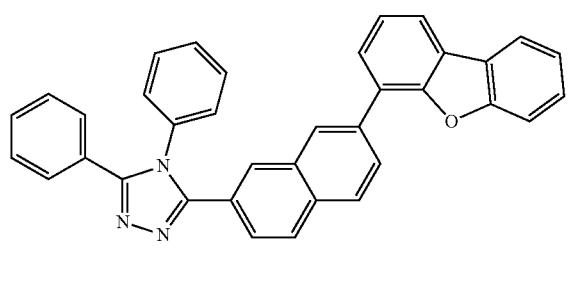
(261)
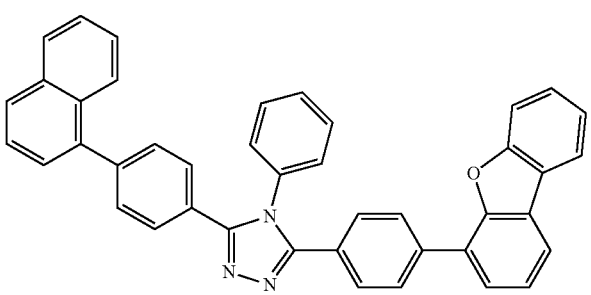
(262)
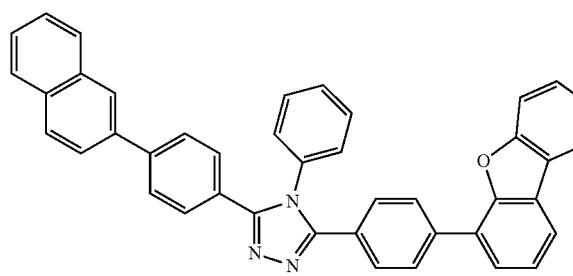
(263)
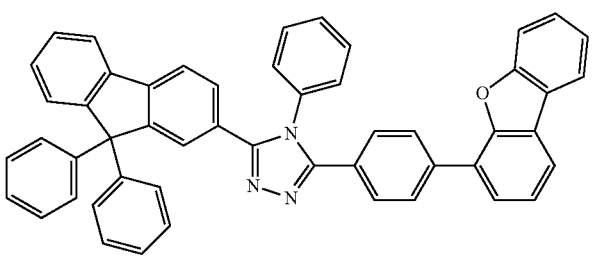

(264)
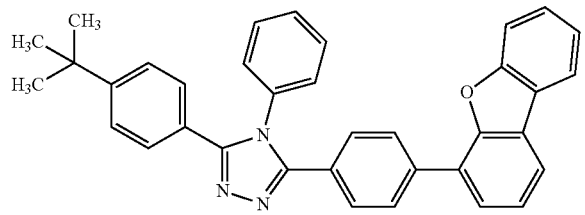

(265)
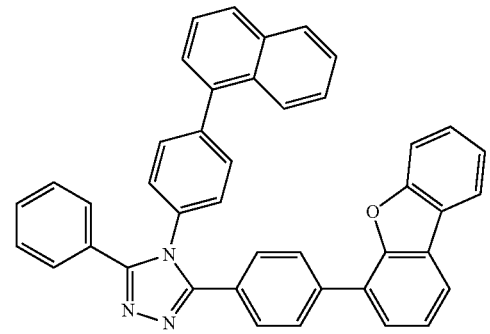

(266)
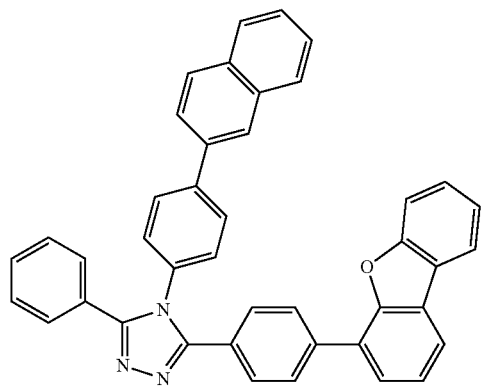

(267)
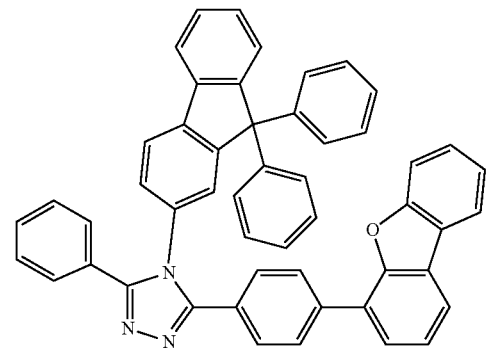

A variety of reactions can be applied to a method of synthesizing a triazole derivative of one embodiment of the present invention. For example, synthesis reactions described below enable the synthesis of a triazole derivative of one embodiment of the present invention. Now, description of methods of synthesizing compounds (G6) and (G7) to be produced is shown below, which are examples of the triazole derivative of one embodiment of the present invention. Note that the methods of synthesizing the triazole derivatives of one embodiment of the present invention are not limited to the synthesis methods described below.

[Method of Synthesizing Triazole Derivative Represented by General Formula (G6)]

First, Synthesis Scheme (A-1) will be illustrated below.

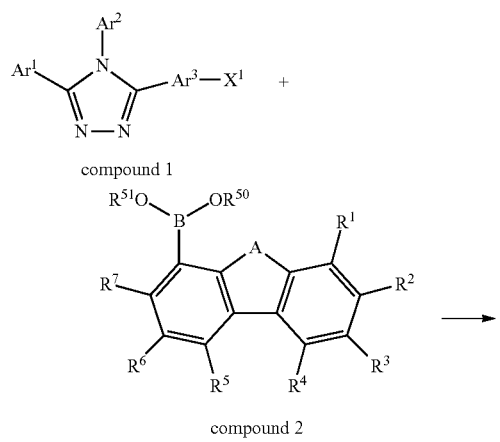

(A-1)

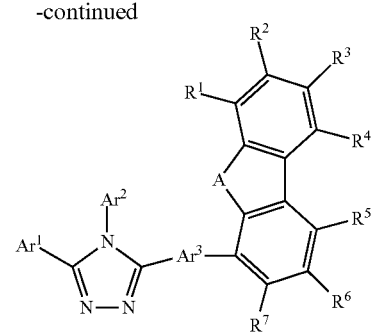

target compound (G6)

The triazole derivative (G6) of one embodiment of the present invention can be synthesized as illustrated in Synthesis Scheme (A-1). Specifically, a halide of a 4H-triazole derivative or a triazole derivative that has a triflate group as a substituent (Compound 1) is coupled with an organoboron compound or boronic acid of a dibenzofuran derivative or a dibenzothiophene derivative (Compound 2) by a Suzuki-Miyaura reaction, whereby the compound (G6) to be produced can be obtained.

In Synthesis Scheme (A-1), A represents oxygen or sulfur, and $R^1$ to $R^7$ separately represent hydrogen, an alkyl group having 1 to 4 carbon atoms, or a substituted or unsubstituted aryl group having 6 to 13 carbon atoms. Further, $R^{50}$ and $R^{51}$ separately represent hydrogen or an alkyl group having 1 to 6 carbon atoms, $Ar^1$ and $Ar^2$ separately represent a substituted or unsubstituted aryl group having 6 to 13 carbon atoms, and $Ar^3$ represents a substituted or unsubstituted arylene group having 6 to 13 carbon atoms. In Synthesis Scheme (A-1), $R^{50}$ and R$^{51}$ may be bonded to each other to form a ring. Furthermore, X$^1$ represents a halogen or a triflate.

Examples of the palladium catalyst that can be used in Synthesis Scheme (A-1) include, but are not limited to, palladium(II) acetate, tetrakis(triphenylphosphine)palladium (0), bis(triphenylphosphine)palladium(II) dichloride, and the like. Examples of the ligand of the palladium catalyst which can be used in Synthesis Scheme (A-1) include, but are not limited to, tri(ortho-tolyl)phosphine, triphenylphosphine, tricyclohexylphosphine, and the like.

Examples of the base that can be used in Synthesis Scheme (A-1) include, but are not limited to, organic bases such as sodium tert-butoxide, inorganic bases such as potassium carbonate and sodium carbonate, and the like.

Examples of the solvent that can be used in Synthesis Scheme (A-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is more preferable to use a mixed solvent of toluene and water, a mixed solvent of toluene, ethanol, and water, or a mixed solvent of water and an ether such as ethylene glycol dimethyl ether.

As a coupling reaction illustrated in Synthesis Scheme (A-1), the Suzuki-Miyaura reaction using the organoboron compound or the boronic acid represented by Compound 2 may be replaced with a cross coupling reaction using an organoaluminum compound, an organozirconium compound, an organozinc compound, an organotin compound, or the like. However, the present invention is not limited thereto.

Further, in the Suzuki-Miyaura Coupling Reaction illustrated in Synthesis Scheme (A-1), an organoboron compound or boronic acid of a 4H-triazole derivative may be coupled with a halide of a dibenzofuran derivative, or a dibenzothiophene derivative or with a carbazole derivative, a dibenzofuran derivative, or a dibenzothiophene derivative which has a triflate group as a substituent, by the Suzuki-Miyaura reaction.

In the above manner, the triazole derivative of this embodiment can be synthesized.

[Method of Synthesizing Triazole Derivative Represented by General Formula (G7)]

First, Synthesis Scheme (B-1) will be illustrated below.

(B-1)

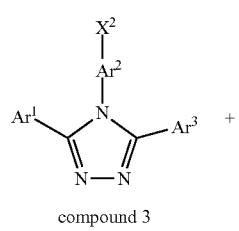

compound 3

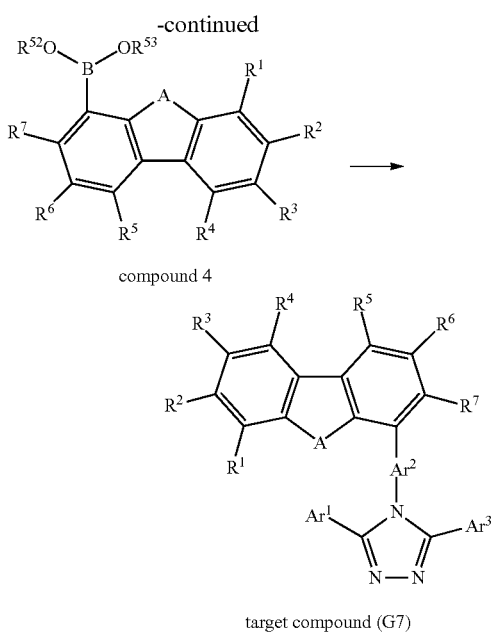

compound 4 target compound (G7)

As illustrated in Synthesis Scheme (B-1), a halide of a 4H-triazole derivative or a triazole derivative that has a triflate group as a substituent (Compound 3) is coupled with an organoboron compound or boronic acid of a dibenzofuran derivative or a dibenzothiophene derivative (Compound 4) by a Suzuki-Miyaura reaction, whereby the compound (G7) to be produced can be obtained.

In Synthesis Scheme (B-1), A represents oxygen or sulfur, and R$^1$ to R$^7$ separately represent hydrogen, an alkyl group having 1 to 4 carbon atoms, or a substituted or unsubstituted aryl group having 6 to 13 carbon atoms. Further, R$^{52}$ and R$^{53}$ separately represent hydrogen or an alkyl group having 1 to 6 carbon atoms, Ar$^1$ and Ar$^3$ separately represent a substituted or unsubstituted aryl group having 6 to 13 carbon atoms, and Ar$^2$ represents a substituted or unsubstituted arylene group having 6 to 13 carbon atoms. In Synthesis Scheme (B-1), R$^{52}$ and R$^{53}$ may be bonded to each other to form a ring. Furthermore, X$^2$ represents a halogen or a triflate.

Examples of the palladium catalyst that can be used in Synthesis Scheme (B-1) include, but are not limited to, palladium(II) acetate, tetrakis(triphenylphosphine)palladium (0), bis(triphenylphosphine)palladium(II) dichloride, and the like. Examples of the ligand of the palladium catalyst which can be used in Synthesis Scheme (B-1) include, but are not limited to, tri(ortho-tolyl)phosphine, triphenylphosphine, tricyclohexylphosphine, and the like.

Examples of the base that can be used in Synthesis Scheme (B-1) include, but are not limited to, organic bases such as sodium tert-butoxide, inorganic bases such as potassium carbonate and sodium carbonate, and the like.

Examples of the solvent that can be used in Synthesis Scheme (B-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is more preferable to use a mixed solvent of toluene and water, a mixed solvent of toluene, ethanol, and water, or a mixed solvent of water and an ether such as ethylene glycol dimethyl ether.

As a coupling reaction illustrated in Synthesis Scheme (B-1), the Suzuki-Miyaura reaction using the organoboron compound or the boronic acid represented by Compound 4 may be replaced with a cross coupling reaction using an organoaluminum compound, an organozirconium compound, an organozinc compound, an organotin compound, or the like. However, the present invention is not limited thereto.

Further, in the Suzuki-Miyaura Coupling Reaction illustrated in Synthesis Scheme (B-1), an organoboron compound or boronic acid of a 4H-triazole derivative may be coupled with a halide of a dibenzofuran derivative, or a dibenzothiophene derivative or with a carbazole derivative, a dibenzofuran derivative, or a dibenzothiophene derivative which has a triflate group as a substituent, by the Suzuki-Miyaura reaction.

By the above-described method, the triazole derivative of this embodiment can be synthesized.

A triazole derivative of this embodiment has high triplet excitation energy and an electron- and hole-transport properties, and therefore the triazole derivative can be suitably used for a light-emitting element. Because the balance between injected electrons and holes is important in a light-emitting layer of a light-emitting element, a triazole derivative of one embodiment of the present invention is preferably used for a light-emitting layer, in particular. Further, owing to the high triplet excitation energy, a triazole derivative of one embodiment of the present invention can be used for a light-emitting layer in combination with a substance that emits phosphorescence. Even when used for a light-emitting layer in combination with a substance that emits phosphorescence, especially a substance that emits short-wavelength light having an emission peak greater than or equal to 400 nm and less than or equal to 500 nm, a triazole derivative of one embodiment of the present invention is capable of realizing high emission efficiency.

Furthermore, since singlet excitation energy (an energy difference between a ground state and a singlet excited state) is higher than triplet excitation energy, a substance that has high triplet excitation energy also has high singlet excitation energy. Therefore, a triazole derivative of one embodiment of the present invention, which has high triplet excitation energy, is effective also when used for a light-emitting layer in combination with a substance that emits fluorescence.

Further, a triazole derivative of one embodiment of the present invention can be used for a carrier-transport layer in a light-emitting element since the triazole derivative can transport carrier. Owing to the high triplet energy, a triazole derivative of one embodiment of the present invention does not easily allow energy transfer from a light-emitting layer and can realize high emission efficiency even when the triazole derivative is used for a layer in contact with the light-emitting layer.

Embodiment 2

In Embodiment 2, as one embodiment of the present invention, a light-emitting element in which a triazole derivative is used for an EL layer will be described with reference to FIGS. 1A and 1B.

In a light-emitting element of this embodiment, the EL layer having at least a light-emitting layer is interposed between a pair of electrodes. The EL layer may also have a plurality of layers in addition to the light-emitting layer. The plurality of layers is a combination of a layer containing a substance having a high carrier-injection property and a layer containing a substance having a high carrier-transport property which are stacked so that a light-emitting region is formed in a region away from the electrodes, that is, so that carriers recombine in a region away from the electrodes. In this specification, the layer containing a substance having a high carrier-injection or -transport property is also referred to as a functional layer which functions to inject or transport carriers, for example. As a functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes the first electrode 101 formed over a substrate 100, the hole-injection layer 111, the hole-transport layer 112, the light-emitting layer 113, the electron-transport layer 114, and the electron-injection layer 115 which are stacked over the first electrode 101 in this order, and the second electrode 103 provided thereover. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. A flexible substrate may also be used. The flexible substrate is a substrate that can be bent, such as a plastic substrate made of polycarbonate, polyarylate, or polyether sulfone, for example. A film (made of polypropylene, polyester, vinyl, polyvinyl fluoride, vinyl chloride, or the like), an inorganic film formed by evaporation, or the like can also be used. Note that materials other than these can be used as long as they can function as a support of the light-emitting element.

For the first electrode 101, any of metals, alloys, electrically conductive compounds, mixtures thereof, and the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering; however, a sol-gel method or the like may also be applied. For example, an IZO film can be formed by a sputtering method using a target obtained by adding 1 wt % to 20 wt % of zinc oxide to indium oxide. An IWZO film can be formed by a sputtering method using a target obtained by adding 0.5 wt % to 5 wt % of tungsten oxide and 0.1 wt % to 1 wt % of zinc oxide to indium oxide. Other examples for materials of the first electrode 101 are gold, platinum, nickel, tungsten, chromium, molybdenum, iron, cobalt, copper, palladium, nitrides of metal materials (e.g., titanium nitride), and the like.

When a layer included in the EL layer 102 which is formed in contact with the first electrode 101 is formed using a later described composite material in which an organic compound and an electron acceptor (acceptor) are mixed, the first electrode 101 can be formed using any of various types of metals, alloys, and electrically-conductive compounds, a mixture thereof, and the like regardless of the work function. For example, aluminum, silver, an alloy containing aluminum (e.g., Al—Si), or the like can be used.

The EL layer 102 formed over the first electrode 101 has at least the light-emitting layer 113 and includes a triazole derivative which is one embodiment of the present invention. The EL layer 102 can also include a known substance as a part, which can be either a low molecular compound or a high molecular compound. Note that substances forming the EL layer 102 may consist of organic compounds or may include an inorganic compound as a part.

Figure 1B:
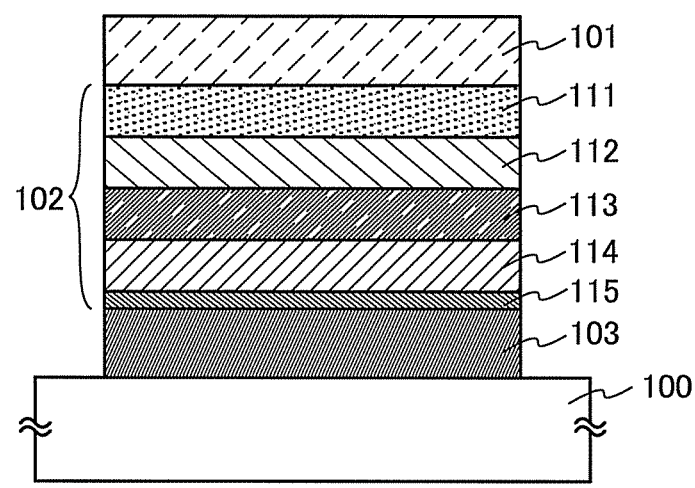

As illustrated in FIGS. 1A and 1B, the EL layer 102 is formed by stacking as appropriate the hole-injection layer 111, the hole-transport layer 112, the electron-transport layer 114, the electron-injection layer 115, and the like in combination in addition to the light-emitting layer 113.

The hole-injection layer 111 is a layer containing a substance having a high hole-injection property. Examples of applicable substances having a high hole-injection property are metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Other examples of applicable substances are phthalocyanine-based compounds such as phthalocyanine (abbreviation: $H_2Pc$) and copper(II) phthalocyanine (abbreviation: CuPc).

Other examples of applicable substances are aromatic amine compounds which are low molecular organic compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methyl-phenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of applicable substances are high molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the hole-injection layer 111, the composite material in which an organic compound and an electron acceptor (acceptor) are mixed may be used. Such a composite material, in which holes are generated in the organic compound by the electron acceptor, has excellent hole injection and transport properties. The organic compound here is preferably a material excellent in transporting the generated holes (a substance having a high hole-transport property).

Examples of the organic compound used for the composite material are a variety of compounds such as aromatic amine compounds, carbazole derivatives, aromatic hydrocarbons, and high molecular compounds (e.g., oligomers, dendrimers, and polymers), and preferably organic compounds having a high hole-transport property, and specifically preferably substances having a hole mobility of $10^{-6}$ cm$^2$/Vs or more. Note that other than these substances, any substance that has a property of transporting more holes than electrons may be used. The organic compounds which can be used for the composite material will be specifically described below.

Examples of the organic compound that can be used for the composite material are aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Other examples of the organic compound that can be used are aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, and 9,10-bis[2-(1-naphthyl)phenyl]anthracene.

Other examples of the organic compound that can be used are aromatic hydrocarbon compounds such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor are organic compounds such as 7,7,8,8-tetracyano-2,3,5,6-tetrafluoroquinodimethane (abbreviation: $F_4$-TCNQ) and chloranil, transition metal oxides, and oxides of metals that belong to Groups 4 to 8 in the periodic table. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air and its hygroscopic property is low and is easily treated.

The composite material may be formed using the above-described electron acceptor and the above-described high molecular compound such as PVK, PVTPA, PTPDMA, or Poly-TPD and used for the hole-injection layer 111.

The hole-transport layer 112 is a layer that contains a substance having a high hole-transport property. Examples of the substance having a high hole-transport property are aromatic amine compounds such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances that have a hole mobility of $10^{-6}$ cm$^2$/Vs or more. Note that other than the above substances, any substance that has a property of transporting more holes than electrons may be used. Further, the layer including a substance having a high hole-transport property is not limited to a single layer, and may be a stack of two or more layers containing any of the above substances.

For the hole-transport layer 112, a carbazole derivative such as CBP, CzPA, or PCzPA or an anthracene derivative such as t-BuDNA, DNA, or DPAnth may be used.

For the hole-transport layer 112, a high molecular compound such as PVK, PVTPA, PTPDMA, or Poly-TPD can be used.

The light-emitting layer 113 is a layer including a light-emitting substance. Note that in Embodiment 2, the case where a triazole derivative of one embodiment of the present invention described in Embodiment 1 is used for the light-emitting layer is described. A triazole derivative of one embodiment of the present invention has high triplet excitation energy and high singlet excitation energy. Therefore, for the light-emitting layer in which a light-emitting substance (a guest material) is dispersed in another substance (a host material), a triazole derivative of one embodiment of the present invention is particularly preferably used as the host material. By using a triazole derivative of one embodiment of the present invention, the light-emitting layer 113 can be a light-emitting layer having a high electron-transport property. By dispersing the guest material which is a light-emitting substance in a triazole derivative of one embodiment of the present invention, light emission from the guest material can be obtained.

In addition, more than one kind of substances can be used as the substances (host materials) in which the light-emitting substance (guest material) is dispersed. The light-emitting layer may thus include a second host material in addition to a triazole derivative of one embodiment of the present invention.

As the light-emitting substance, for example, a fluorescent compound, which emits fluorescence, or a phosphorescent compound, which emits phosphorescence, can be used.

In the case of the use of a fluorescent compound, a substance having lower singlet excitation energy than a triazole derivative of one embodiment of the present invention is preferably used. Since a triazole derivative of one embodiment of the present invention has high singlet excitation energy, the fluorescent compound used for the light-emitting layer 113 can be selected from a wide range of materials.

The fluorescent compounds that can be used for the light-emitting layer 113 will be given. Examples of the materials that emits blue light include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. In addition, examples of the materials that emits green light include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of the materials that emits yellow light include rubrene, 5,12-bis(1,1'-biphenyl-4-yl)-6,11-diphenyltetracene (abbreviation: BPT), and the like. Furthermore, examples of the materials that emits red light include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

In the case of the use of a phosphorescent compound, a substance having lower triplet excitation energy than a triazole derivative described in Embodiment 1 is preferably used. Since a triazole derivative described in Embodiment 1 has high triplet excitation energy, the phosphorescent compound used for the light-emitting layer 113 can be selected from a wide range of materials. Even when used for the light-emitting layer 113 in combination with a phosphorescent compound that emits short-wavelength light having an emission peak greater than or equal to 400 nm and less than or equal to 500 nm (blue light), in particular, a triazole derivative described in Embodiment 1 is capable of realizing high emission efficiency.

The phosphorescent compounds that can be used for the light-emitting layer 113 will be given. Examples of the materials that emits blue light include bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: Ir($CF_3$ ppy)$_2$(pic)), bis[2-(4',6'-difluorophenyl)pyridinato-N,$C^{2'}$]iridium(III) acetylacetonate (abbreviation: FIr(acac)), and the like. Examples of the materials that emits green light include tris(2-phenylpyridinato-N,$C^{2'}$)iridium(III) (abbreviation: Ir(ppy)$_3$), bis(2-phenylpyridinato-N,$C^{2'}$)iridium(III) acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), and the like. Examples of the materials that emits yellow light include bis(2,4-diphenyl-1,3-oxazolato-N,$C^{2'}$)iridium(III) acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), (acetylacetonato)bis{2-(4-methoxyphenyl)-3,5-dimethylpyrazinato}iridium(III) (abbreviation: Ir(dmmoppr)$_2$(acac)), and the like. Examples of the materials that emits orange light include tris(2-phenylquinolinato-N,$C^{2'}$)iridium(III) (abbreviation: Ir(pq)$_3$), bis(2-phenylquinolinato-N,$C^{2'}$)iridium(III) acetylacetonate (abbreviation: Ir(pq)$_2$(acac)), (acetylacetonato)bis(3,5-dimethyl-2-phenylpyrazinato)iridium(III) (abbreviation: Ir(mppr-Me)$_2$(acac)), (acetylacetonato)bis(5-isopropyl-3-methyl-2-phenylpyrazinato)iridium(III) (abbreviation: Ir(mppr-iPr)$_2$(acac)), and the like. Examples of the materials that emits red light include organometallic complexes such as bis[2-(2'-benzo[4,5-α]thienyl)pyridinato-N,$C^{3'}$)iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac), (acetylacetonato)bis[2,3-bis(4-fluorophenyl)quinoxalinato]iridium(III) (abbreviation: Ir(Fdpq)$_2$(acac)), acetylacetonato)bis(2,3,5-triphenylpyrazinato)iridium(III) (abbreviation: Ir(tppr)$_2$(acac)), (dipivaloylmethanato)bis(2,3,5-triphenylpyrazinato)iridium(III) (abbreviation: Ir(tppr)$_2$(dpm)), and (2,3,7,8,12,13,17,18-octaethyl-21H,23H-porphine)platinum(II) (abbreviation: PtOEP). Any of the following rare-earth metal complexes can be used as a phosphorescent compound: tris(acetylacetonato)(monophenanthroline)terbium(III) (abbreviation: [Tb(acac)$_3$ (Phen)); tris(1,3-diphenyl-1,3-propanedionato)(monophenanthroline)europium(III) (abbreviation: [Eu(DBM)$_3$(Phen)); and tris[1-(2-thenoyl)-3,3,3-trifluoroacetonato](monophenanthroline)europium(III) (abbreviation: [Eu(TTA)$_3$(Phen)), because their light emission is from a rare-earth metal ion (electronic transition between different multiplicities) in such a rare-earth metal complex.

As the light-emitting substance, a high molecular compound can be used. Specifically, examples of the materials that emits blue light include poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. Further, examples of the materials that emits green light include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenefluorenylene)-alt-co-(2-m ethoxy-5-(2-ethylhexyloxy)-1,4-phenylene)], and the like. Furthermore, examples of the materials that emits orange to red light include poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like The electron-transport layer 114 is a layer including a substance having a high electron-transport property. A triazole derivative of one embodiment of the present invention described in Embodiment 1 can be suitably used for the electron-transport layer 114, since the triazole derivative has an excellent electron-transport property. When a triazole derivative of one embodiment of the present invention is used for the electron-transport layer 114, the host material of the light-emitting layer is not limited to a triazole derivative of one embodiment of the present invention and may be any other material.

As the substance having a high electron-transport property, the following metal complexes having a quinoline skeleton or a benzoquinoline skeleton can be given: tris(8-quinolinolato)aluminum (abbreviation: Alq); tris(4-methyl-8-quinolinolato)aluminum (abbreviation: Almq$_3$); bis(10-hydroxybenzo[h]-quinolinato)beryllium (abbreviation: BeBq$_2$); and bis(2-methyl-8-quinolinolato)(4-phenylphenolato)aluminum (abbreviation: BAlq). A metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can also be used. Other than metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances described here are mainly materials having an electron mobility of $10^{-6}$ cm$^2$/Vs or more. Further, the electron-transport layer is not limited to a single layer, and may be a stack of two or more layers containing any of the above substances are stacked.

The electron-injection layer 115 is a layer that contains a substance having a high electron-injection property. Examples of the substance that can be used for the electron-injection layer 115 are alkali metals, alkaline earth-metals, and compounds thereof, such as lithium, cesium, calcium, lithium fluoride, cesium fluoride, calcium fluoride, and lithium oxide, rare earth-metal compounds such as erbium fluoride, and the above-mentioned substances for forming the electron-transport layer 114.

Alternatively, a composite material in which an organic compound and an electron donor (donor) are mixed may be used for the electron-injection layer 115. Such a composite material, in which electrons are generated in the organic compound by the electron donor, has excellent electron injection and transport properties. The organic compound here is preferably a material excellent in transporting the generated electrons, as which specifically any of the above substances (such as metal complexes and heteroaromatic compounds) for the electron-transport layer 114 can be used. The electron donor can be a substance exhibiting an electron-donating property for the organic compound. Specific examples of the electron donor are alkali metals, alkaline-earth-metals, and rare earth-metals, such as lithium, cesium, magnesium, calcium, erbium, and ytterbium. Any of alkali metal oxides and alkaline-earth-metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method such as an evaporation method (e.g., a vacuum evaporation method), an inkjet method, or a coating method.

When the second electrode 103 functions as a cathode, any of metals, alloys, electrically conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium and cesium, alkaline earth-metals such as magnesium, calcium, and strontium, alloys thereof (e.g., Mg—Ag and Al—Li), rare earth-metals such as europium and ytterbium, alloys thereof, aluminum, silver, and the like.

When a layer included in the EL layer 102 which is formed in contact with the second electrode 103 is formed using the composite material in which the organic compound and the electron donor (donor), which are described above, are mixed, a variety of conductive materials such as aluminum, silver, ITO, and indium oxide-tin oxide containing silicon or silicon oxide can be used regardless of the work function.

Note that the second electrode 103 can be formed by a vacuum evaporation method or a sputtering method. In the case of using a silver paste or the like, a coating method, an inkjet method, or the like can be used.

In the above-described light-emitting element, a current flows due to a potential difference generated between the first electrode 101 and the second electrode 103 and holes and electrons recombine in the EL layer 102, whereby light is emitted. Then, this emitted light is extracted outside through one or both of the first electrode 101 and the second electrode 103. Therefore, one or both of the first electrode 101 and the second electrode 103 are electrodes having a property of transmitting visible light.

Further, the structure of the layers provided between the first electrode 101 and the second electrode 103 is not limited to the above described structure. A structure other than the above may alternatively be employed as long as a light-emitting region in which holes and electrons recombine is provided in a portion away from the first electrode 101 and the second electrode 103 in order to prevent quenching due to proximity of the light-emitting region to metal.

In other words, there is no particular limitation on a stack structure of the layers. A layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer including a triazole derivative of one embodiment of the present invention described in Embodiment 1 as a host material.

In the light-emitting element illustrated in FIG. 1B, the EL layer 102 is provided between the first electrode 101 and the second electrode 103 over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 serving as a cathode over the substrate 100, the electron-injection layer 115, the electron-transport layer 114, the light-emitting layer 113, the hole-transport layer 112, and the hole-injection layer 111 which are stacked over the second electrode 103 in this order, and the first electrode 101 provided thereover which serves as an anode.

A method of forming the light-emitting element will now be specifically described.

In a light-emitting element of this embodiment, the EL layer is interposed between the pair of electrodes. The EL layer has at least the light-emitting layer, and the light-emitting layer is formed using a triazole derivative of one embodiment of the present invention described in Embodiment 1 as a host material. Further, the EL layer may include a functional layer (e.g., the hole-injection layer, the hole-transport layer, the electron-transport layer, or the electron-injection layer) in addition to the light-emitting layer. The electrodes (the first electrode and the second electrode), the light-emitting layer, and the functional layer may be formed by any of the wet processes such as a droplet discharging method (an inkjet method), a spin coating method, and a printing method, or by a dry processes such as a vacuum evaporation method, a CVD method, and a sputtering method. A wet process allows formation at atmospheric pressure with a simple device and by a simple process, which gives the effects of simplifying the process and improving productivity. In contrast, a dry process does not need dissolution of a material and enables use of a material that has low solubility in a solution, which expands the range of material choices.

All the thin films included in a light-emitting element may be formed by a wet method. In this case, the light-emitting element can be manufactured with only facilities needed for a wet process. Alternatively, the following method may be employed: formation of the stacked layers up to formation of the light-emitting layer is performed by a wet process whereas the functional layer, the first electrode, and the like which are stacked over the light-emitting layer are formed by a dry process. Further alternatively, the following method may be employed: the second electrode and the functional layer are formed by a dry process before the formation of the light-emitting layer whereas the light-emitting layer, the functional layer stacked thereover, and the first electrode are formed by a wet process. Needless to say, this embodiment is not limited to these, and a light-emitting element can be formed by appropriate selection from a wet method and a dry method depending on a material to be used, necessary film thickness, and the interface state.

In this embodiment, a light-emitting element is fabricated over a substrate made of glass, plastic or the like. By forming a plurality of such light-emitting elements over one substrate, a passive matrix light-emitting device can be manufactured. Further, a light-emitting element may be fabricated in such a manner that a thin film transistor (TFT), for example, is be formed over a substrate made of glass, plastic, or the like and the element is formed over an electrode electrically connected to the TFT. Thus, an active matrix light-emitting device in which the TFT controls the driving of the light-emitting element can be manufactured. Note that there is no particular limitation on the structure of the TFT: a staggered TFT or an inverted staggered TFT may be employed. In addition, there is no particular limitation on the crystallinity of a semiconductor used for the TFT, and an amorphous semiconductor or a crystalline semiconductor may be used. Furthermore, a driver circuit formed over a TFT substrate may be formed with both n-channel TFTs and p-channel TFTs or may be formed with either n-channel TFTs or p-channel TFTs.

A triazole derivative of one embodiment of the present invention described in Embodiment 1 has high triplet excitation energy and an electron- and hole-transport properties. Therefore, by using a triazole derivative of one embodiment of the present invention described in Embodiment 1, a light-emitting element having high emission efficiency and/or low driving voltage can be obtained.

Furthermore, a light-emitting device (such as an image display device) using a light-emitting element of one embodiment of the present invention which is obtained as above can have reduced power consumption.

By use of the light-emitting element described in this embodiment, a passive matrix light-emitting device or an active matrix light-emitting device in which driving of the light-emitting element is controlled by a thin film transistor (TFT) can be manufactured.

This embodiment can be used in appropriate combination with any of the other embodiments.

Embodiment 3

In this embodiment, modes of light-emitting elements having a structure in which a plurality of light-emitting units is stacked (hereinafter, referred to as a stacked-type element) will be described with reference to FIGS. 2A and 2B. These light-emitting element are each a light-emitting element including a plurality of light-emitting units between a first electrode and a second electrode.

Figure 2A:
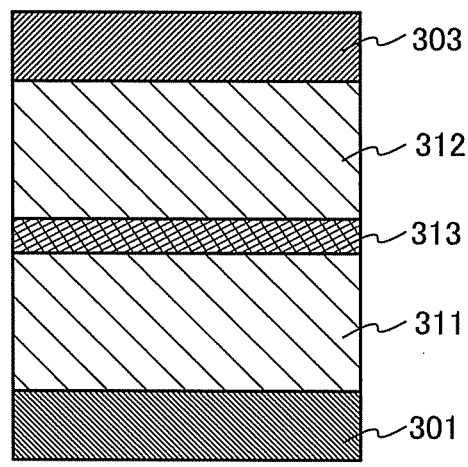
FIGS. 2A and 2B each illustrate a light-emitting element of an embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same or different structures. The first light-emitting unit 311 and the second light-emitting unit 312 may have the same structure as the EL layer of Embodiment 2, or either of the units may differ in structure from the EL layer.

Further, a charge generation layer 313 is provided between the first light-emitting unit 311 and the second light-emitting unit 312. The charge generation layer 313 has a function of injecting electrons into one of the light-emitting units and injecting holes into the other of the light-emitting units when a voltage is applied to the first electrode 301 and the second electrode 303. In the case of this embodiment, when a voltage is applied so that the potential of the first electrode 301 is higher than that of the second electrode 303, the charge generation layer 313 injects electrons into the first light-emitting unit 311 and injects holes into the second light-emitting unit 312.

Note that the charge generation layer 313 preferably has a property of transmitting visible light in terms of light extraction efficiency. Further, the charge generation layer 313 functions even if it has lower conductivity than the first electrode 301 or the second electrode 303.

The charge generation layer 313 may have a structure in which it includes the organic compound having a high hole-transport property and the electron acceptor (acceptor) or a structure in which it includes an organic compound having a high electron-transport property and the electron donor (donor), or may be a stack of both of these structures.

In the case of the structure in which the organic compound having a high hole-transport property and the electron acceptor are included, examples of the substance that can be used as the organic compound having a high hole-transport property are aromatic amine compounds such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any substance that has a property of transporting more holes than electrons may be used.

Examples of the electron acceptor are 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air and its hygroscopic property is low and is easily treated.

In the case of the structure in which the organic compound having a high electron-transport property and the electron donor are included, examples of the organic compound having a high electron-transport property which can be used are: metal complexes having a quinoline skeleton or a benzoquinoline skeleton such as Alq, Almq$_3$, BeBq$_2$, and BAlq; metal complexes having an oxazole-based ligand or a thiazole-based ligand, such as Zn(BOX)$_2$ and Zn(BTZ)$_2$; and the like. Examples other than the metal complexes are PBD, OXD-7, TAZ, BPhen, BCP, and the like. The substances described here are mainly substances having an electron mobility of $10^{-6}$ cm$^2$/Vs or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium, cesium, magnesium, calcium, ytterbium, indium, lithium oxide, cesium carbonate, and the like. An organic compound such as tetrathianaphthacene may be used as the electron donor.

By forming the charge generation layer 313 with any of the above materials, it is possible to suppress an increase in drive voltage caused when the EL layers are stacked.

Figure 2B:
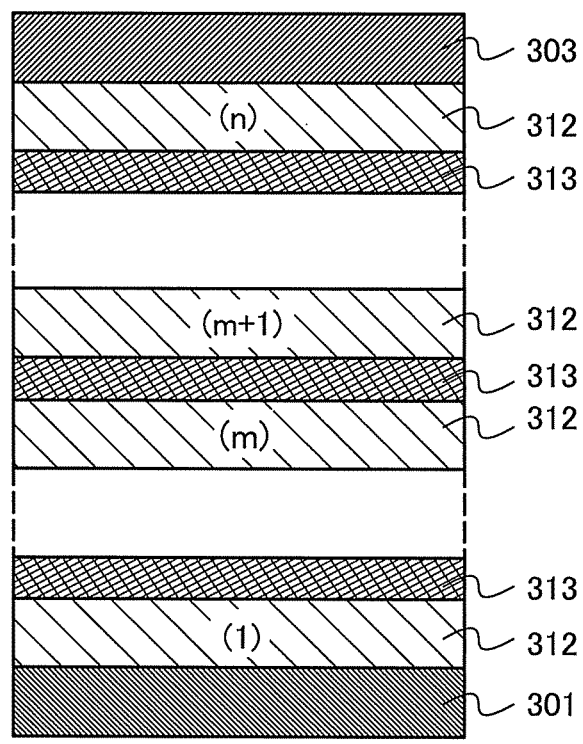

Although the light-emitting element having two light-emitting units is described in this embodiment, the embodiment can be applied to a light-emitting element in which three or more light-emitting units are stacked as illustrated in FIG. 2B. For example, in a stack structure having n layers (n is a natural number greater than or equal to 2), the charge generation layer 313 is interposed between an m-th light-emitting unit and an (m+1)-th light-emitting unit (m is a natural number greater than or equal to 1 and less than or equal to (n−1)). When a plurality of light-emitting units with a charge generation layer interposed therebetween are arranged between a pair of electrodes, as in the light-emitting element of this embodiment, it is possible to realize an element having a long lifetime which can emit light with a high luminance while current density is kept low.

Furthermore, by making emission colors of the light-emitting units different, light having a desired color can be obtained from the light-emitting element as a whole. For example, the emission colors of first and second light-emitting units are complementary in a light-emitting element having the two light-emitting units, whereby the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same can be applied to a light-emitting element having three light-emitting units. For example, the light-emitting element as a whole can emit white light when the emission color of the first light-emitting unit is red, the emission color of the second light-emitting unit is green, and the emission color of the third light-emitting unit is blue.

Note that this embodiment can be combined with any of the other embodiments as appropriate.

Embodiment 4

In Embodiment 4, a light-emitting device having a light-emitting element of one embodiment of the present invention will be described with reference to FIGS. 3A and 3B. Note that FIG. 3A is a top view illustrating the light-emitting device, and FIG. 3B is a cross-sectional view taken along lines A-B and C-D of FIG. 3A.

In FIG. 3A, reference numeral 401 denotes a driver circuit portion (a source driver circuit), reference numeral 402 denotes a pixel portion, and reference numeral 403 denotes a driver circuit portion (a gate driver circuit), which are each indicated by dotted lines. Reference numeral 404 denotes a sealing substrate, reference numeral 405 denotes a sealant, and a portion enclosed by the sealing material 405 is a space 407.

Note that a lead wiring 408 is a wiring for transmitting signals that are to be inputted to the source driver circuit 401 and the gate driver circuit 403, and receives a video signal, a clock signal, a start signal, a reset signal, and the like from an FPC 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. Here, the source driver circuit 401 which is the driver circuit portion and one pixel in the pixel portion 402 are illustrated.

Note that as the source driver circuit 401, a CMOS circuit which includes an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve coverage, the insulator 414 is provided such that either an upper end portion or a lower end portion of the insulator 414 has a curved surface with a curvature. For example, when positive photosensitive acrylic resin is used as a material for the insulator 414, it is preferable that only an upper end portion of the insulator 414 have a curved surface with a radius of curvature (0.2 vim to 3 vim). For the insulator 414, it is also possible to use either a negative type that becomes insoluble in an etchant by light irradiation or a positive type that becomes soluble in an etchant by light irradiation.

A light-emitting layer 416 and a second electrode 417 are formed over the first electrode 413. Here, as a material for forming the first electrode 413 functioning as the anode, a material having a high work function is preferably used. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum and a titanium nitride film, or the like. Note that, when a stacked layer structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes a triazole derivative described in Embodiment 1. Further, another material included in the light-emitting layer 416 may be a low molecular material, an oligomer, a dendrimer, a high molecular material, or the like.

As a material used for the second electrode 417 which is formed over the light-emitting layer 416 and serves as a cathode, it is preferable to use a material having a low work function (e.g., Al, Mg, Li, Ca, or an alloy or a compound thereof such as Mg—Ag, Mg—In, Al—Li, LiF, or $CaF_2$). In order that light generated in the light-emitting layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide (ZnO)) is preferably used for the second electrode 417.

Further, the sealing substrate 404 is attached to the element substrate 410 with the sealing material 405 whereby, a light-emitting element 418 is provided in the space 407 enclosed by the element substrate 410, the sealing substrate 404, and the sealing material 405. The space 407 may be filled with an inert gas (such as nitrogen or argon), or the sealing material 405.

Note that an epoxy-based resin is preferably used as the sealing Material 405. Such a material preferably allows as little moisture and oxygen as possible to penetrate. As a material used for the sealing substrate 404, a plastic substrate formed of FRP (fiberglass-reinforced plastics), PVF (polyvinyl fluoride), polyester, acrylic, or the like can be used other than a glass substrate or a quartz substrate.

As described above, the active matrix light-emitting device having the light-emitting element of one embodiment of the present invention can be obtained.

Figure 4A:
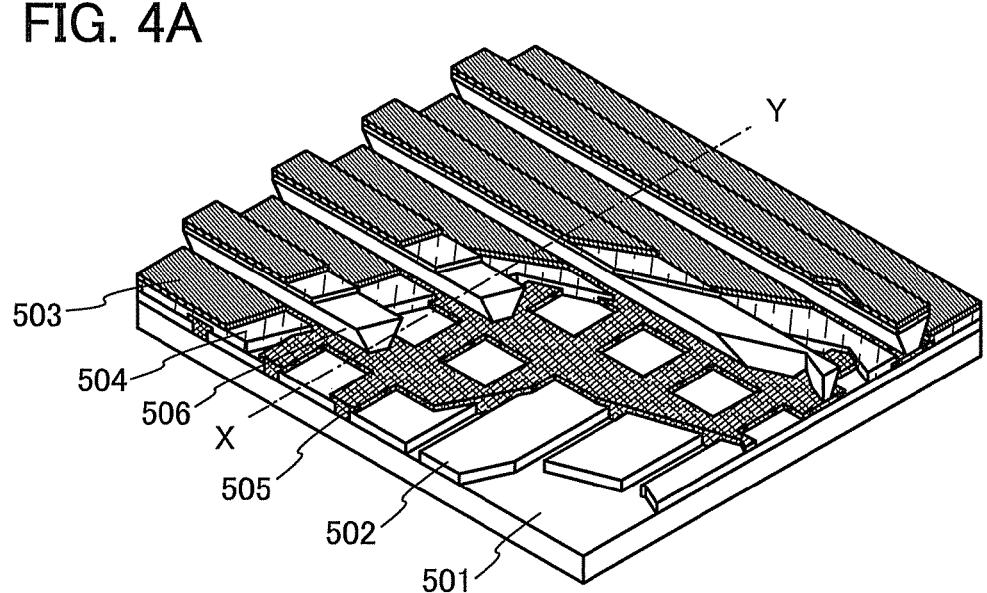
FIGS. 4A and 4B illustrate a light-emitting device according to one embodiment of the present invention.
Figure 4B:
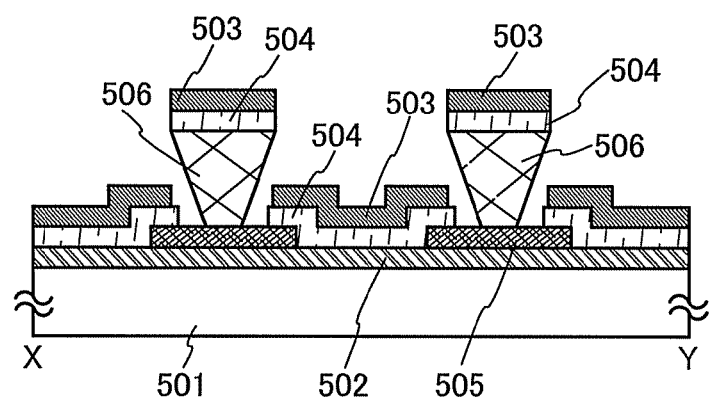

Further, a light-emitting element of one embodiment of the present invention can be used for a passive matrix light-emitting device as well as the above active matrix light-emitting device. FIGS. 4A and 4B illustrate a perspective view and a cross-sectional view of a passive matrix light-emitting device using a light-emitting element of one embodiment of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are aslope so that a distance between both the sidewalls is gradually narrowed toward the surface of the substrate. In other words, a cross section taken along the direction of the short side of the partition layer 506 is trapezoidal, and the base (side facing in a direction parallel to the plane direction of the insulating layer 505 and being in contact with the insulating layer 505) is shorter than the upper side (side facing in the direction parallel to the plane direction of the insulating layer 505 and not being in contact with the insulating layer 505). By providing of the partition layer 506 in such a manner, a defect of a light-emitting element due to static electricity or the like can be prevented.

Thus, the passive matrix light-emitting device having a light-emitting element of one embodiment of the present invention can be obtained.

The light-emitting devices described in Embodiment 4 (the active matrix light-emitting device and the passive matrix light-emitting device) are both formed using a light-emitting element of one embodiment of the present invention, and accordingly, the light-emitting devices have low power consumption.

Note that this embodiment can be combined with any other embodiment as appropriate.

Embodiment 5

In Embodiment 5, with reference to FIGS. 5A to 5E and FIG. 6, description is given of examples of a variety of electronic devices and lighting devices that are completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 5A to 5E.

Figure 5A:
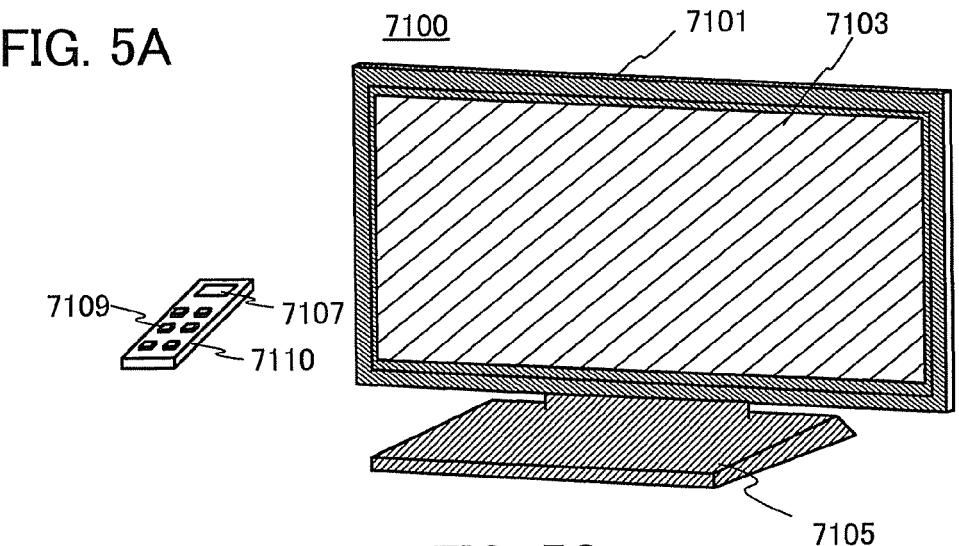
FIGS. 5A to 5E each illustrate an electronic device according to one embodiment of the present invention.

FIG. 5A illustrates an example of a television device. In the television device 7100, a display portion 7103 is incorporated into a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
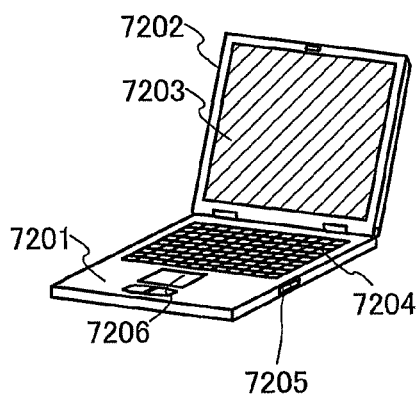

FIG. 5B illustrates a computer having a main body 7201, a housing 7202, a display portion 7203, a keyboard 7204, an external connecting port 7205, a pointing device 7206, and the like. This computer is manufactured by using a light-emitting device for the display portion 7203.

Figure 5C:
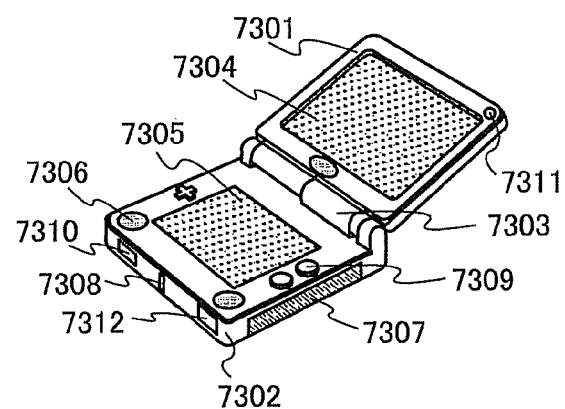

FIG. 5C illustrates a portable game machine having two housings, a housing 7301 and a housing 7302, which are connected with a joint portion 7303 so that the portable game machine can be opened or folded. A display portion 7304 is incorporated into the housing 7301 and a display portion 7305 is incorporated into the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as long as a light-emitting device can be used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
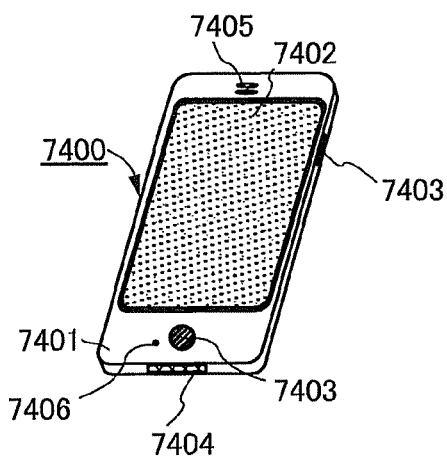

FIG. 5D illustrates an example of a cellular phone. The cellular phone 7400 is provided with operation buttons 7403, an external connection port 7404, a speaker 7405, a microphone 7406, and the like, in addition to a display portion 7402 incorporated into a housing 7401. Note that the cellular phone 7400 is manufactured using a light-emitting device for the display portion 7402.

When the display portion 7402 of the cellular phone 7400 illustrated in FIG. 5D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, whereby personal authentication can be performed. Furthermore, by provision of a backlight or a sensing light source emitting a near-infrared light for the display portion, an image of a finger vein, a palm vein, or the like can also be taken.

Figure 5E:
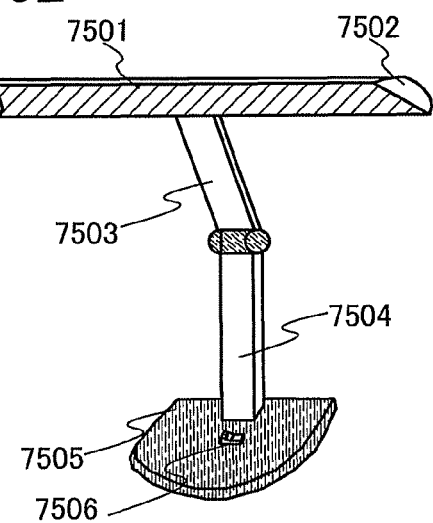

FIG. 5E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that the "lighting device" also encompasses ceiling lights, wall lights, and the like.

Figure 6:
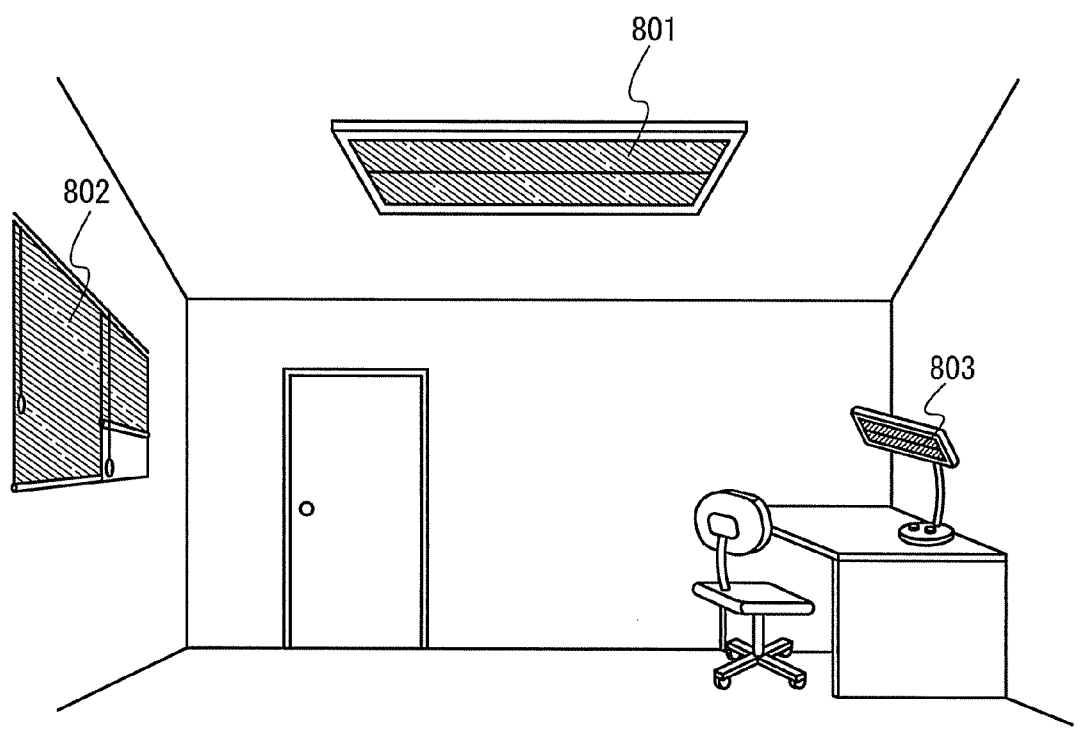
FIG. 6 illustrates lighting devices according to one embodiment of the present invention.

FIG. 6 illustrates an example in which a light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 6, a desk lamp 803 described with reference to FIG. 5E may be used together in a room provided with the interior lighting device 801.

In the above-described manner, electronic devices or lighting devices can be obtained by application of a light-emitting device. Application range of the light-emitting device is so wide that the light-emitting device can be applied to electronic devices in a variety of fields.

Note that the structure described in this embodiment can be combined with any of the structures described in Embodiments 1 to 4 as appropriate.

Example 1

Synthesis Example 1

This example gives descriptions of a method of synthesizing 3-[4-(dibenzothiophen-4-yl)phenyl)]-4,5-diphenyl-4H-

1,2,4-triazole (abbreviation: DBTTAZ-II) represented by Structural Formula (100) above.

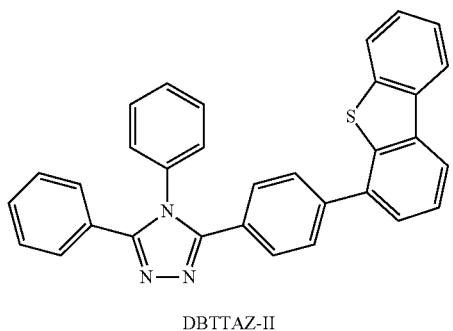 [SMILES: c1ccc(-c2nnc(-c3ccc(-c4cccc5c4sc4ccccc45)cc3)n2-c2ccccc2)cc1]

DBTTAZ-II

A scheme for the synthesis of DBTTAZ-II is illustrated in (C-1).

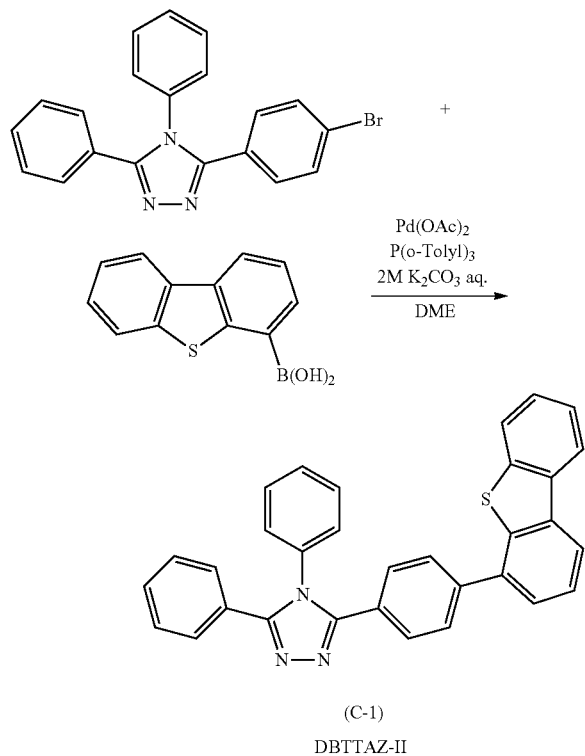

(C-1)
DBTTAZ-II

Into a 300-mL three neck flask were placed 1.9 g (5.3 mmol) of 3-(4-bromophenyl)-4,5-diphenyl-4H-1,2,4-triazole, 1.3 g (5.8 mmol) of dibenzothiophene-4-boronic acid, 0.17 g (0.56 mmol) of tri(ortho-tolyl)phosphine, 50 mL of ethylene glycol dimethyl ether, and 5 mL of a 2M aqueous solution of potassium carbonate. This mixture was degassed by stirring under reduced pressure, and the air in the flask was replaced with nitrogen. To this mixture was added 29 mg (0.13 mmol) of palladium(II) acetate. This mixture was stirred under a nitrogen stream at 80° C. for 4 hours. After a predetermined time had elapsed, water was added to this mixture, and organic substances were extracted from the aqueous layer with toluene. The solution of the obtained extract was combined with the organic layer, and the mixture was washed with saturated brine and dried with magnesium sulfate. The obtained mixture was gravity filtered, and the filtrate was concentrated to give a solid. The obtained solid was purified by silica gel column chromatography. At this time, a mixed solvent (chloroform and ethyl acetate in a 6:1 ratio) was used as a developing solvent. Furthermore, recrystallization from toluene was carried out, whereby 2.3 g of a white powder of the substance to be produced was obtained in 89% yield.

By a train sublimation method, 2.3 g of the obtained white powder of the substance to be produced was purified. In the purification, the white powder was heated at 250° C. under a pressure of 10 Pa with a flow rate of argon gas of 5 mL/min. After the purification, 1.5 g of a white powder was recovered in 65% yield.

A nuclear magnetic resonance (NMR) method identified this compound as 3-[4-(dibenzothiophen-4-yl)phenyl)]-4,5-diphenyl-4H-1,2,4-triazole (abbreviation: DBTTAZ-II), which was the substance to be produced.

$^1$H NMR data of the obtained compound are as follows: $^1$H NMR (DMSO-$d_6$, 300 MHz): δ (ppm)=7.34-7.45 (m, 5H), 7.52-7.66 (m, 11H), 7.76 (d, J=8.4 Hz, 2H), 8.02-8.04 (m, 1H), 8.41-8.43 (m, 2H).

Figure 7A:
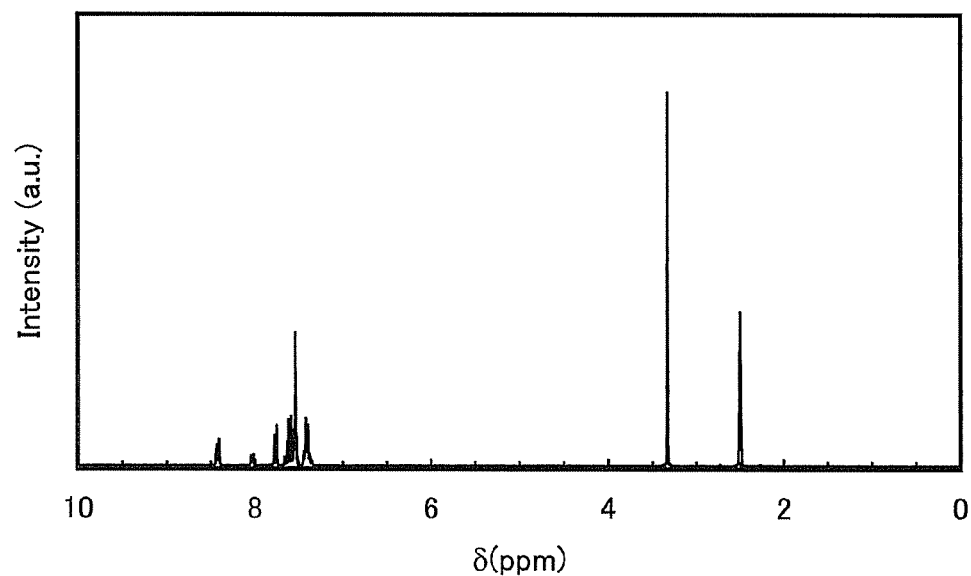
FIGS. 7A and 7B show the $^1$H NMR charts of 3-[4-(dibenzothiophen-4-yl)phenyl)]-4,5-diphenyl-4H-1,2,4-triazole (abbreviation: DBTTAZ-II).
Figure 7B:
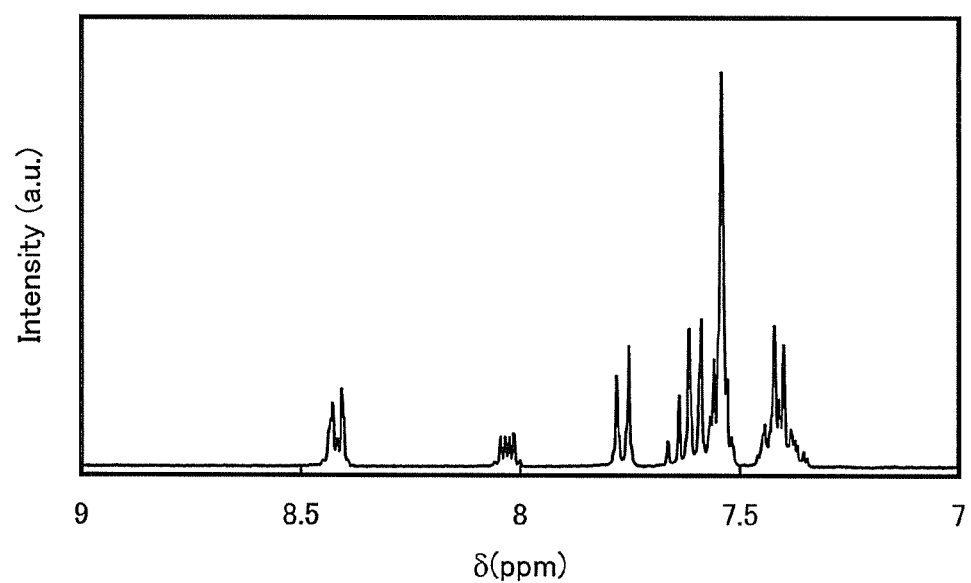

FIGS. 7A and 7B show the $^1$H NMR charts. Note that FIG. 7B is a chart showing an enlarged part of FIG. 7A in the range of 7.0 ppm to 9.0 ppm.

Figure 8A:
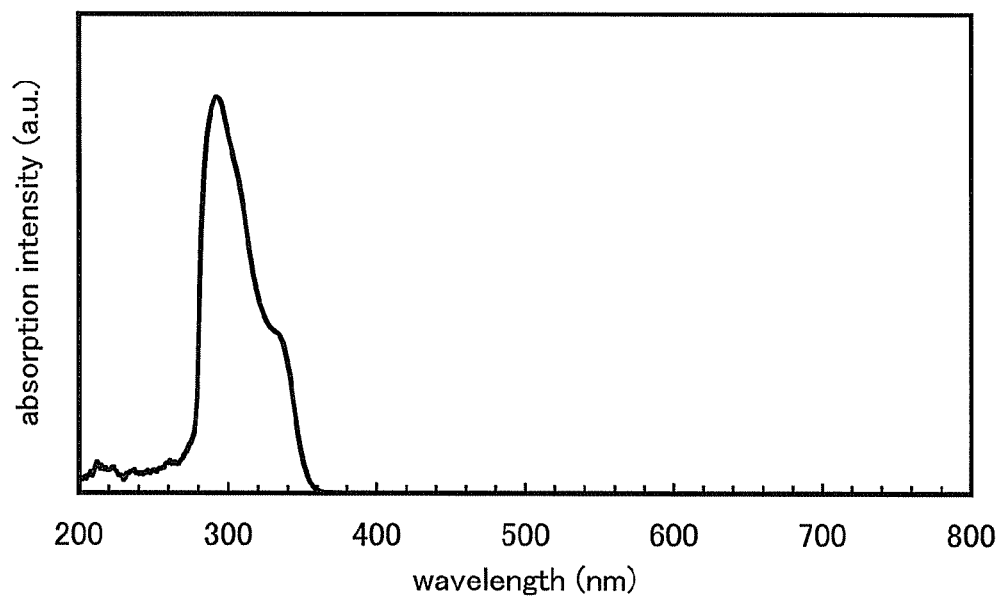
FIGS. 8A and 8B show an absorption spectrum and an emission spectrum of a toluene solution of DBTTAZ-II.
Figure 8B:
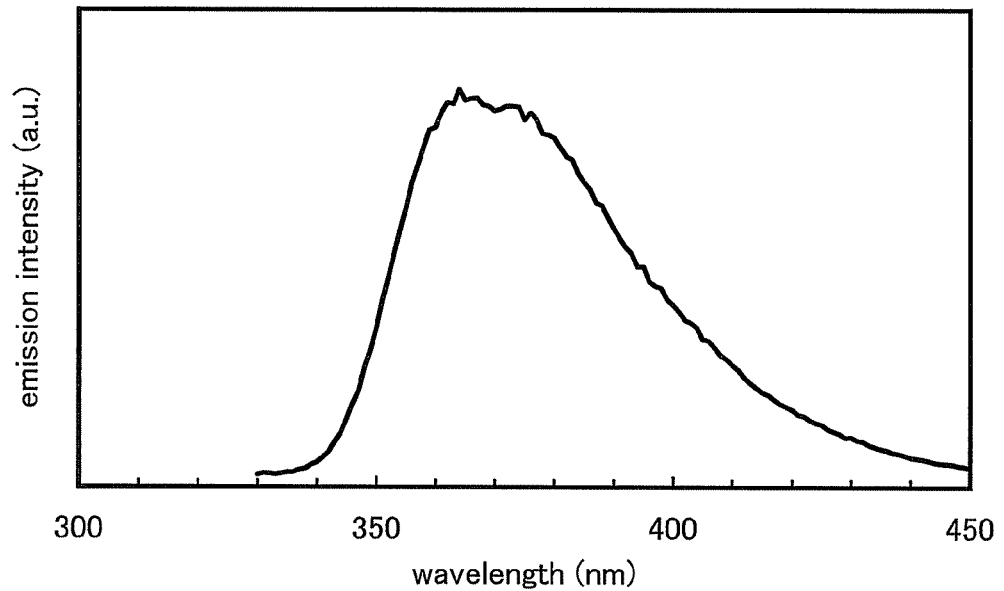
Figure 9A:
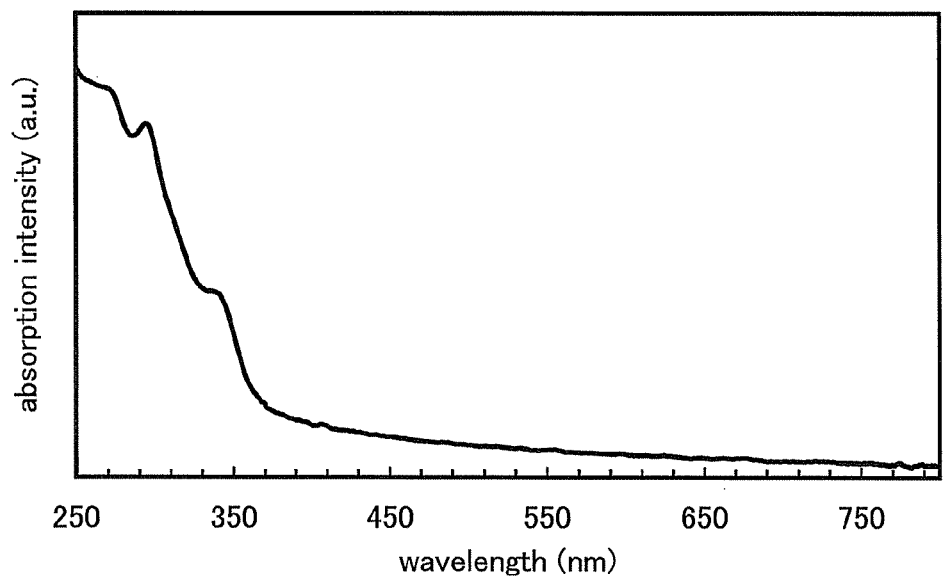
FIGS. 9A and 9B show an absorption spectrum and an emission spectrum of a thin film of DBTTAZ-II.
Figure 9B:
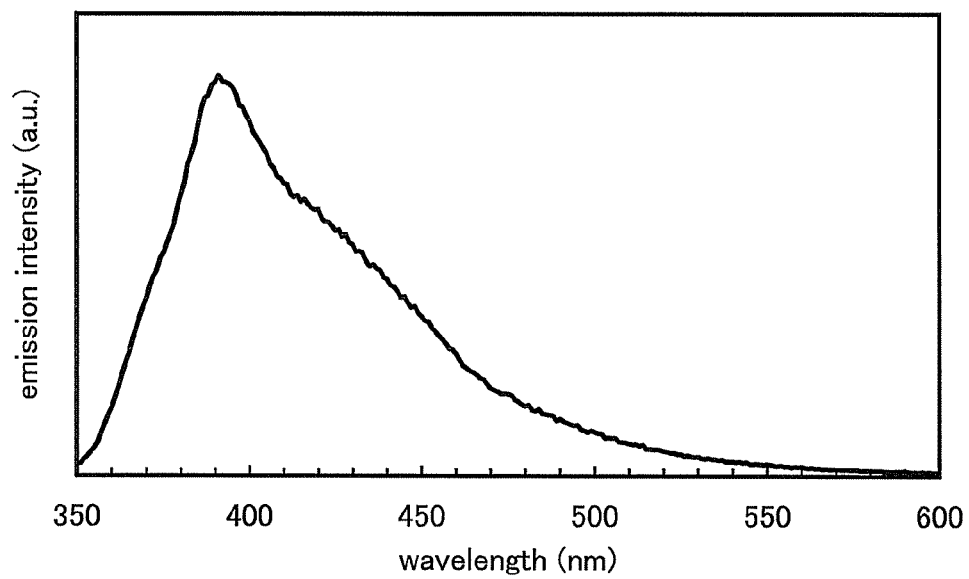

Further, FIG. 8A shows an absorption spectrum of a toluene solution of DBTTAZ-II, and FIG. 8B shows an emission spectrum thereof. FIG. 9A shows an absorption spectrum of a thin film of DBTTAZ-II, and FIG. 9B shows an emission spectrum thereof. An ultraviolet-visible spectrophotometer (V-550, manufactured by JASCO Corporation) was used for the measurements. Samples were prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIG. 8A and FIG. 9A, the horizontal axis represents wavelength (nm) and the vertical axis represents absorption intensity (arbitrary unit). In FIG. 8B and FIG. 9B, the horizontal axis represents wavelength (nm) and the vertical axis represents emission intensity (arbitrary unit). In the case of the toluene solution, absorption peaks were at around 292 nm, 305 nm, and 332 nm, and an emission wavelength peak was at 365 nm (at an excitation wavelength of 290 nm). In the case of the thin film, absorption peaks were at around 269 nm, 294 nm, and 338 nm, and an emission wavelength peak was at 391 nm (at an excitation wavelength of 341 nm).

Example 2

Figure 10A:
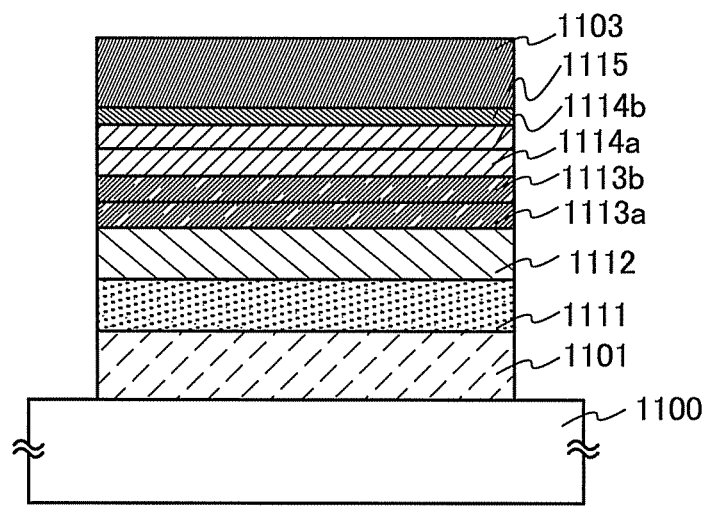
FIGS. 10A and 10B each illustrate a light-emitting element of Example.

In this example, a light-emitting element according to one embodiment of the present invention will be described with reference to FIG. 10A. Structural formulae of materials used in this example are illustrated below.

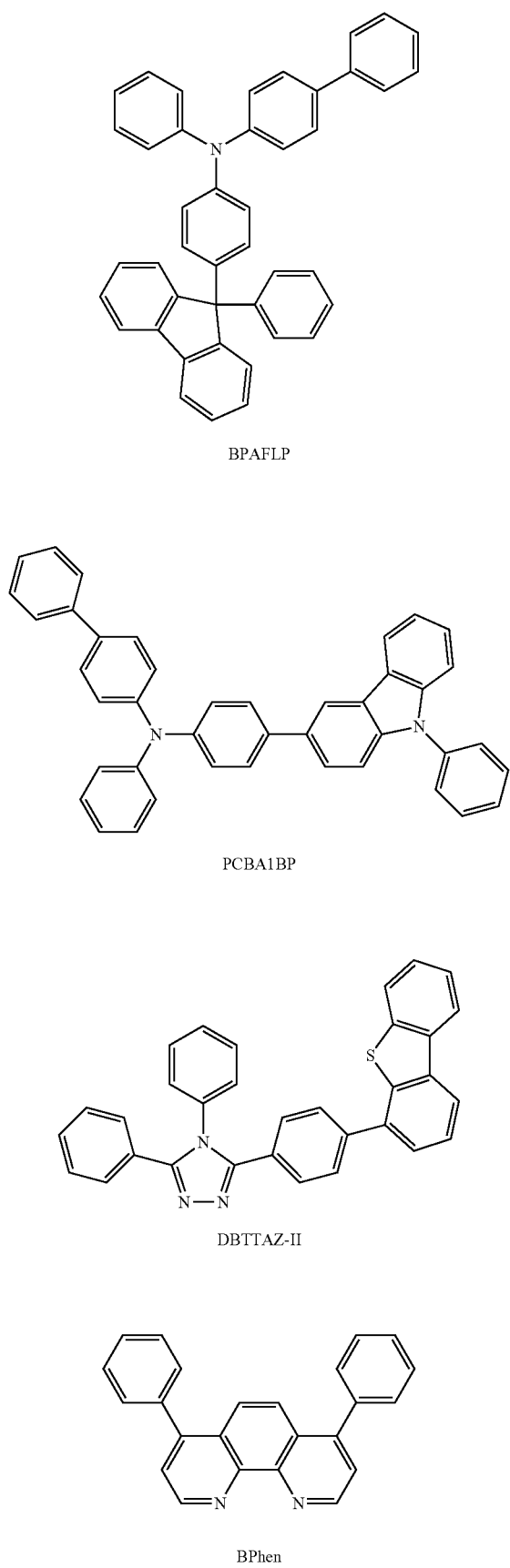

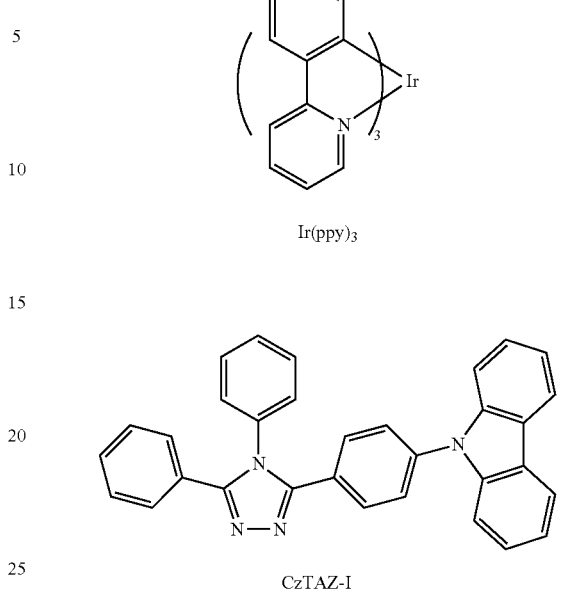

Hereinafter, methods of fabricating Light-emitting Element 1 of this example and Reference Light-emitting Element 2 will be described.

(Light-Emitting Element 1)

First, indium tin oxide containing silicon oxide (ITSO) was deposited over a glass substrate 1100 by a sputtering method, whereby a first electrode 1101 was formed. Note that its thickness was set to 110 nm and the electrode area was set to 2 mm×2 mm.

Next, as pretreatment for forming the light-emitting element on the substrate 1100, after washing of a surface of the substrate with water and baking that was performed at 200° C. for one hour, UV ozone treatment was performed for 370 seconds.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, 4-phenyl-4'-(9-phenylfluoren-9-yl)triphenylamine (abbreviation: BPAFLP) and molybdenum(VI) oxide were co-evaporated to form a hole-injection layer 1111 on the first electrode 1101. The thickness of the hole-injection layer 1111 was set to 50 nm, and the weight ratio of BPAFLP to molybdenum(VI) oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, a BPAFLP film was formed to a thickness of 10 nm on the hole-injection layer 1111, whereby a hole-transport layer 1112 was formed.

Further, 3-[4-(dibenzothiophen-4-yl)phenyl)]-4,5-diphenyl-4H-1,2,4-triazole (abbreviation: DBTTAZ-II) synthesized in Example 1, 4-phenyl-4'-(9-phenyl-9H-carbazol-3-yl)triphenylamine (abbreviation: PCBA1BP), and tris(2-phenylpyridinato-N,$C^{2'}$)iridium(III) (abbreviation: Ir(ppy)$_3$) were co-evaporated to form a first light-emitting layer 1113a on the hole-transport layer 1112. The weight ratio of DBTTAZ-II to PCBA1BP and Ir(ppy)$_3$ was adjusted to 1:0.2:0.08 (=DBTTAZ-II:PCBA1BP:Ir(ppy)$_3$). The thickness of the first light-emitting layer 1113a was set to 20 nm.

Next, DBTTAZ-II and Ir(ppy)$_3$ were co-evaporated, whereby a second light-emitting layer 1113b was formed on the first light-emitting layer 1113a. The weight ratio of DBTTAZ-II to Ir(ppy)$_3$ was adjusted to 1:0.08 (=DBTTAZ-II:Ir(ppy)$_3$). The thickness of the second light-emitting layer 1113b was set to 20 nm.

Further, a DBTTAZ-II film was formed to a thickness of 15 nm on the second light-emitting layer 1113b, whereby a first electron-transport layer 1114a was formed.

Then, a bathophenanthroline (abbreviation: BPhen) film was formed to a thickness of 15 nm on the first electron-transport layer 1114a, whereby a second electron-transport layer 1114b was formed.

Further, a lithium fluoride (LiF) film was formed to a thickness of 1 nm on the second electron-transport layer 1114b by evaporation, whereby an electron-injection layer 1115 was formed.

Lastly, an aluminum film was formed to a thickness of 200 nm by evaporation as a second electrode 1103 functioning as a cathode. Thus, Light-emitting Element 1 of this example was fabricated.

Note that, in the above evaporation process, evaporation was all performed by a resistance heating method.
(Reference Light-Emitting Element 2)

To form the first light-emitting layer 1113a of Reference Light-emitting Element 2, 9-[4-(4,5-diphenyl-4H-1,2,4-triazol-3-yl)phenyl]-9H-carbazole (abbreviation: CzTAZ-I), PCBA1BP, and Ir(ppy)$_3$ were co-evaporated. The weight ratio of CzTAZ-I to PCBA1BP and Ir(ppy)$_3$ was adjusted to 1:0.25:0.08 (=CzTAZ-I:PCBA1BP:Ir(ppy)$_3$). The thickness of the first light-emitting layer 1113a was set to 20 nm.

Furthermore, CzTAZ-I and Ir(ppy)$_3$ were co-evaporated to form the second light-emitting layer 1113b of Reference Light-emitting Element 2. The weight ratio of CzTAZ-I to Ir(ppy)$_3$ was adjusted to 1:0.08 (=CzTAZ-I:Ir(ppy)$_3$). The thickness of the second light-emitting layer 1113b was set to 20 nm.

The first electron-transport layer 1114a of Reference Light-emitting Element 2 was formed with a 15-nm-thick CzTAZ-I film. The components other than the first light-emitting layer 1113a, the second light-emitting layer 1113b, and the first electron-transport layer 1114a were formed in the same manner as those of Light-emitting Element 1.

Table 1 shows element structures of Light-emitting Element 1 and Reference Light-emitting Element 2 obtained as described above.

TABLE 1

| | first electrode | hole-injection layer | hole-transport layer | first light-emitting layer | second light-emitting layer | first electron-transport layer | second electron-transport layer | electon-injection layer | second electrode |
|---|---|---|---|---|---|---|---|---|---|
| Light-emitting Element 1 | ITSO 110 nm | BPAFLP: MoOx (=4:2) 50 nm | BPAFLP 10 nm | DBTTAZ-II: PCBA1BP: Ir(ppy)$_3$ (=1:0.2:0.08) 20 nm | DBTTAZ-II: Ir(ppy)$_3$ (=1:0.08) 20 nm | DBTTAZ-II 15 nm | BPhen 15 nm | LiF 1 nm | Al 200 nm |
| Reference Light-emitting Element 2 | ITSO 110 nm | BPAFLP: MoOx (=4:2) 50 nm | BPAFLP 10 nm | CzTAZ-I: PCBA1BP: Ir(ppy)$_3$ (=01:0.25:0.08) 20 nm | CzTAZ-I: Ir(ppy)$_3$ (=1:0.08) 20 nm | CzTAZ-I 15 nm | BPhen 15 nm | LiF 1 nm | Al 200 nm |

In a glove box containing a nitrogen atmosphere, Light-emitting Element 1 and Reference Light-emitting Element 2 were sealed so as not to be exposed to air. Then, operation characteristics of these elements were measured. Note that the measurements were carried out at room temperature (in the atmosphere kept at 25° C.).

Figure 11:
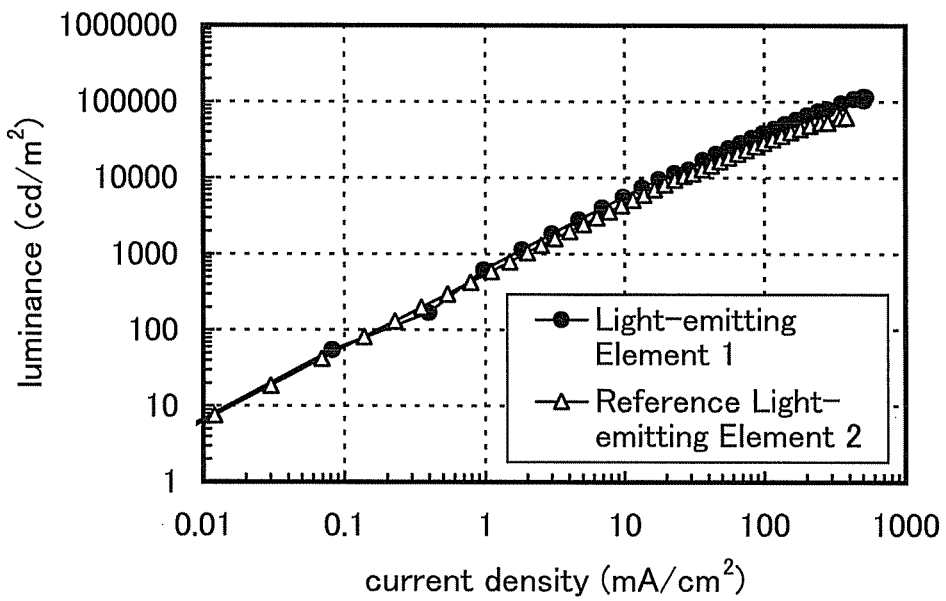
FIG. 11 shows current density versus luminance characteristics of light-emitting elements of Example.
Figure 12:
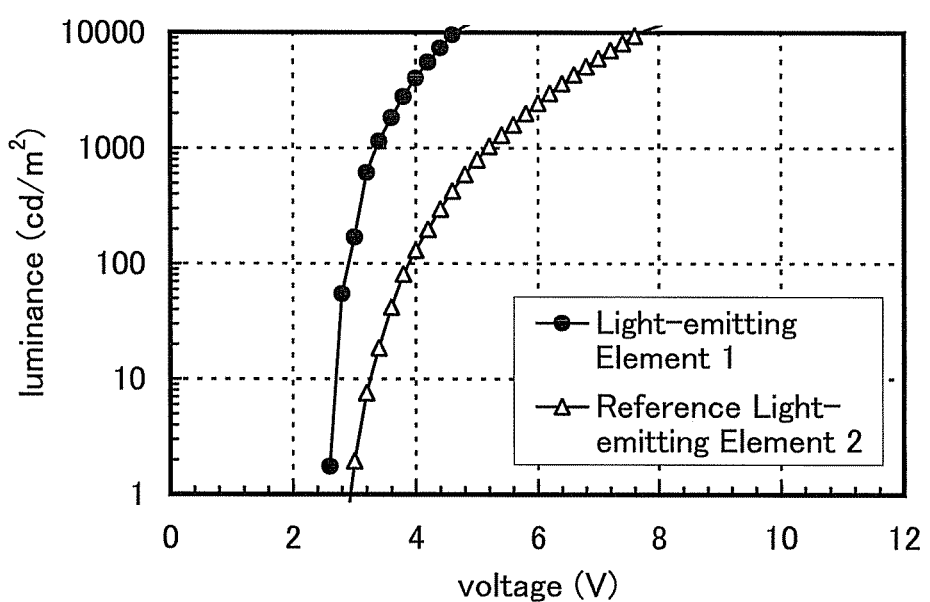
FIG. 12 shows voltage versus luminance characteristics of the light-emitting elements of Example.
Figure 13:
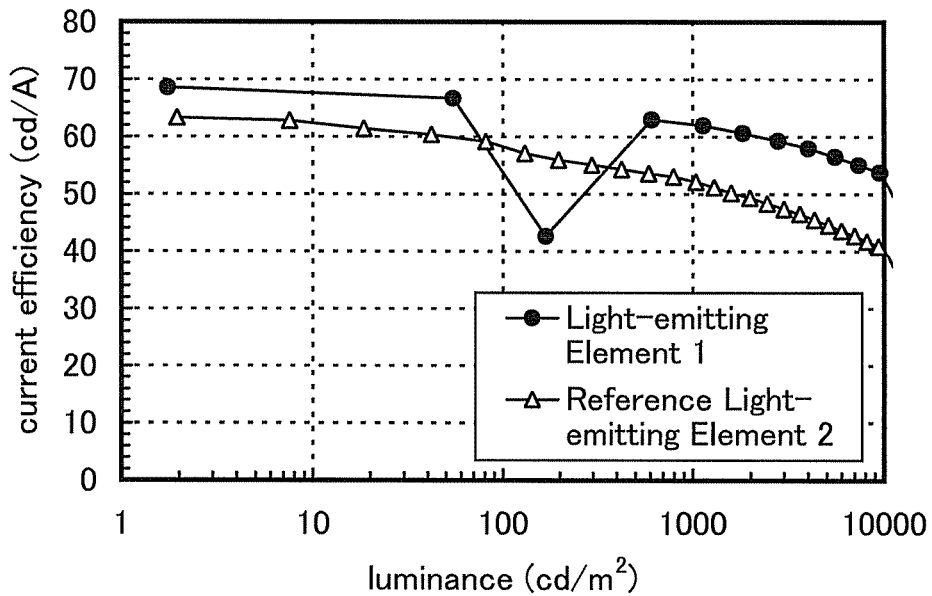
FIG. 13 shows luminance characteristics versus current efficiency of the light-emitting elements of Example.
Figure 14:
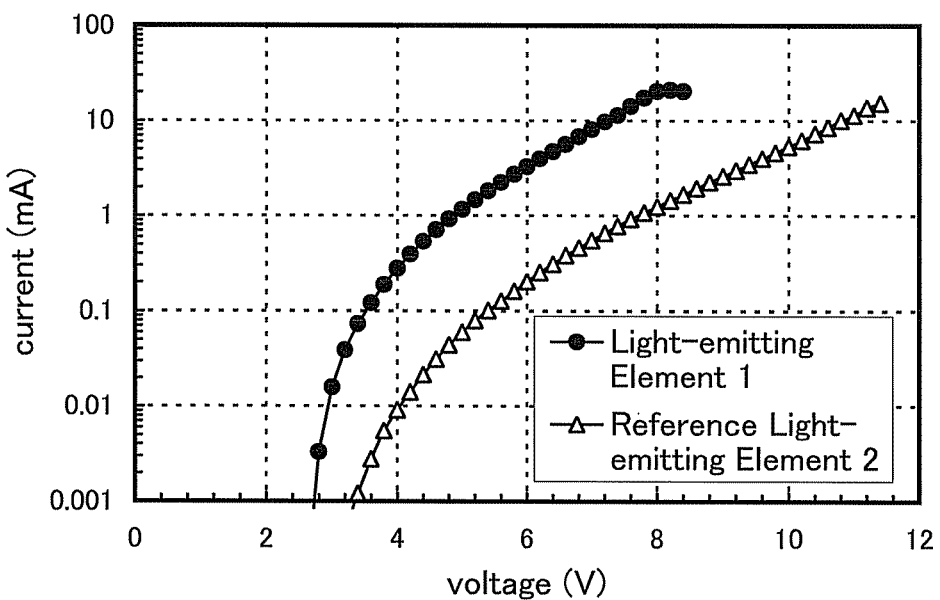
FIG. 14 shows voltage versus current of the light-emitting elements of Example.

FIG. 11 shows the current density versus luminance characteristics of Light-emitting Element 1 and Reference Light-emitting Element 2. In FIG. 11, the horizontal axis represents current density (mA/cm$^2$) and the vertical axis represents luminance (cd/m$^2$). In addition, FIG. 12 shows the voltage versus luminance characteristics. In FIG. 12, the horizontal axis represents voltage (V) and the vertical axis represents luminance (cd/m$^2$). FIG. 13 shows the luminance versus current efficiency characteristics. In FIG. 13, the horizontal axis represents luminance (cd/m$^2$) and the vertical axis represents current efficiency (cd/A). FIG. 14 shows the voltage versus current characteristics. In FIG. 14, the horizontal axis represents voltage (V) and the vertical axis represents current (mA). Further, Table 2 shows the voltage (V), current density (mA/cm$^2$), CIE chromaticity coordinates (x, y), current efficiency (cd/A), and external quantum efficiency (%) of the light-emitting element at a luminance of around 1000 cd/m$^2$.

TABLE 2

| | voltage (V) | current density (mA/cm$^2$) | CIE chromaticity coordinates x CIE chromaticity coordinates y | | luminance (cd/m$^2$) | current efficiency (cd/A) | external quantum efficiency (%) |
|---|---|---|---|---|---|---|---|
| Light-emitting Element 1 | 3.4 | 1.8 | 0.32 | 0.62 | 1100 | 62 | 18 |
| Reference Light-emitting Element 2 | 5.2 | 2.0 | 0.32 | 0.61 | 1000 | 52 | 16 |

As shown in Table 2, the CIE chromaticity coordinates (x, y) of Light-emitting Element 1 were (0.32, 0.62) at a luminance of 1100 cd/m$^2$, and those of Reference Light-emitting Element 2 were (0.32, 0.61) at a luminance of 1000 cd/m$^2$. It was found that these light-emitting elements exhibited light emission from Ir(ppy)$_3$.

To produce a certain luminance, a lower voltage was used in Light-emitting Element 1 than in Reference Light-emitting Element 2, as can be seen from FIG. 12. This is because Light-emitting Element 1 can obtain a larger amount of current at a lower voltage. Therefore, it can be said that Light-emitting Element 1 is an element capable of driving at a lower voltage than Reference Light-emitting Element 2.

In addition, Light-emitting Element 1 has a higher current efficiency than Reference Light-emitting Element 2, as shown in FIG. 13 and Table 2.

As described above, the light-emitting element having high current efficiency and the capability of low-voltage driving was able to be fabricated using DBTTAZ-II, which was produced in Example 1, as the host material of a light-emitting layer.

Figure 15:
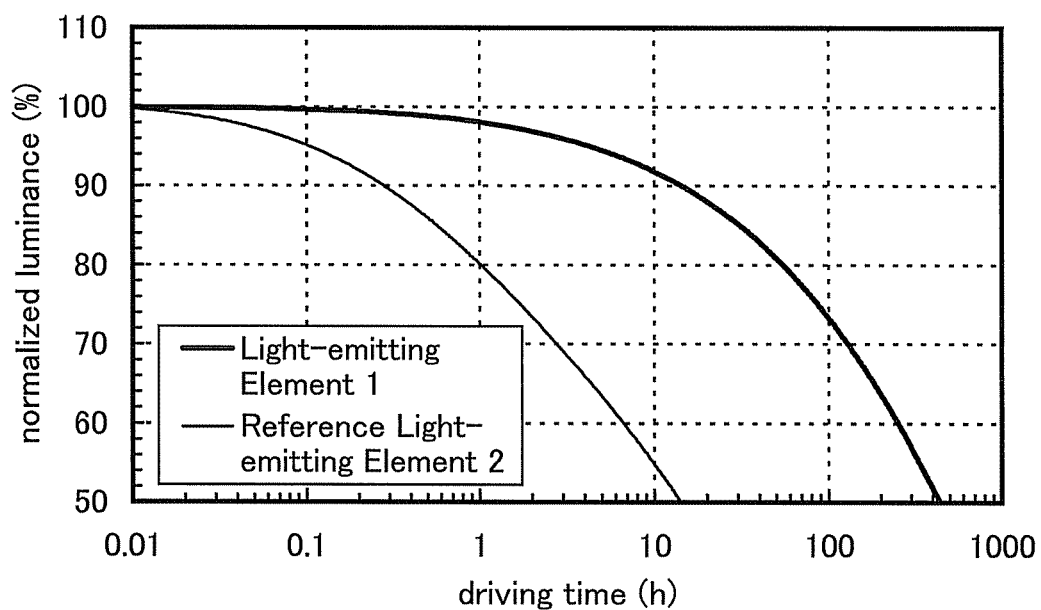
FIG. 15 shows results of reliability tests of the light-emitting elements of Example.

Next, Light-emitting Element 1 and Reference Light-emitting Element 2 were subjected to reliability tests. Results of the reliability tests are shown in FIG. 15. In FIG. 15, the vertical axis represents normalized luminance (%) with an initial luminance of 100%, and the horizontal axis represents driving time (h) of the elements. In the reliability tests, Light-emitting Element 1 of this example and Reference Light-emitting Element 2 were driven under the conditions where the initial luminance was 1000 cd/m$^2$ and the current density was constant. As can be seen from FIG. 15, Light-emitting Element 1 kept 50% of the initial luminance until after 440 hours had elapsed, but Light-emitting Element 2 kept 50% of the initial luminance until after 14 hours had elapsed. These results of the reliability tests revealed that Light-emitting Element 1, to which one embodiment of the present invention was applied, had a longer lifetime than Reference Light-emitting Element 2, in which CzTAZ-I, a substance having substantially as high triplet excitation energy as a triazole derivative of one embodiment of the present invention, was used as the host material of the light-emitting layer.

Example 3

Figure 10B:
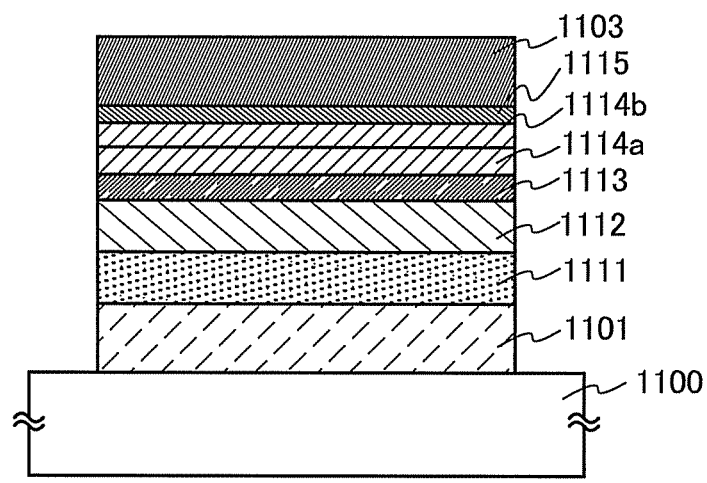

In this example, a light-emitting element according to one embodiment of the present invention will be described with reference to FIG. 10B. Structural formulae of materials used in this example are illustrated below. Note that the formulae of the materials which are described above will be omitted.

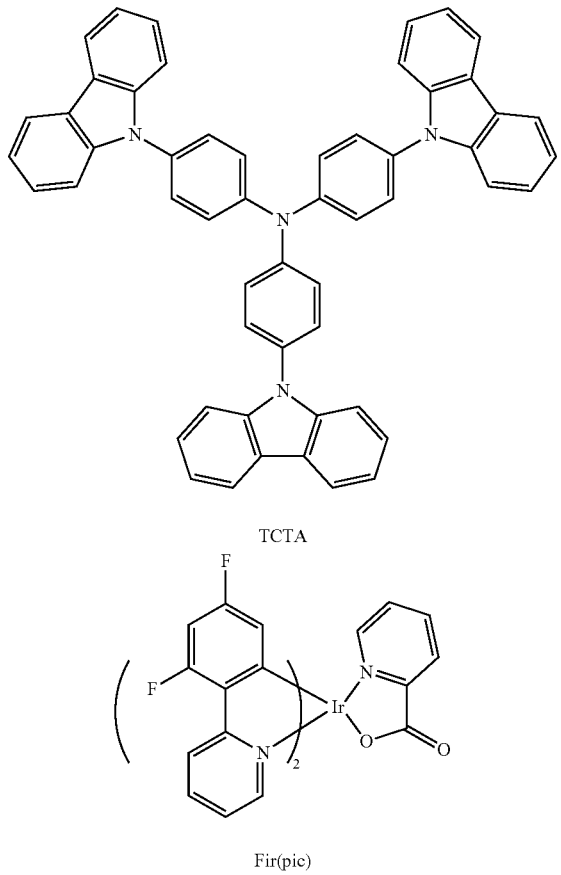

TCTA

Fir(pic)

Hereinafter, methods of fabricating Light-emitting Element 3 of this example will be described.
(Light-Emitting Element 3)

First, indium tin oxide containing silicon oxide (ITSO) was deposited over a glass substrate 1100 by a sputtering method, whereby a first electrode 1101 was formed. Note that its thickness was set to 110 nm and the electrode area was set to 2 mm×2 mm.

Next, as pretreatment for forming the light-emitting element on the substrate 1100, after washing of a surface of the substrate with water and baking that was performed at 200° C. for one hour, UV ozone treatment was performed for 370 seconds.

After that, the substrate was transferred into a vacuum evaporation apparatus where the pressure had been reduced to approximately 1e Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, 4,4',4''-tris(carbazol-9-yl)triphenylamine (abbreviation: TCTA) and molybdenum(VI) oxide were co-evaporated to form a hole-injection layer 1111 on the first electrode 1101. The thickness of the hole-injection layer 1111 was set to 50 nm, and the weight ratio of TCTA to molybdenum(VI) oxide was adjusted to 4:2 (=TCTA:molybdenum oxide). Note that the co-evaporation method refers to an evaporation method in which evaporation is carried out from a plurality of evaporation sources at the same time in one treatment chamber.

Next, a TCTA film was formed to a thickness of 10 nm on the hole-injection layer 1111, whereby a hole-transport layer 1112 was formed.

Further, DBTTAZ-II synthesized in Example 1, TCTA, and bis[2-(4',6'-difluorophenyl)pyridinato-N,$C^{2'}$]iridium(III) picolinate (abbreviation: Fir(pic), FIrpic) were co-evaporated to form a light-emitting layer 1113 on the hole-transport layer 1112. The weight ratio of DBTTAZ-II to TCTA and FIrpic was adjusted to 1:0.15:0.06 (=DBTTAZ-II:TCTA:FIrpic). The thickness of the light-emitting layer 1113 was set to 30 nm.

In a glove box containing a nitrogen atmosphere, Light-emitting Element 3 is sealed so as not to be exposed to air. Then, operation characteristics of this element were measured. Note that the measurements were carried out at room temperature (in the atmosphere kept at 25° C.).

Figure 16:
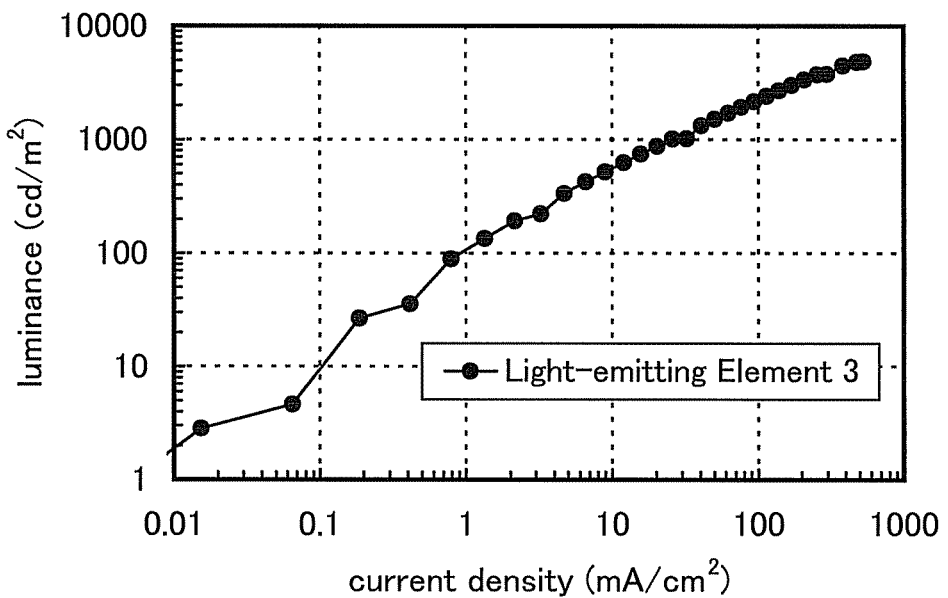
FIG. 16 shows current density versus luminance characteristics of a light-emitting element of Example.
Figure 17:
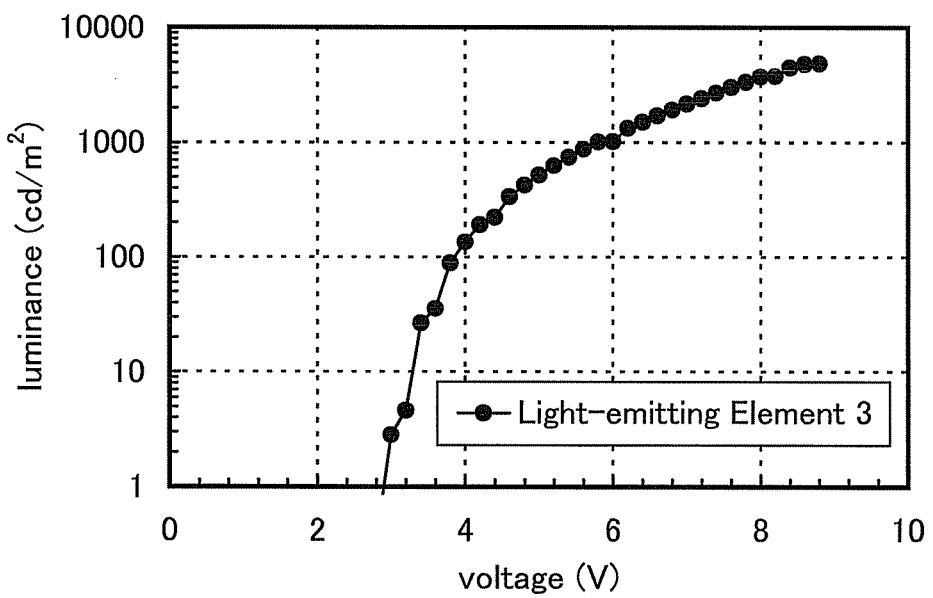
FIG. 17 shows voltage versus luminance characteristics of the light-emitting element of Example.
Figure 18:
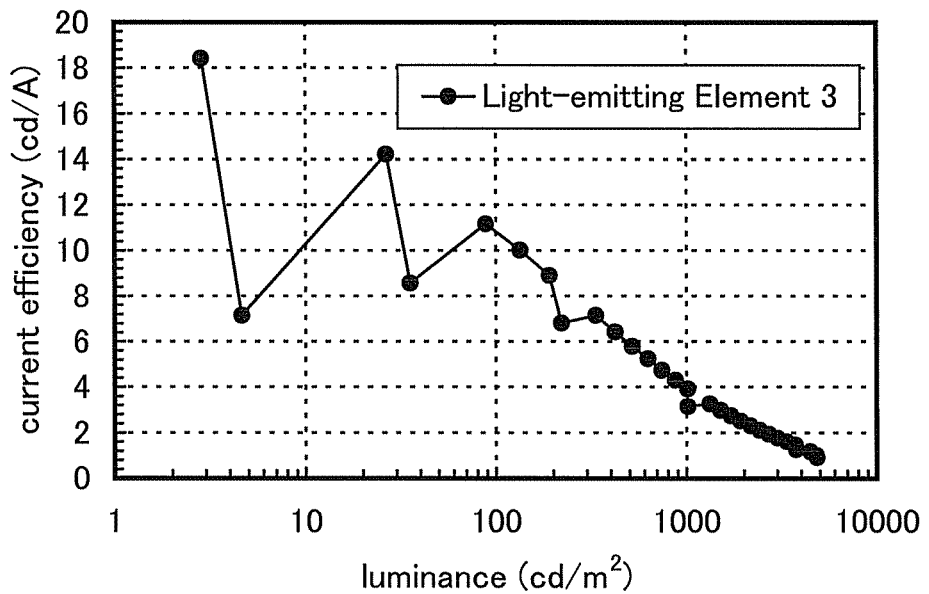
FIG. 18 shows luminance characteristics versus current efficiency of the light-emitting element of Example.
Figure 19:
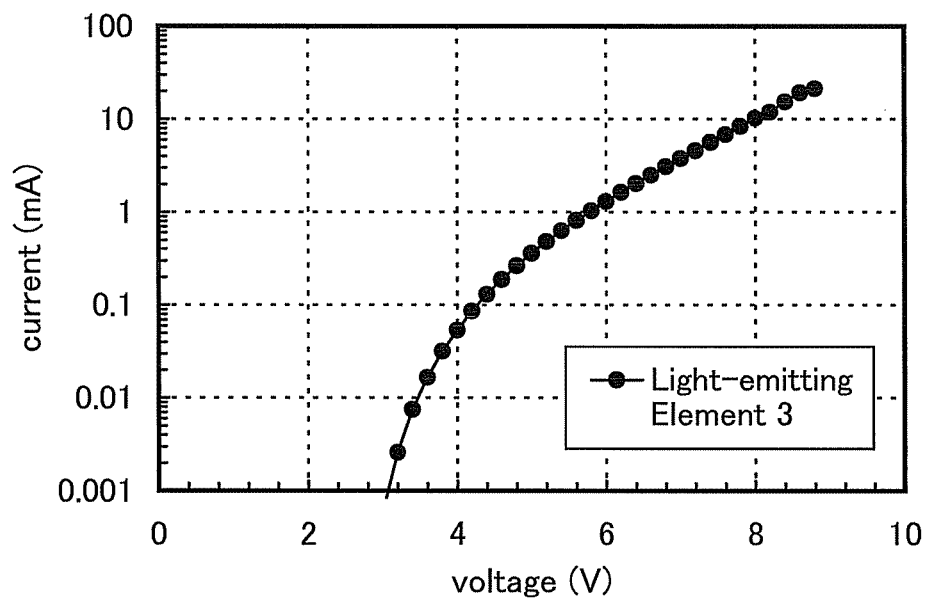
FIG. 19 shows voltage versus current of the light-emitting element of Example.

FIG. 16 shows the current density versus luminance characteristics of Light-emitting Element 3. In FIG. 16, the horizontal axis represents current density (mA/cm$^2$) and the vertical axis represents luminance (cd/m$^2$). In addition, FIG. 17 shows the voltage versus luminance characteristics. In FIG. 17, the horizontal axis represents voltage (V) and the vertical axis represents luminance (cd/m$^2$). FIG. 18 shows the luminance versus current efficiency characteristics. In FIG. 18, the horizontal axis represents luminance (cd/m$^2$) and the vertical axis represents current efficiency (cd/A). FIG. 19 shows the voltage versus current characteristics. In FIG. 19, the horizontal axis represents voltage (V) and the vertical axis represents current (mA). Further, Table 4 shows the voltage (V), current density (mA/cm$^2$), chromaticity coordinates (x, y), current efficiency (cd/A), and external quantum efficiency (%) of the light-emitting element at a luminance of around 1000 cd/m$^2$.

TABLE 4

|  | voltage (V) | current density (mA/cm$^2$) | CIE chromaticity coordinates x CIE chromaticity coordinates y | luminance (cd/m$^2$) | current efficiency (cd/A) | external quantum efficiency (%) |
| --- | --- | --- | --- | --- | --- | --- |
| Light-emitting Element 3 | 5.8 | 26 | 0.21    0.40 | 1000 | 3.9 | 1.7 |

Further, a DBTTAZ-II film was formed to a thickness of 10 nm on the light-emitting layer 1113, whereby a first electron-transport layer 1114a was formed.

Then, a bathophenanthroline (abbreviation: BPhen) film was formed to a thickness of 20 nm on the first electron-transport layer 1114a, whereby a second electron-transport layer 1114b was formed.

Further, a lithium fluoride (LiF) film was formed to a thickness of 1 nm on the second electron-transport layer 1114b by evaporation, whereby an electron-injection layer 1115 was formed.

Lastly, an aluminum film was formed to a thickness of 200 nm by evaporation as a second electrode 1103 functioning as a cathode. Thus, Light-emitting Element 3 of this example was fabricated.

Note that, in the above evaporation process, evaporation was all performed by a resistance heating method.

Table 3 shows an element structure of Light-emitting Element 3 obtained as described above.

As shown in Table 4, the CIE chromaticity coordinates (x, y) of Light-emitting Element 3 were (0.21, 0.40) at a luminance of 1000 cd/m$^2$. It was revealed that this light-emitting element exhibited light emission from FIrpic. The light emission from FIrpic, which produces blue light emission at short wavelengths, was found to show high efficiency since a triazole derivative having high triplet excitation energy was used in the light-emitting element of this example. It was demonstrated that application of the present invention enabled efficient light emission from FIrpic, a phosphorescent compound that produces short-wavelength light emission.

Example 4

Synthesis Example 2

This example gives descriptions of a method of synthesizing 4-[4-(dibenzothiophen-4-yl)phenyl)]-3,5-diphenyl-4H-1,2,4-triazole (abbreviation: 4DBTTAZ-II) represented by Structural Formula (150) above.

TABLE 3

|  | first electrode | hole-injection layer | hole-transport layer | light-emitting layer | first electron-transport layer | second electron-transport layer | electron-injection layer | second electrode |
| --- | --- | --- | --- | --- | --- | --- | --- | --- |
| Light-emitting Element 3 | ITSO 110 nm | TCTA:MoOx (=4:2) 50 nm | TCTA 10 nm | DBTTAZ-II:TCTA: FIrpic (=1:0.15:0.06) 30 nm | DBTTAZ-II 10 nm | BPhen 20 nm | LiF 1 nm | Al 200 nm |

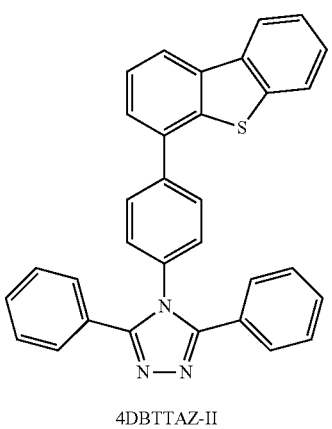 [SMILES: c1ccc(-c2nnc(-c3ccccc3)n2-c2ccc(-c3cccc4c3sc3ccccc34)cc2)cc1]

4DBTTAZ-II

A scheme for the synthesis of 4DBTTAZ-II is illustrated in (D-1).

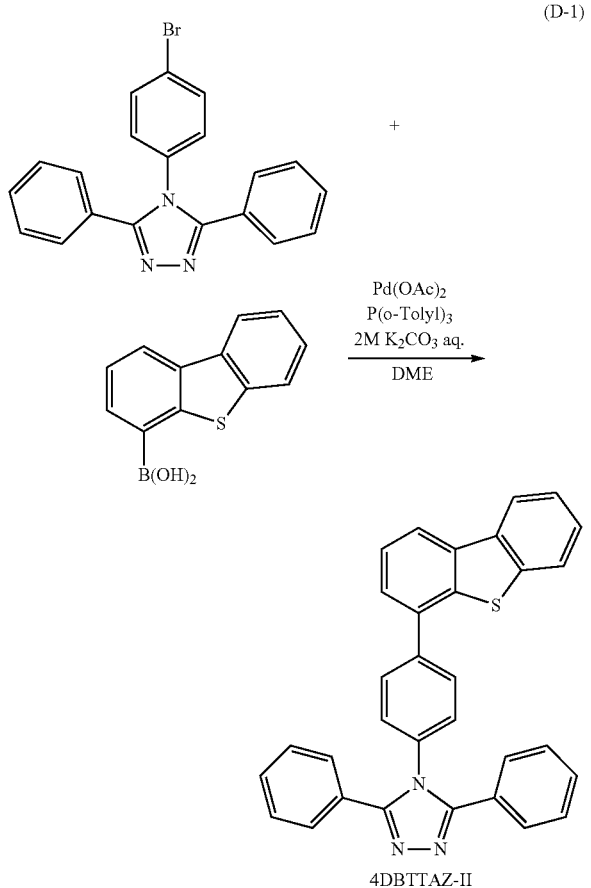

Into a 100-mL three neck flask were placed 1.1 g (3.0 mmol) of 4-(4-bromophenyl)-3,5-diphenyl-4H-1,2,4-triazole, 0.74 g (3.2 mmol) of dibenzothiophene-4-boronic acid, and 0.21 g (0.68 mmol) of tris(2-methylphenyl)phosphine, and the air in the flask was replaced with nitrogen. Into this flask were placed 30 mL of toluene, 3.0 mL of ethanol, and 3.0 mL of a 2M aqueous solution of potassium carbonate. This mixture was degassed by stirring under reduced pressure. To this mixture was added 51 mg (0.23 mmol) of palladium(II) acetate. This mixture was stirred under a nitrogen stream at 80° C. for 11 hours. Furthermore, to the mixture were added 3.0 mL of a 2M aqueous solution of potassium carbonate, 0.14 g (0.46 mmol) of tris(2-methylphenyl)phosphine, and 21 mg (93 μmol) of palladium(II) acetate, and the mixture was stirred at 100° C. for 8 hours. After that, water was added to this mixture, and organic substances were extracted from the aqueous layer of this mixture with chloroform. The solution of the obtained extract was combined with the organic layer, and the mixture was washed with saturated brine and dried with magnesium sulfate. The obtained mixture was gravity filtered, and the filtrate was concentrated to give a solid. The obtained solid was purified by silica gel column chromatography (with a developing solvent of toluene and ethyl acetate in a 4:1 ratio). Furthermore, recrystallization from toluene was carried out, whereby 1.1 g of a white powder of the substance to be produced was obtained in 76% yield.

By a train sublimation method, 1.1 g of the white powder of the substance to be produced was purified. In the purification, the white powder was heated at 250° C. under a pressure of 2.7 Pa with a flow rate of argon gas of 5 mL/min. After the purification, 0.91 g of a white powder was recovered in 81% yield.

A nuclear magnetic resonance (NMR) method identified this compound as 4-[4-(dibenzothiophen-4-yl)phenyl)]-3,5-diphenyl-4H-1,2,4-triazole (abbreviation: 4DBTTAZ-II), which was the substance to be produced.

$^1$H NMR data of the obtained compound are as follows: $^1$H NMR (CDCl3, 300 MHz): δ (ppm)=7.29 (d, J=8.4 Hz, 2H), 7.33-7.44 (m, 6H), 7.49-7.53 (m, 7H), 7.59 (t, J=7.8 Hz, 1H), 7.80 (d, J=8.7 Hz, 2H), 7.85-7.88 (m, 1H), 8.20-8.22 (m, 2H).

Figure 20A:
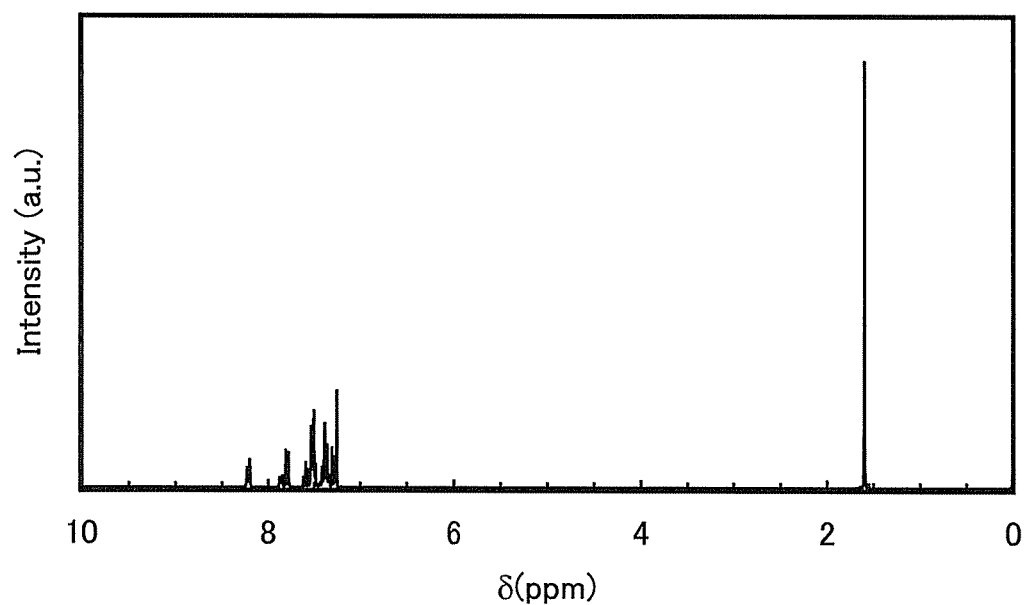
FIGS. 20A and 20B show the $^1$H NMR charts of 4-[4-(dibenzothiophen-4-yl)phenyl)]-3,5-diphenyl-4H-1,2,4-triazole (abbreviation: 4DBTTAZ-II).
Figure 20B:
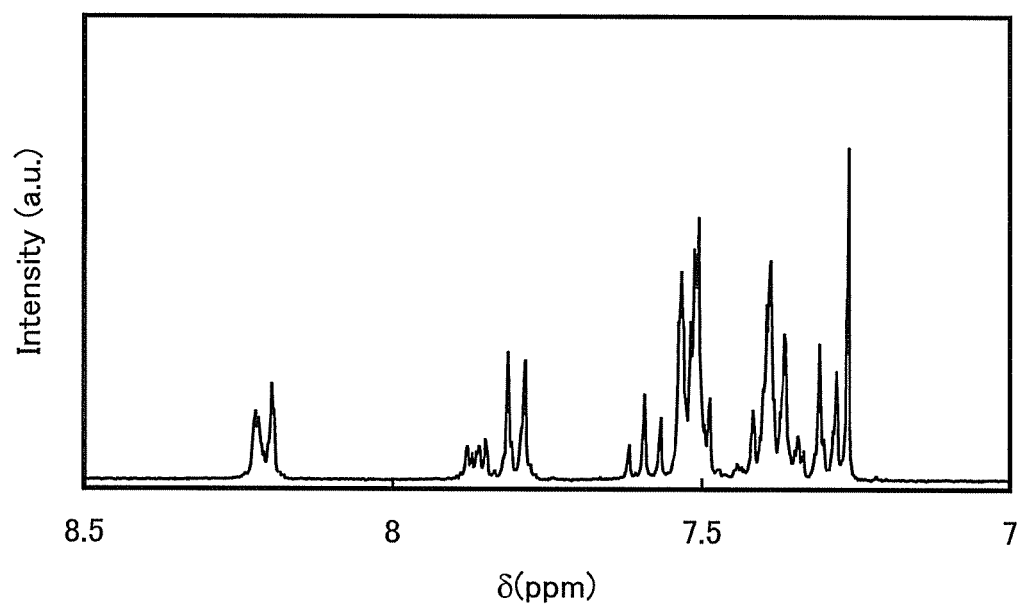

FIGS. 20A and 20B show the $^1$H NMR charts. Note that FIG. 20B is a chart showing an enlarged part of FIG. 20A in the range of 7.0 ppm to 8.5 ppm.

Figure 21A:
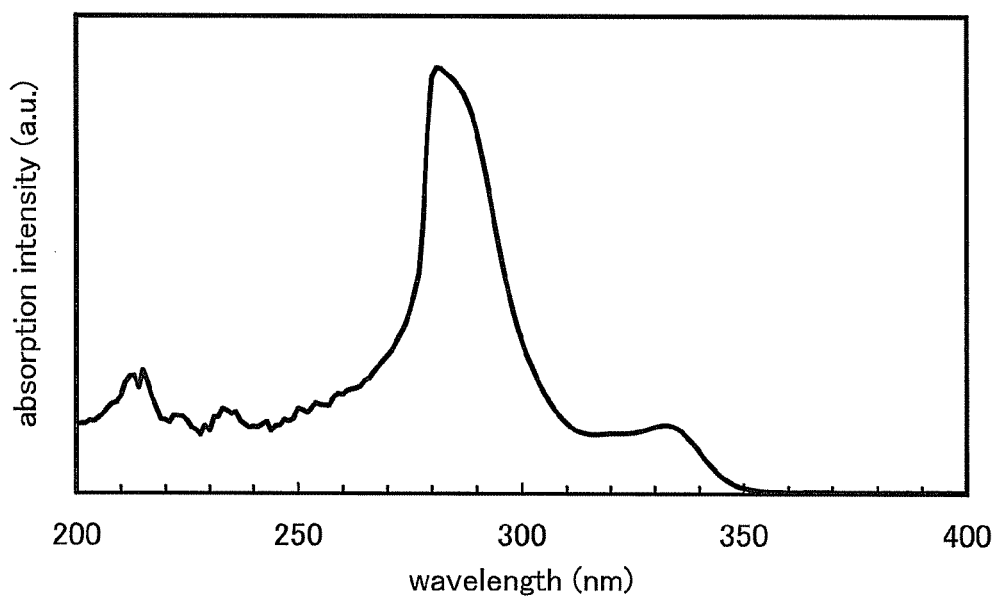
FIGS. 21A and 21B show an absorption spectrum and an emission spectrum of a toluene solution of 4DBTTAZ-II.
Figure 21B:
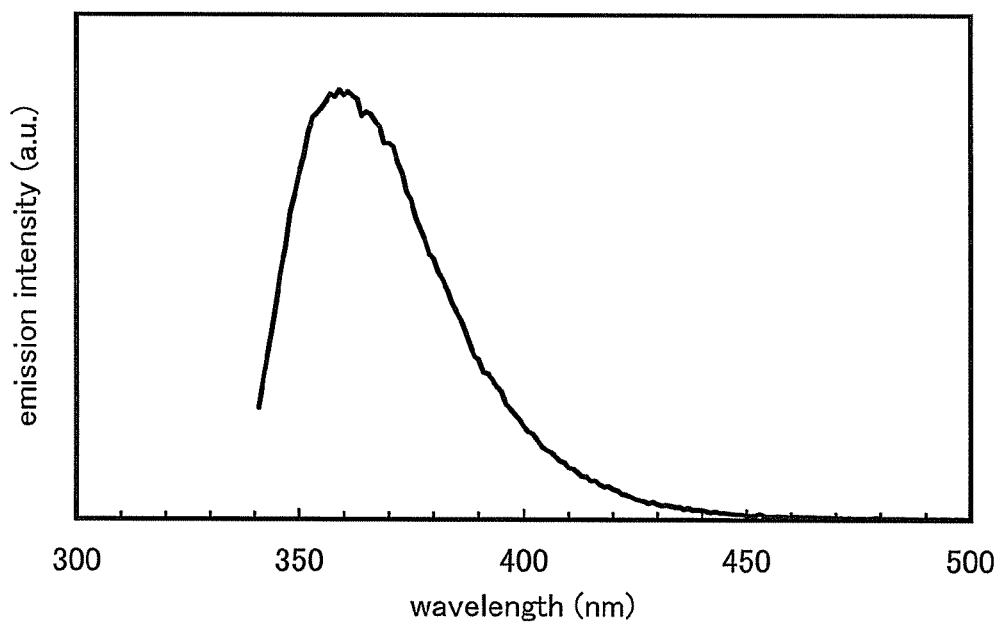

Further, FIG. 21A shows an absorption spectrum of a toluene solution of 4DBTTAZ-II, and FIG. 21B shows an emission spectrum thereof. An ultraviolet-visible spectrophotometer (V-550, manufactured by JASCO Corporation) was used for the measurements. The solution was put in a quartz cell to prepare a sample. The absorption spectrum of the solution was obtained by subtracting the absorption spectra of quartz and toluene from those of quartz and the solution. In FIG. 21A, the horizontal axis represents wavelength (nm) and the vertical axis represents absorption intensity (arbitrary unit). In FIG. 21B, the horizontal axis represents wavelength (nm) and the vertical axis represents emission intensity (arbitrary unit). With the toluene solution, absorption peaks were at around 282 nm and 332 nm, and an emission wavelength peak was at 360 nm (at an excitation wavelength of 334 nm).

Reference Example 1

A method of synthesizing 4-phenyl-4'-(9-phenylfluoren-9-yl)triphenylamine (abbreviation: BPAFLP) used in the above Examples will be specifically described. A structure of BPAFLP is illustrated below.

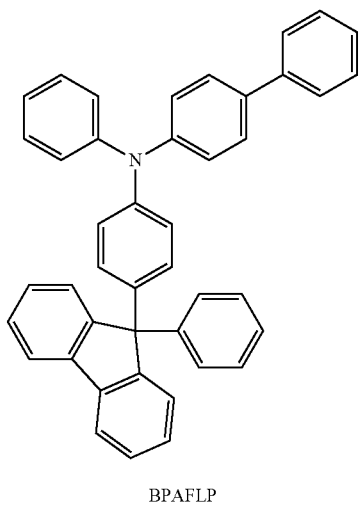 [SMILES: c1ccc(-c2ccc(N(c3ccccc3)c3ccc(C4(c5ccccc5)c5ccccc5-c5ccccc54)cc3)cc2)cc1]

BPAFLP

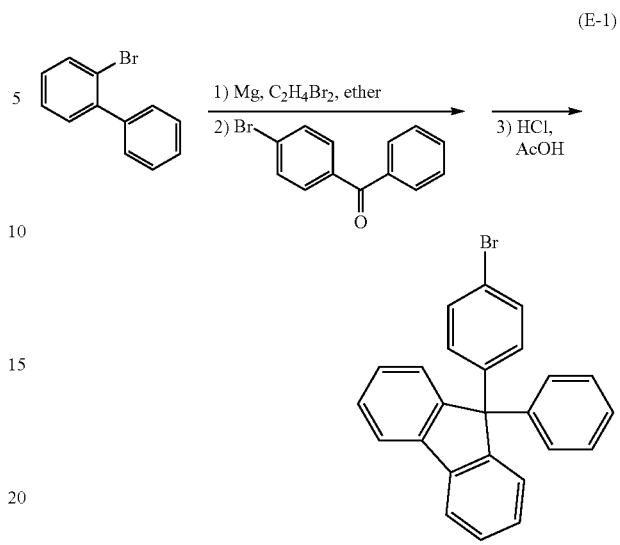

Step 1: Method of Synthesizing 9-(4-Bromophenyl)-9-phenylfluorene

In a 100-mL three-neck flask, 1.2 g (50 mmol) of magnesium was heated and stirred under reduced pressure for 30 minutes, and was activated. The magnesium was cooled to room temperature, and a nitrogen atmosphere was formed. Then, several drops of dibromoethane were added, so that foam formation and heat generation were confirmed. After 12 g (50 mmol) of 2-bromobiphenyl dissolved in 10 mL of diethyl ether was slowly dripped into this mixture, the mixture was heated and stirred under reflux for 2.5 hours, whereby a Grignard reagent was prepared.

Into a 500-mL three-neck flask were placed 10 g (40 mmol) of 4-bromobenzophenone and 100 mL of diethyl ether. After the Grignard reagent which was synthesized in advance was slowly dripped into this mixture, the mixture was heated and stirred under reflux for 9 hours After reaction, this mixture solution was filtered to give a residue. The obtained residue was dissolved in 150 mL of ethyl acetate, and 1N-hydrochloric acid was added to the mixture until it was made acid, which was then stirred for 2 hours. The organic layer of this liquid was washed sequentially with water, and magnesium sulfate was added thereto to remove moisture. This suspension was filtered, and the obtained filtrate was concentrated to give an oily substance.

Into a 500-mL recovery flask were placed this oily substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtrated to give a residue. The obtained residue was washed sequentially with water, an aqueous sodium hydroxide solution, water, and methanol in this order. Then, the mixture was dried to give 11 g of a white powder in 69% yield, which is the substance to be produced. A reaction scheme of the above synthesis method is illustrated in the following (E-1).

Step 2: Method of Synthesizing 4-Phenyl-4'-(9-phenylfluoren-9-yl)triphenylamine (abbreviation: BPAFLP)

Into a 100-mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by stirring under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere, and was reacted.

After the reaction, 200 mL of toluene was added to this reaction mixture solution, and this suspension was filtrated through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (with a developing solvent of toluene and hexane in a 1:4 ratio). The obtained fractions were concentrated, and acetone and methanol were added to the mixture. The mixture was irradiated with ultrasonic waves and then recrystallized to give 4.1 g of a white powder in 92% yield, which is the substance to be produced. A reaction scheme of the above synthesis method is illustrated in the following (E-2).

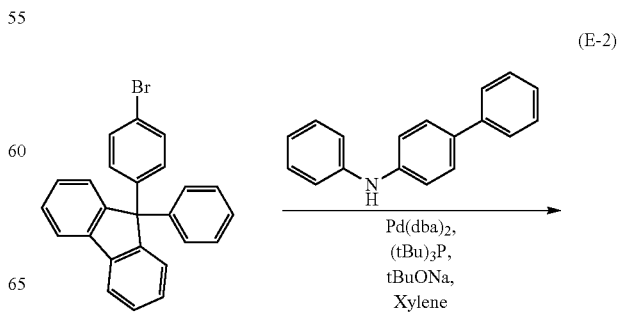

-continued

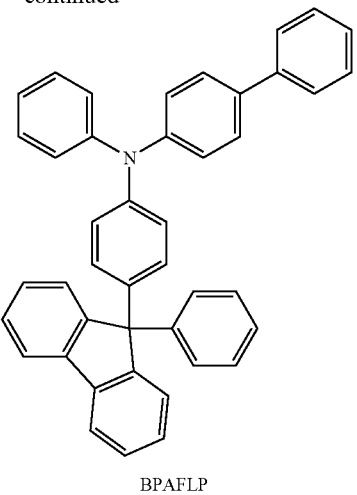

BPAFLP

The Rf values of the substance to be produced, 9-(4-bromophenyl)-9-phenylfluorene, and 4-phenyl-diphenylamine were respectively 0.41, 0.51, and 0.27, which were found by silica gel thin layer chromatography (TLC) (with a developing solvent of ethyl acetate and hexane in a 1:10 ratio).

The compound obtained by the above Step 2 was subjected to a nuclear magnetic resonance (NMR) method. The measurement data are shown below. The measurement results indicate that the obtained compound was BPAFLP, which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

This application is based on Japanese Patent Application serial no. 2010-116997 filed with the Japan Patent Office on May 21, 2010, the entire contents of which are hereby incorporated by reference.

What is claimed is:

1. A triazole derivative represented by formula (100),

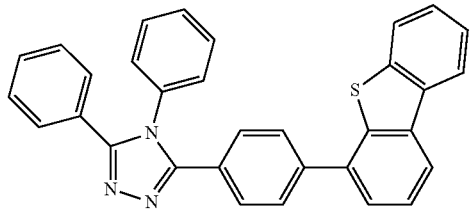
(100)

2. A light-emitting element comprising the triazole derivative according to claim 1 between a pair of electrodes.
3. A light-emitting element comprising:
a light-emitting layer between a pair of electrodes,
wherein the light-emitting layer includes the triazole derivative according to claim 1.
4. A light-emitting element comprising:
a light-emitting layer between a pair of electrodes,
wherein the light-emitting layer includes the triazole derivative according to claim 1 and a substance emitting phosphorescence.

5. The light-emitting element according to claim 4,
wherein the substance emitting phosphorescence has an emission peak at a wavelength greater than or equal to 400 nm and less than or equal to 500 nm.
6. A light-emitting device comprising the light-emitting element according to claim 2.
7. An electronic device comprising the light-emitting device according to claim 6.
8. A lighting device comprising the light-emitting element according to claim 2.
9. A triazole derivative represented by General Formula (G1),
wherein a substituent represented by General Formula (G2) is bonded to Ar$^3$, and

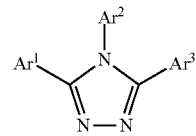
(G1)

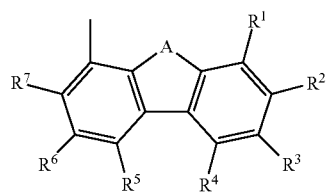
(G2)

wherein:
A represents sulfur;
Ar$^3$ represents an unsubstituted phenylene group;
Ar$^1$ and Ar$^2$ separately represent an unsubstituted phenyl group; and
R$^1$ to R$^7$ separately represent hydrogen, an alkyl group having 1 to 4 carbon atoms, or a substituted or unsubstituted aryl group having 6 to 13 carbon atoms.
10. A light-emitting element comprising the triazole derivative according to claim 9 between a pair of electrodes.
11. A light-emitting element comprising:
a light-emitting layer between a pair of electrodes,
wherein the light-emitting layer includes the triazole derivative according to claim 9.
12. A light-emitting element comprising:
a light-emitting layer between a pair of electrodes,
wherein the light-emitting layer includes the triazole derivative according to claim 9 and a substance emitting phosphorescence.
13. The light-emitting element according to claim 12,
wherein the substance emitting phosphorescence has an emission peak at a wavelength greater than or equal to 400 nm and less than or equal to 500 nm.
14. A light-emitting device comprising the light-emitting element according to claim 11.
15. An electronic device comprising the light-emitting device according to claim 14.
16. A lighting device comprising the light-emitting element according to claim 10.

* * * * *